(12) United States Patent
Murray et al.

(10) Patent No.: US 7,880,012 B2
(45) Date of Patent: Feb. 1, 2011

(54) BENZAMIDE GLUCOKINASE ACTIVATORS

(75) Inventors: Anthony Murray, Charlottenlund (DK); Jesper Lau, Farum (DK); Lone Jeppesen, Virum (DK); Per Vedso, Vaerlose (DK)

(73) Assignee: TransTech Pharma, Inc., High Point, NC (US)

( * ) Notice: Subject to any disclaimer, the term of this patent is extended or adjusted under 35 U.S.C. 154(b) by 0 days.

(21) Appl. No.: 12/298,852

(22) PCT Filed: Apr. 27, 2007

(86) PCT No.: PCT/EP2007/054170

§ 371 (c)(1), (2), (4) Date: Dec. 31, 2008

(87) PCT Pub. No.: WO2007/125103

PCT Pub. Date: Nov. 8, 2007

(65) Prior Publication Data

US 2009/0176991 A1   Jul. 9, 2009

(30) Foreign Application Priority Data

Apr. 28, 2006   (EP) ................... 06113293

(51) Int. Cl.
*C07D 277/36*   (2006.01)
(52) U.S. Cl. ................................... 548/185
(58) Field of Classification Search ........... None
See application file for complete search history.

(56) References Cited

U.S. PATENT DOCUMENTS 4,994,479 A   2/1991   Mase et al.

FOREIGN PATENT DOCUMENTS

| EP | 1529530 | 5/2005 |
|----|---------|--------|
| WO | WO 03/015774 | 2/2003 |

OTHER PUBLICATIONS

El-Dine et al. "Chemical Studies in the Field of Oral Hypoglycaemic Agents," J. Drug Res. Egypt, vol. 6, No. 3 (1974) pp. 203-207.*
European Report of Patentability for European Patent Application No. 07728625.0 dated Sep. 10, 2009.
PCT International Search Report for Application No. PCT/EP2007/054170 dated Feb. 28, 2008.
PCT Written Opinion for Application No. PCT/EP2007/054170 dated Feb. 28, 2008.

* cited by examiner

*Primary Examiner*—Rei-Tsang Shiao
*Assistant Examiner*—Alicia L Otton
(74) *Attorney, Agent, or Firm*—Townsend and Townsend and Crew LLP

(57) ABSTRACT

The present invention relates to N-heteroaryl-benzamides of the formula (I), pharmaceutical compositions comprising the same, and methods of using the same. The N-heteroaryl-benzamides are useful as glucokinase activators.

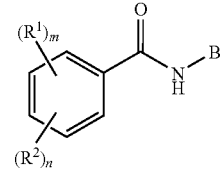

(I)

17 Claims, No Drawings

BENZAMIDE GLUCOKINASE ACTIVATORS

This application is a national stage filing under 35 USC 371 of PCT/EP2007/054170, currently pending, filed Apr. 27, 2007 and published as WO2007/125103.

FIELD OF THE INVENTION

The present invention relates to N-heteroaryl-benzamides, pharmaceutical compositions comprising the same, and methods of using the same. The N-heteroaryl-benzamides are useful as glucokinase activators.

BACKGROUND OF THE INVENTION

Glucokinase (GK) is one of four hexokinases that are found in mammals. The hexokinases catalyze the first step in the metabolism of glucose, i.e., the conversion of glucose to glucose-6-phosphate. Glucokinase has a limited cellular distribution, being found principally in pancreatic beta-cells and liver parenchymal cells. In addition, GK is a rate-controlling enzyme for glucose metabolism in these two cell types that are known to play critical roles in whole-body glucose homeostasis. Compounds that activate GK and, thereby, increase the sensitivity of the GK sensor system will still be useful in the treatment of diseases or medical conditions mediated by GK. Glucokinase activators will increase the flux of glucose metabolism in beta-cells and hepatocytes, and such agents would be useful for treating diseases or medical conditions mediated by GK. Several GK activators are known, see, for example, US 2004/0014968 (Hofmann-La Roche Inc.), WO 2004/002481 (Novo Nordisk A/S), and WO 03/015774 (AstraZeneca UK Limited).

SUMMARY OF THE INVENTION

In an aspect, the present invention provides novel N-heteroaryl-benzamides or pharmaceutically acceptable salts thereof that are useful as glucokinase activators.

In another aspect, the present invention provides novel pharmaceutical compositions comprising a pharmaceutically acceptable carrier and a therapeutically effective amount of at least one of the compounds of the present invention or a pharmaceutically acceptable salt thereof.

In another aspect, the present invention provides a novel method of treating type II diabetes comprising administering to a patient in need thereof a therapeutically effective amount of at least one compound of the present invention or a pharmaceutically acceptable salt thereof.

In another aspect, the present invention provides a novel method of treating a condition or disease, comprising administering to a patient in need thereof a therapeutically effective amount of at least one compound of the present invention or a pharmaceutically acceptable salt thereof, wherein the condition or disorder is selected from a metabolic disorder, blood glucose lowering, hyperglycemia, impaired glucose tolerance (IGT), Syndrome X, Polycystic Ovarian Syndrome, impaired fasting glucose (IFG), type I diabetes, delaying the progression of impaired glucose tolerance (IGT) to type II diabetes, delaying the progression of non-insulin requiring type II diabetes to insulin requiring type II diabetes, dyslipidemia, hyperlipidemia, hypertension, treatment or prophylaxis of obesity, lowering of food intake, appetite regulation, regulating feeding behaviour, and enhancing the secretion of enteroincretins.

In another aspect, the present invention provides novel N-heteroaryl-benzamides for use in therapy.

In another aspect, the present invention provides the use of novel N-heteroaryl-benzamides for the manufacture of a medicament for the treatment of type II diabetes.

In another aspect, the present invention provides the use of novel N-heteroaryl-benzamides for the manufacture of a medicament for the treatment of a condition or disorder selected from a metabolic disorder, blood glucose lowering, hyperglycemia, impaired glucose tolerance (IGT), Syndrome X, Polycystic Ovarian Syndrome, impaired fasting glucose (IFG), type I diabetes, delaying the progression of impaired glucose tolerance (IGT) to type II diabetes, delaying the progression of non-insulin requiring type II diabetes to insulin requiring type II diabetes, dyslipidemia, hyperlipidemia, hypertension, treatment or prophylaxis of obesity, lowering of food intake, appetite regulation, regulating feeding behaviour, and enhancing the secretion of enteroincretins.

These and other objects, which will become apparent during the following detailed description, have been achieved by the inventors' discovery that compounds of formula I:

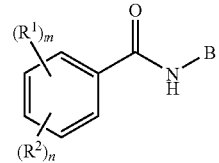

Formula I are effective glucokinase activators.

DESCRIPTION OF THE INVENTION

Glucokinase (GK) is one of four hexokinases that are found in mammals [Colowick, S. P., in The Enzymes, Vol. 9 (P. Boyer, ed.) Academic Press, New York, N.Y., pages 1-48, 1973]. The hexokinases catalyze the first step in the metabolism of glucose, i.e., the conversion of glucose to glucose-6-phosphate. Glucokinase has a limited cellular distribution, being found principally in pancreatic beta-cells and liver parenchymal cells. In addition, GK is a rate-controlling enzyme for glucose metabolism in these two cell types that are known to play critical roles in whole-body glucose homeostasis [Chipkin, S. R., Kelly, K. L., and Ruderman, N. B. in Joslin's Diabetes (C. R. Khan and G. C. Wier, eds.), Lea and Febiger, Philadelphia, Pa., pages 97-115, 1994]. The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial ($\approx$10-15 mM) levels following a carbohydrate-containing meal [Printz, R. G., Magnuson, M. A., and Granner, D. K. in Ann. Rev. Nutrition Vol. 13 (R. E. Olson, D. M. Bier, and D. B. McCormick, eds.), Annual Review, Inc., Palo Alto, Calif., pages 463-496, 1993]. These findings contributed over a decade ago to the hypothesis that GK functions as a glucose sensor in beta-cells and hepatocytes (Meglasson, M. D. and Matschinsky, F. M. Amer. J. Physiol. 246, E1-E13, 1984). In recent years, studies in transgenic animals have confirmed that GK does indeed play a critical role in whole-body glucose homeostasis. Animals that do not express GK die within days of birth with severe diabetes while animals overexpressing GK have improved glucose tolerance (Grupe, A., Hultgren, B., Ryan, A. et al., Cell 83, 69-78, 1995; Ferrie, T., Riu, E., Bosch, F. et al., FASEB J., 10, 1213-1218, 1996). An increase in glucose exposure is coupled through GK in beta-cells to increased insulin secretion and in hepatocytes to increased glycogen deposition and perhaps decreased glucose production. The finding that type 2 maturity-onset diabetes of the young (MODY-2) is caused by loss of function mutations in the GK gene suggests that GK also functions as a glucose sensor in humans (Liang, Y., Kesavan, P., Wang, L. et al., Biochem. J. 309, 167-173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., New England J. Med. 338, 226-230, 1998). While mutations of the GK gene are not found in the majority of patients with type 2 diabetes, compounds that activate GK and, thereby, increase the sensitivity of the GK sensor system will still be useful in the treatment of the diseases or medical conditions mediated by glucokinase.

Diabetes is characterised by an impaired glucose metabolism manifesting itself among other things by an elevated blood glucose level in the diabetic patients. Underlying defects lead to a classification of diabetes into two major groups: Type 1 diabetes, or insulin demanding diabetes mellitus (IDDM), which arises when patients lack β-cells producing insulin in their pancreatic glands, and type 2 diabetes, or non-insulin dependent diabetes mellitus (NIDDM), which occurs in patients with an impaired β-cell function besides a range of other abnormalities.

Type 1 diabetic patients are currently treated with insulin, while the majority of type 2 diabetic patients are treated either with sulphonylureas that stimulate β-cell function or with agents that enhance the tissue sensitivity of the patients towards insulin or with insulin. Among the agents applied to enhance tissue sensitivity towards insulin, metformin is a representative example.

Even though sulphonylureas are widely used in the treatment of NIDDM this therapy is, in most instances, not satisfactory: In a large number of NIDDM patients sulphonylureas do not suffice to normalise blood sugar levels and the patients are, therefore, at high risk for acquiring diabetic complications. Also, many patients gradually lose the ability to respond to treatment with sulphonylureas and are thus gradually forced into insulin treatment. This shift of patients from oral hypoglycaemic agents to insulin therapy is usually ascribed to exhaustion of the β-cells in NIDDM patients.

In normal subjects as well as in diabetic subjects, the liver produces glucose in order to avoid hypoglycaemia. This glucose production is derived either from the release of glucose from glycogen stores or from gluconeogenesis, which is a de novo intracellular synthesis of glucose. In type 2 diabetes, however, the regulation of hepatic glucose output is poorly controlled and is increased, and may be doubled after an overnight fast. Moreover, in these patients there exists a strong correlation between the increased fasting plasma glucose levels and the rate of hepatic glucose production. Similarly, hepatic glucose production will be increased in type 1 diabetes, if the disease is not properly controlled by insulin treatment.

Since existing forms of therapy of diabetes does not lead to sufficient glycaemic control and therefore are unsatisfactory, there is a great demand for novel therapeutic approaches.

Atherosclerosis, a disease of the arteries, is recognized to be the leading cause of death in the United States and Western Europe. The pathological sequence leading to atherosclerosis and occlusive heart disease is well known. The earliest stage in this sequence is the formation of "fatty streaks" in the carotid, coronary and cerebral arteries and in the aorta. These lesions are yellow in colour due to the presence of lipid deposits found principally within smooth-muscle cells and in macrophages of the intima layer of the arteries and aorta. Further, it is postulated that most of the cholesterol found within the fatty streaks, in turn, give rise to development of the "fibrous plaque", which consists of accumulated intimal smooth muscle cells laden with lipid and surrounded by extracellular lipid, collagen, elastin and proteoglycans. The cells plus matrix form a fibrous cap that covers a deeper deposit of cell debris and more extracellular lipid. The lipid is primarily free and esterified cholesterol. The fibrous plaque forms slowly, and is likely in time to become calcified and necrotic, advancing to the "complicated lesion" which accounts for the arterial occlusion and tendency toward mural thrombosis and arterial muscle spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at particular high risk. Independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

Hypertension (or high blood pressure) is a condition, which occurs in the human population as a secondary symptom to various other disorders such as renal artery stenosis, pheochromocytoma, or endocrine disorders. However, hypertension is also evidenced in many patients in whom the causative agent or disorder is unknown. While such "essential" hypertension is often associated with disorders such as obesity, diabetes, and hypertriglyceridemia, the relationship between these disorders has not been elucidated. Additionally, many patients display the symptoms of high blood pressure in the complete absence of any other signs of disease or disorder.

It is known that hypertension can directly lead to heart failure, renal failure, and stroke (brain hemorrhaging). These conditions are capable of causing short-term death in a patient. Hypertension can also contribute to the development of atherosclerosis and coronary disease. These conditions gradually weaken a patient and can lead to long-term death.

The exact cause of essential hypertension is unknown, though a number of factors are believed to contribute to the onset of the disease. Among such factors are stress, uncontrolled emotions, unregulated hormone release (the renin, angiotensin aldosterone system), excessive salt and water due to kidney malfunction, wall thickening and hypertrophy of the vasculature resulting in constricted blood vessels and genetic factors.

The treatment of essential hypertension has been undertaken bearing the foregoing factors in mind. Thus a broad range of beta-blockers, vasoconstrictors, angiotensin converting enzyme inhibitors and the like have been developed and marketed as antihypertensives. The treatment of hypertension utilizing these compounds has proven beneficial in the prevention of short-interval deaths such as heart failure, renal failure, and brain hemorrhaging. However, the development of atherosclerosis or heart disease due to hypertension over a long period of time remains a problem. This implies that although high blood pressure is being reduced, the underlying cause of essential hypertension is not responding to this treatment.

Hypertension has been associated with elevated blood insulin levels, a condition known as hyperinsulinemia. Insulin, a peptide hormone whose primary actions are to promote glucose utilization, protein synthesis and the formation and storage of neutral lipids, also acts to promote vascular cell growth and increase renal sodium retention, among other things. These latter functions can be accomplished without affecting glucose levels and are known causes of hypertension. Peripheral vasculature growth, for example, can cause constriction of peripheral capillaries, while sodium retention increases blood volume. Thus, the lowering of insulin levels in hyperinsulinemics can prevent abnormal vascular growth and renal sodium retention caused by high insulin levels and thereby alleviates hypertension.

Cardiac hypertrophy is a significant risk factor in the development of sudden death, myocardial infarction, and congestive heart failure. Theses cardiac events are due, at least in part, to increased susceptibility to myocardial injury after ischemia and reperfusion, which can occur in out-patient as well as perioperative settings. There is an unmet medical need to prevent or minimize adverse myocardial perioperative outcomes, particularly perioperative myocardial infarction. Both non-cardiac and cardiac surgery are associated with substantial risks for myocardial infarction or death. Some 7 million patients undergoing non-cardiac surgery are considered to be at risk, with incidences of perioperative death and serious cardiac complications as high as 20-25% in some series. In addition, of the 400,000 patients undergoing coronary by-pass surgery annually, perioperative myocardial infarction is estimated to occur in 5% and death in 1-2%. There is currently no drug therapy in this area, which reduces damage to cardiac tissue from perioperative myocardial ischemia or enhances cardiac resistance to ischemic episodes. Such a therapy is anticipated to be life-saving and reduce hospitalizations, enhance quality of life and reduce overall health care costs of high risk patients.

Obesity is a well-known risk factor for the development of many very common diseases such as atherosclerosis, hypertension, and diabetes. The incidence of obese people and thereby also these diseases is increasing throughout the entire industrialised world. Except for exercise, diet and food restriction no convincing pharmacological treatment for reducing body weight effectively and acceptably currently exists. However, due to its indirect but important effect as a risk factor in mortal and common diseases it will be important to find treatment for obesity and/or means of appetite regulation.

The term obesity implies an excess of adipose tissue. In this context obesity is best viewed as any degree of excess adiposity that imparts a health risk. The cut off between normal and obese individuals can only be approximated, but the health risk imparted by the obesity is probably a continuum with increasing adiposity. The Framingham study demonstrated that a 20% excess over desirable weight clearly imparted a health risk (Mann G V N. Engl. J. Med 291:226, 1974). In the United States a National Institutes of Health consensus panel on obesity agreed that a 20% increase in relative weight or a body mass index (BMI=body weight in kilograms divided by the square of the height in meters) above the 85th percentile for young adults constitutes a health risk. By the use of these criteria 20 to 30 percent of adult men and 30 to 40 percent of adult women in the United States are obese. (NIH, Ann Intern Med 103:147, 1985).

Even mild obesity increases the risk for premature death, diabetes, hypertension, atherosclerosis, gallbladder disease, and certain types of cancer. In the industrialised western world the prevalence of obesity has increased significantly in the past few decades. Because of the high prevalence of obesity and its health consequences, its prevention and treatment should be a high public health priority.

When energy intake exceeds expenditure, the excess calories are stored in adipose tissue, and if this net positive balance is prolonged, obesity results, i.e. there are two components to weight balance, and an abnormality on either side (intake or expenditure) can lead to obesity.

The regulation of eating behaviour is incompletely understood. To some extent appetite is controlled by discrete areas in the hypothalamus: a feeding centre in the ventrolateral nucleus of the hypothalamus (VLH) and a satiety centre in the ventromedial hypothalamus (VMH). The cerebral cortex receives positive signals from the feeding centre that stimulate eating, and the satiety centre modulates this process by sending inhibitory impulses to the feeding centre. Several regulatory processes may influence these hypothalamic centres. The satiety centre may be activated by the increases in plasma glucose and/or insulin that follow a meal. Meal-induced gastric distension is another possible inhibitory factor. Additionally the hypothalamic centres are sensitive to catecholamines, and beta-adrenergic stimulation inhibits eating behaviour. Ultimately, the cerebral cortex controls eating behaviour, and impulses from the feeding centre to the cerebral cortex are only one input. Psychological, social, and genetic factors also influence food intake.

At present a variety of techniques are available to effect initial weight loss. Unfortunately, initial weight loss is not an optimal therapeutic goal. Rather, the problem is that most obese patients eventually regain their weight. An effective means to establish and/or sustain weight loss is the major challenge in the treatment of obesity today.

In an aspect 1 the invention provides a compound according to formula I

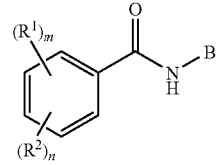

Formula I wherein m is 0, 1, or 2;

n is 0, 1, 2, 3 or 4;

n+m>0;

Each $R^1$ is independently selected from OH, —$(CH_2)_{1-4}$OH, —$CH_{3-a}F_a$, —$(CH_2)_{1-4}$—$CH_{3-a}F_a$, —$OCH_{3-a}F_a$, Cl, F, Br, I, $C_{1-6}$-alkyl, $C_{2-6}$-alkenyl, $C_{2-6}$-alkynyl, amino, $C_{1-4}$-alkyl-amino, $C_{1-4}$-dialkyl-amino, cyano, formyl, phenyl, or 5-10 membered heterocyclyl, wherein the heterocyclyl consists of carbon atoms and 1-4 heteroatoms selected from O, N, and S(O)$_t$ optionally substituted with $C_{1-6}$-alkyl;

Each $R^2$ is a group Y—X—
  wherein each X is a linker independently selected from
    —O—Z—, O—Z—O—Z—, —C(O)O—Z—, —OC(O)—Z—, —S—Z—, —S(O)—Z—, —S(O)$_2$—Z—, —N(R$^6$)—Z—, —N(R$^6$)S(O)$_2$—Z, —S(O)$_2$N(R$^6$)—Z, —(CH$_2$)$_{1-4}$—, —CH=CH—Z—, —C≡C—Z—, —N(R$^6$)C(O)—Z—, —C(O)N(R$^6$)—Z—, —C(O)N(R$^6$)S(O)$_2$—Z—, —S(O)$_2$—N(R$^6$)C(O)—Z—, —C(O)—Z—, —Z—, —C(O)—Z—O—Z, —N(R$^6$)—C(O)—Z—O—Z, —O—Z—N(R$^6$)—Z, —O—C(O)—Z—O—Z or a direct bond,
    wherein X is attached to the phenyl ring by the first-mentioned atom;

Each Z is independently selected from a direct bond, $C_{2-6}$-alkenylene, and —(CH$_2$)$_p$—C(R$^{10}$)$_2$—(CH$_2$)$_q$—;

Each Y is independently selected from aryl-Z$^1$—, a 5-10 membered heterocyclyl-Z$^1$—, wherein the heterocyclyl consists of carbon atoms and 1-4 heteroatoms selected from O, N, and S(O)$_r$; $C_{3-7}$-cycloalkyl-Z$^1$—, $C_{1-6}$-alkyl, $C_{2-6}$-alkenyl, $C_{2-6}$-alkynyl, —(CH$_2$)$_{1-4}$—CH$_{3-a}$F$_a$, —CH(OH)CH$_{3-a}$F$_a$, wherein each Y is optionally substituted with 1-3 substituents independently selected from R$^4$;

Z$^1$ is independently selected from a direct bond, $C_{2-6}$-alkenylene, and —(CH$_2$)$_p$—C(R$^{10}$)$_2$—(CH$_2$)$_q$—;

At each occurrence, p is independently selected from 0, 1, 2, and 3;

At each occurrence, q is independently selected from 0, 1, 2, and 3;

$R^4$ is independently selected from R$^5$—X$^1$—, Cl, F, Br, I, CH$_{3-a}$F$_a$, —CN, NH$_2$, $C_{1-6}$-alkyl, —O—$C_{1-6}$alkyl, —C(O)OH, —C(O)OR$^7$, OH, and phenyl optionally substituted by R$^7$;

or two R$^4$ attached to adjacent atoms may form a —O—(CH$_2$)$_{1-2}$—O— bridge;

or $R^4$ is selected from —C(O)NR$^{26}$R$^{27}$, —S(O)$_2$NR$^{26}$R$^{27}$, —S(O)$_r$R$^{26}$ and HET-2;

$X^1$ is independently defined as X above:

$R^5$ is selected from H, $C_{1-6}$-alkyl, CH$_2$F, CHF$_2$, CF$_3$, phenyl, naphthyl, a 5-10 membered heterocyclyl consisting of carbon atoms and 1-4 heteroatoms selected from O, N, and S(O)$_r$, and $C_{3-7}$cycloalkyl, wherein each R$^5$ is optionally substituted by one or more substituents independently selected from R$^{25}$ $R^{25}$ is independently selected from Cl, F, Br, I, $C_{1-6}$-alkyl, —O$C_{1-6}$-alkyl, CH$_{3-a}$F$_a$, —CN, OH, NH$_2$, C(O)OH, or —C(O)O$C_{1-6}$alkyl;

$R^6$ is independently selected from hydrogen, $C_{1-6}$-alkyl, —$C_{2-4}$-alkyl-O—$C_{1-4}$-alkyl;

$R^7$ is independently selected from $C_{1-6}$-alkyl and —C(O)O$C_{1-6}$-alkyl;

B is a 5-10 membered heterocyclyl, wherein the heterocyclyl consists of carbon atoms and 1-4 heteroatoms selected from O, N, and S(O)$_r$, substituted with one or more substituents independently selected from R$^8$;

$R^8$ is independently selected from —S(O)$_r$(CH$_2$)$_s$—R$^9$ and —(CH$_2$)$_u$S(O)$_r$(CH$_2$)$_s$—R$^9$;

r is 0, 1 or 2;

s is 1, 2, 3, or 4;

u is 1, 2, 3, or 4;

$R^9$ is independently selected from carboxy, —C(O)O—$C_{1-6}$-alkyl, —NR$^{19}$R$^{20}$, —C(O)NR$^{19}$R$^{20}$ or —S(O)$_2$—$C_{1-6}$-alkyl;

$R^{10}$ is independently selected from H, Cl, F, Br, I, $C_{1-6}$-alkyl, and —$C_{2-4}$-alkyl-O—$C_{1-4}$alkyl;

$R^{18}$ is selected from hydrogen and $C_{1-6}$-alkyl;

$R^{19}$ and $R^{20}$ independently represent hydrogen, $C_{1-6}$-alkyl, $C_{2-6}$-alkenyl, $C_{3-8}$-cycloalkyl, $C_{3-8}$-cycloalkyl-$C_{1-6}$-alkyl, hydroxy-$C_{1-6}$-alkyl, hydroxy-$C_{2-6}$-alkenyl, carboxy-$C_{1-6}$-alkyl, aryl, heteroaryl, $C_{3-8}$-heterocyclyl, aryl-$C_{1-6}$-alkyl, $C_{3-8}$-heterocyclyl-$C_{1-6}$-alkyl, —C(O)—O—$C_{1-6}$-alkyl, —$C_{1-6}$-alkyl-C(O)—O—$C_{1-6}$-alkyl, or —S(O)$_2$—$C_{1-6}$-alkyl, each of which is optionally substituted with one or more substituents independently selected from R$^{24}$, or $R^{19}$ and $R^{20}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from R$^{24}$;

$R^{24}$ is independently selected from halogen, nitro, cyano, hydroxy, carboxy, oxo, —CF$_3$, $C_{1-6}$-alkyl, hydroxy-$C_{1-6}$-alkyl, carboxy-$C_{1-6}$-alkyl, —C(O)—$C_{1-6}$-alkyl, —C(O)—$C_{3-8}$-cycloalkyl, and —C(O)-aryl;

$R^{26}$ is selected from
  hydrogen,
  $C_{1-4}$-alkyl optionally substituted with one or two substituents independently selected from
    HET-2, —OR$^{27}$—S(O)$_2$R$^{27}$, $C_{3-6}$-cycloalkyl optionally substituted with one R$^{28}$ and —C(O)NR$^{27}$R$^{27}$,
  $C_{3-6}$-cycloalkyl optionally substituted with one R$^{28}$, and
  HET-2;

$R^{27}$ is selected from hydrogen and $C_{1-4}$-alkyl;

or R$^{26}$ and R$^{27}$ together with the nitrogen atom to which they are attached form a heterocyclyl ring as defined in HET-3

HET-2 is a 4-, 5-, or 6-membered C- or N-linked heterocyclyl ring containing 1, 2, 3, or 4 heteroatoms independently selected from O, N, and S, wherein a —CH$_2$— group can optionally be replaced by a —C(O)— group, and wherein a sulphur atom in the heterocyclic ring may optionally be oxidised to an S(O) or S(O)$_2$ group, which ring is optionally substituted on an available carbon or nitrogen atom by one or two substituents independently selected from R$^{28}$;

HET-3 is a 4-, 5-, or 6-membered N-linked saturated or partially unsaturated heterocyclyl ring optionally containing 1 or 2 further heteroatoms (in addition to the linking nitrogen atom) independently selected from O, N, and S, wherein a —CH$_2$— group can optionally be replaced by a —C(O)— group, and wherein a sulphur atom in the ring may optionally be oxidised to an S(O) or S(O)$_2$ group, which ring is optionally substituted on an available carbon or nitrogen atom by one or two substituents independently selected from R$^{29}$; or HET-3 is an N-linked, 7-membered saturated or partially unsaturated heterocyclyl ring optionally containing one further heteroatom (in addition to the linking nitrogen atom) independently selected from O, N, and S, wherein a —CH$_2$— group can optionally be replaced by a —C(O)—, and wherein a sulphur atom in the heterocyclic ring may optionally be oxidised to an S(O) or S(O)$_2$ group, which ring is optionally substituted on an available carbon or nitrogen atom by one or two substituents independently selected from $R^{29}$; or HET-3 is a 6-10 membered bicyclic saturated or partially unsaturated heterocyclyl ring optionally containing one further nitrogen atom (in addition to the linking nitrogen atom), wherein a —CH$_2$— group can optionally be replaced by a —C(O)—, which ring is optionally substituted on an available carbon or nitrogen atom by one substituent independently selected from $R^{30}$;

$R^{29}$ is independently selected from —OR$^{27}$, $C_{1-4}$-alkyl, —C(O)—$C_{1-4}$-alkyl, —C(O)NR$^{26}$R$^{27}$, $C_{1-4}$-alkylamino, di($C_{1-4}$-alkyl)amino, HET-3 (wherein said ring is unsubstituted), $C_{1-4}$-alkoxy$C_{1-4}$-alkyl, hydroxy$C_{1-4}$-alkyl, and —S(O)$_t$R$^{26}$;

$R^{30}$ is independently selected from hydroxy, halo, fluoromethyl, difluoromethyl, trifluoromethyl, methyl, methoxy and cyano;

t is independently selected, at each occurrence, from 0, 1, and 2;

a is independently selected from 1, 2, and 3.

Aspect 2. A compound according to aspect 1 wherein $R^1$ is independently selected from —CH$_2$F, —CHF$_2$, —CF$_3$, Cl, F, and $C_{1-6}$-alkyl.

Aspect 3. A compound according to aspect 2 wherein $R^1$ is independently selected from —CF$_3$, Cl, F, and $C_{1-6}$-alkyl.

Aspect 4. A compound according to aspect 3 wherein $R^1$ is independently selected from —CF$_3$, Cl, F, methyl and ethyl.

Aspect 5. A compound according to any one of the aspects 1 to 4 wherein X is independently selected from —O—Z— or —O—Z—O—Z—.

Aspect 6. A compound according to aspect 5 wherein X is —O—Z—.

Aspect 7. A compound according to aspect 5 wherein X is —O—Z—O—Z—.

Aspect 8. A compound according to any one of the aspects 1 to 7 wherein Z is a direct bond or —(CH$_2$)$_p$—C(R$^{10}$)$_2$—(CH$_2$)$_q$—.

Aspect 9. A compound according to aspect 8 wherein Z is a direct bond.

Aspect 10. A compound according to aspect 8 wherein Z is —(CH$_2$)$_p$—C(R$^{10}$)$_2$—(CH$_2$)$_q$—.

Aspect 11. A compound according to any one of the aspects 1 to 10 wherein $R^{10}$ is CH$_3$.

Aspect 12. A compound according to any one of the aspects 1 to 10 wherein $R^{10}$ is H.

Aspect 13. A compound according to any one of the aspects 1 to 12 wherein p and q are both 0.

Aspect 14. A compound according to any one of the aspects 1 to 12 wherein p is 0 and q is 1.

Aspect 15. A compound according to any one of the aspects 1 to 14 wherein Y is phenyl-Z$^1$—, naphtyl-Z$^1$—, a 5-10 membered heterocyclyl-Z$^1$—, wherein the heterocyclyl consists of carbon atoms and 1-4 heteroatoms selected from O, N, and S(O)$_t$, or $C_{3-7}$cycloalkyl-Z$^1$—, wherein each Y is optionally substituted with 1-3 substituents independently selected from $R^4$.

Aspect 16. A compound according to aspect 15 wherein Y is phenyl-Z$^1$—, a 5-10 membered heterocyclyl-Z$^1$—, wherein the heterocyclyl consists of carbon atoms and 1-4 heteroatoms selected from O, N, and S(O)$_t$, or $C_{3-7}$cycloalkyl-Z$^1$—, wherein each Y is optionally substituted with 1-3 substituents independently selected from $R^4$.

Aspect 17. A compound according to aspect 16 wherein Y is phenyl-Z$^1$ optionally substituted with 1-3 substituents independently selected from $R^4$.

Aspect 18. A compound according to any one of the aspects 1 to 17 wherein Z$^1$ is a direct bond or —(CH$_2$)$_p$—C(R$^{10}$)$_2$—(CH$_2$)$_q$—.

Aspect 19. A compound according to aspect 18 wherein Z$^1$ is a direct bond.

Aspect 20. A compound according to any one of the aspects 15 to 19 wherein $R^{10}$ is CH$_3$.

Aspect 21. A compound according to any one of the aspects 15 to 19 wherein $R^{10}$ is H.

Aspect 22. A compound according to any one of the aspects 1 to 21 wherein p and q are both 0.

Aspect 23. A compound according to any one of the aspects 1 to 21 wherein p is 0 and q is 1.

Aspect 24. A compound according to any one of the aspects 1 to 23 wherein $R^4$ is independently selected from $R^5$—X$^1$—, Cl, F, $C_{1-6}$-alkyl or —OC$_{1-6}$-alkyl.

Aspect 25. A compound according to aspect 24 wherein $R^4$ is independently selected from Cl, F, methyl, ethyl, methoxy or ethoxy.

Aspect 26. A compound according to aspect 25 $R^4$ is methoxy.

Aspect 27. A compound according to aspect 25 $R^4$ is methyl.

Aspect 28. A compound according to aspect 24 wherein $R^4$ is $R^5$—X$^1$—.

Aspect 29. A compound according to any one of the aspects 1 to 28 wherein X$^1$ is O.

Aspect 30. A compound according to any one of the aspects 1 to 29 wherein $R^5$ is $C_{1-6}$alkyl, CH$_2$F, CHF$_2$, or CF$_3$, and each $R^5$ is optionally substituted by one or more substituents independently selected from $R^{23}$.

Aspect 31. A compound according to aspect 30 wherein $R^5$ is methyl, ethyl or propyl.

Aspect 32. A compound according to any one of the aspects 1 to 31 wherein $R^{26}$ is Cl, F, or methyl.

Aspect 33. A compound according to any one of the aspects 1 to 32 wherein $R^7$ is $C_{1-8}$-alkyl.

Aspect 34. A compound according to aspect 33 wherein $R^7$ is methyl, ethyl or propyl.

Aspect 35. A compound according to any one of the aspects 1 to 23 wherein two $R^4$ attached to adjacent atoms form a —O—(CH$_2$)$_1$—O— bridge.

Aspect 36. A compound according to any one of the aspects 1 to 23 wherein two $R^4$ attached to adjacent atoms form a —O—(CH$_2$)$_2$—O— bridge.

Aspect 37. A compound according to any one of the aspects 1 to 23 wherein $R^4$ is selected from —C(O)NR$^{26}$R$^{27}$, —S(O)$_2$NR$^{26}$R$^{27}$ and HET-2.

Aspect 38. A compound according to aspect 37 wherein $R^4$ is selected from —C(O)NR$^{26}$R$^{27}$ and —S(O)$_2$NR$^{26}$R$^{27}$.

Aspect 39. A compound according to aspect 38 wherein $R^4$ is —C(O)NR$^{26}$R$^{27}$.

Aspect 40. A compound according to aspect 38 wherein $R^4$ is —S(O)$_2$NR$^{26}$R$^{27}$.

Aspect 41. A compound according to aspect 37 wherein $R^4$ is HET-2.

Aspect 42. A compound according to any one of the aspects 1 to 41 wherein $R^{26}$ is hydrogen.

Aspect 43. A compound according to any one of the aspects 1 to 41 wherein $R^{26}$ is $C_{1-4}$-alkyl optionally substituted with one or two substituents independently selected from HET-2 or —OR$^{27}$.

Aspect 44. A compound according to any one of the aspects 1 to 41 wherein $R^{26}$ is $C_{3-6}$-cycloalkyl optionally substituted with one $R^{28}$.

Aspect 45. A compound according to any one of the aspects 1 to 41 wherein $R^{26}$ is HET-2.

Aspect 46. A compound according to any one of the aspects 1 to 45 wherein $R^{27}$ is hydrogen.

Aspect 47. A compound according to any one of the aspects 1 to 45 wherein $R^{27}$ is $C_{1-4}$-alkyl.

Aspect 48. A compound according to any one of the aspects 1 to 41 wherein $R^{26}$ and $R^{27}$ together with the nitrogen atom to which they are attached form a heterocyclyl ring as defined in HET-3.

Aspect 49. A compound according to any one of the aspects 1 to 48 wherein HET-2 is selected from morpholino, furyl, imidazolyl, oxazolyl, isoxazolyl, oxadiazolyl, piperidinyl, piperazinyl, 3-oxo-piperazinyl, pyrrolidinyl, 2-pyrrolidonyl, tetrahydropyranyl, 1,1-dioxotetrahydrothienyl, and 2-oxo-imidazolidinyl, each of which is optionally substituted with on or two substituents independently selected from $R^{29}$.

Aspect 50. A compound according to any one of the aspects 1 to 49 wherein HET-3 is selected from morpholino, piperidinyl, piperazinyl, pyrrolidinyl, and azetidinyl, each of which is optionally substituted with on or two substituents independently selected from $R^{30}$.

Aspect 51. A compound according to aspect 50 wherein HET-3 is selected from pyrrolidinyl and azetidinyl, each of which is optionally substituted with on or two substituents independently selected from $R^{30}$.

Aspect 52. A compound according to aspect 51 wherein HET-3 is azetidinyl optionally substituted with on or two substituents independently selected from $R^{30}$.

Aspect 53. A compound according to any one of the aspects 1 to 52 wherein $R^{29}$ is selected from —$OR^{27}$, $C_{1-4}$-alkyl, and —C(O)—$C_{1-4}$-alkyl.

Aspect 54. A compound according to aspect 53 wherein $R^{29}$ is selected from —$OR^{27}$ and $C_{1-4}$-alkyl.

Aspect 55. A compound according to any one of the aspects 1 to 54 wherein $R^{30}$ is independently selected from halo, fluoromethyl, difluoromethyl, trifluoromethyl, methyl, and methoxy.

Aspect 56. A compound according to aspect 55 wherein $R^{30}$ is independently selected from halo, fluoromethyl, difluoromethyl, trifluoromethyl, methyl, and methoxy.

Aspect 57. A compound according to aspect 55 wherein $R^{30}$ is independently selected from halo, fluoromethyl and methoxy.

Aspect 58. A compound according to any one of the aspects 1 to 57 wherein B is thiazolyl, 1,2,4-thiadiazolyl, or 1,3,4-thiadiazolyl substituted with $R^3$.

Aspect 59. A compound according to aspect 58 wherein B is

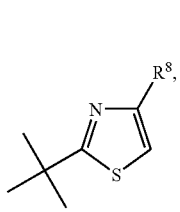 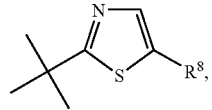

-continued

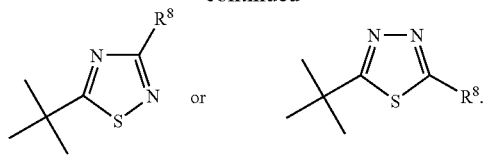

Aspect 60. A compound according to aspect 59 wherein B is

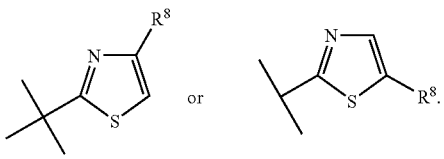

Aspect 61. A compound according to aspect 60 wherein B is

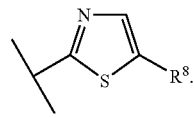

Aspect 62. A compound according to aspect 60 wherein B is

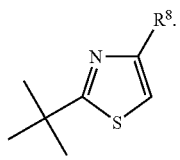

Aspect 63. A compound according to any one of the aspects 1 to 62 wherein $R^8$ is independently selected from —$S(CH_2)_{1-2}$—$R^9$, —$S(O)_2(CH_2)_{1-2}$—$R^9$, and —$CH_2S(CH_2)_{1-2}$—$R^9$.

Aspect 64. A compound according to aspect 63 wherein $R^8$ is —$S(CH_2)_{1-2}$—$R^9$.

Aspect 65. A compound according to aspect 64 wherein $R^8$ is —$S(CH_2)$—$R^9$.

Aspect 66. A compound according to aspect 64 wherein $R^8$ is —$S(CH_2)_2$—$R^9$.

Aspect 67. A compound according to aspect 63 wherein $R^8$ is —$S(O)_2(CH_2)_{1-2}$—$R^9$.

Aspect 68. A compound according to aspect 67 wherein $R^8$ is —$S(O)_2(CH_2)$—$R^9$.

Aspect 69. A compound according to aspect 67 wherein $R^8$ is —$S(O)_2(CH_2)_2$—$R^9$.

Aspect 70. A compound according to aspect 63 wherein $R^8$ is —$CH_2S(CH_2)_{1-2}$—$R^9$.

Aspect 71. A compound according to aspect 70 wherein $R^8$ is —$CH_2S(CH_2)_{1-2}$—$R^9$.

Aspect 72. A compound according to aspect 70 wherein $R^8$ is —$CH_2S(CH_2)_{1-2}$—$R^9$.

Aspect 73. A compound according to any one of the aspects 1 to 72 wherein $R^9$ is carboxy or —C(O)O—$C_{1-6}$-alkyl.

Aspect 74. A compound according to aspect 73 wherein $R^9$ is carboxy.

Aspect 75. A compound according to aspect 73 wherein $R^9$ is —C(O)O—$C_{1-6}$-alkyl.

Aspect 76. A compound according to aspect 75 wherein $R^9$ is —C(O)O—$CH_3$.

Aspect 77. A compound according to aspect 75 wherein $R^9$ is —C(O)O—$CH_2CH_3$.

Aspect 78. A compound according to any one of the aspects 1 to 62 wherein $R^{19}$ and $R^{20}$ independently represent hydrogen, $C_{1-6}$-alkyl, hydroxy-$C_{1-6}$-alkyl, carboxy-$C_{1-6}$-alkyl, phenyl, naphtyl, $C_{3-8}$-heterocyclyl, phenyl-$C_{1-6}$-alkyl, $C_{3-8}$-heterocyclyl-$C_{1-6}$-alkyl, —C(O)—O—$C_{1-6}$-alkyl, —$C_{1-6}$-alkyl-C(O)—O—$C_{1-6}$-alkyl, —$C_{1-6}$-alkyl-$NR^{22}R^{23}$ or —S(O)$_2$—$C_{1-6}$-alkyl, each of which is optionally substituted with one or more substituents independently selected from $R^{24}$; or $R^{19}$ and $R^{20}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$.

Aspect 79. A compound according to aspect 78 wherein $R^{19}$ and $R^{20}$ independently represent hydrogen, methyl, ethyl, propyl, carboxy-methyl, carboxy-ethyl, carboxy-propyl, hydroxy-methyl, hydroxy-ethyl, hydroxy-propyl, phenyl, phenyl-$C_{1-6}$-alkyl, $C_{3-8}$-heterocyclyl-$C_{1-6}$-alkyl, —C(O)—O—$C_{1-6}$-alkyl, —$C_{1-6}$-alkyl-C(O)—O—$C_{1-6}$-alkyl, —$C_{1-6}$-alkyl-$NR^{22}R^{23}$, or naphtyl, or $R^{19}$ and $R^{20}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$.

Aspect 80. A compound according to aspect 78 wherein $R^{19}$ and $R^{20}$ independently represent hydrogen, $C_{1-6}$-alkyl, or $R^{19}$ and $R^{20}$ together with the nitrogen to which they are attached form a 3 to 8 membered heterocyclic ring with the said nitrogen atom, the heterocyclic ring optionally containing one or two further heteroatoms selected from nitrogen, oxygen and sulphur, the heterocyclic ring is optionally substituted with one or more substituents independently selected from $R^{24}$.

Aspect 81. A compound according to aspect 80 wherein $R^{19}$ and $R^{20}$ independently represent hydrogen, methyl, ethyl, or propyl, or $R^{19}$ and $R^{20}$ together with the nitrogen to which they are attached form a 3 to 8 membered heterocyclic ring with the said nitrogen atom, wherein the heterocyclic ring is pyrrolidyl, piperidyl, piperazinyl, homopiperazinyl, or morpholinyl, the heterocyclic ring is optionally substituted with one or more substituents independently selected from $R^{24}$.

Aspect 82. A compound according to any one of the aspects 1 to 81 wherein $R^{24}$ is carboxy, oxo, $C_{1-6}$-alkyl, or carboxy-$C_{1-6}$-alkyl.

Aspect 83. A compound according to any one of the aspects 1 to 81 wherein t is 0.

Aspect 84. A compound according to any one of the aspects 1 to 81 wherein t is 1.

Aspect 85. A compound according to any one of the aspects 1 to 81 wherein t is 2.

Aspect 82. A compound according to any one of the aspects 1 to 85 wherein a is 1.

Aspect 82. A compound according to any one of the aspects 1 to 85 wherein a is 2.

Aspect 82. A compound according to any one of the aspects 1 to 85 wherein a is 3.

Aspect

In an aspect 83 according to any one of the aspects 1 to 82 the invention provides the use of a compound of the invention or a salt thereof in the preparation of a medicament for use in the treatment of a disease or medical condition mediated through glucokinase, wherein the disease or condition is a metabolic disorder, blood glucose lowering, hyperglycemia, impaired glucose tolerance (IGT), Syndrome X, Polycystic Ovarian Syndrome, impaired fasting glucose (IFG), type 1 diabetes, type 2 diabetes, delaying the progression of impaired glucose tolerance (IGT) to type 2 diabetes, delaying the progression of non-insulin requiring type 2 diabetes to insulin requiring type 2 diabetes, dyslipidemia, hyperlipidemia, hypertension, treatment or prophylaxis of obesity, lowering of food intake, appetite regulation, regulating feeding behaviour, and enhancing the secretion of enteroincretins.

Aspect 84. The use according to aspect 83 wherein the disease or medical disorder is type 1 diabetes.

Aspect 85. The use according to aspect 83 wherein the disease or medical disorder is type 2 diabetes.

In another aspect 86 the invention provides a compound according to any one of the aspects above which is an activator of glucokinase, when tested in the Glucokinase Activation Assay (I) disclosed herein at a glucose concentration of 2 mM.

In another aspect 87 the invention provides a compound according to any one of the aspects above which is an activator of glucokinase, when tested in the Glucokinase Activation Assay (I) disclosed herein at a glucose concentration of from 10 to 15 mM.

In another aspect 88 the invention provides a compound according to any one of the aspects above which, at a concentration of 30 µM, is capable of providing an at least 1.5, such as at least 1.7, for instance at least 2.0 fold activation of glucokinase in the Glucokinase Activation Assay (I) disclosed herein at a glucose concentration of 2 mM.

In another aspect 89 the invention provides a compound according to any one of the aspects above which, at a concentration of 30 µM, is capable of providing an at least 1.5, such as at least 1.7, for instance at least 2.0 fold activation of glucokinase in the Glucokinase Activation Assay (I) disclosed herein at a glucose concentration of from 10 to 15 mM.

In another aspect 90 the invention provides a compound according to any one of the aspects above which, at a concentration of 5 µM is capable of providing an at least 1.5, such as at least 1.7, for instance at least 2.0 fold activation of glucokinase in the Glucokinase Activation Assay (I) disclosed herein at a glucose concentration of 2 mM.

In another aspect 91 the invention provides a compound according to any one of the aspects above which, at a concentration of 5 µM is capable of providing an at least 1.5, such as at least 1.7, for instance at least 2.0 fold activation of glucokinase in the Glucokinase Activation Assay (I) disclosed herein at a glucose concentration of from 10 to 15 mM.

In another aspect 92 the invention provides a compound according to any one of the aspects above which provides an increase in glucokinase activity, where the increase in glucokinase activity provided by the compound increases with increasing concentrations of glucose.

In another aspect 93 the invention provides a compound according to any one of the aspects above which provides an increase in glucokinase activity in Glucokinase Activation Assay (I) disclosed herein at a glucose concentration of 15 mM, which increase is significantly higher than the increase in glucokinase activity provided by the compound in Glucokinase Activation Assay (I) disclosed herein at a glucose concentration of 5 mM.

In another aspect 94 the invention provides a compound according to any one of the aspects above which, at a compound concentration of 10 µM provides an increase in glucokinase activity in Glucokinase Activation Assay (I) disclosed herein at a glucose concentration of 15 mM, which increase is significantly higher than the increase in glucokinase activity provided by the compound at a compound concentration of 10 µM in Glucokinase Activation Assay (I) disclosed herein at a glucose concentration of 5 mM.

In another aspect 95 the invention provides a compound according to any one of the aspects above which, at a compound concentration of 10 µM provides an increase in glucokinase activity in Glucokinase Activation Assay (I) disclosed herein at a glucose concentration of 15 mM, which increase is at least 1.1 fold higher, such as at least 1.2 fold higher, for instance at least 1.3 fold higher, such as at least 1.4 fold higher, for instance 1.5 fold higher, such as at least 1.6 fold higher, for instance at least 1.7 fold higher, such as at least 1.8 fold higher, for instance at least 1.9 fold higher, such as at least 2.0 fold higher than the increase in glucokinase activity provided by the compound at a compound concentration of 10 µM in Glucokinase Activation Assay (I) disclosed herein at a glucose concentration of 5 mM.

In another aspect 96 the invention provides a compound according to any one of the aspects above which compound increases glucose utilization in the liver without inducing any increase in insulin secretion in response to glucose.

In another aspect 97 the invention provides a compound according to any one of the aspects above which compound shows a significantly higher activity in isolated hepatocytes compared to the activity of the compound in Ins-1 cells.

In another aspect 98 the invention provides a compound according to any one of the aspects above which compound shows a significantly higher activity in isolated hepatocytes measured as described in the Glucokinase Activity Assay (II) compared to the activity of the compound in Ins-1 cells measured as described in the Glucokinase Activity Assay (III).

In another aspect 99 the invention provides a compound according to any one of the aspects above which compound shows an activity in isolated hepatocytes measured as described in the Glucokinase Activity Assay (II) which activity is at least 1.1 fold higher, such as at least 1.2 fold higher, for instance at least 1.3 fold higher, such as at least 1.4 fold higher, for instance 1.5 fold higher, such as at least 1.6 fold higher, for instance at least 1.7 fold higher, such as at least 1.8 fold higher, for instance at least 1.9 fold higher, such as at least 2.0 fold higher, for instance at least a 3.0 fold higher, such as at least a 4.0 fold higher, for instance at least 5.0 fold higher, such as at least 10 fold higher than the activity of the compound in Ins-1 cells measured as described in the Glucokinase Activity Assay (III).

In another aspect 100 the invention provides a compound according to any one of the aspects above which compound shows no activity in the Ins-1 cells measured as described in the Glucokinase Activity Assay (III).

In an aspect 101 according to any one of the aspects above the invention provides a method of treating a disease or medical condition mediated through glucokinase comprising administering to an individual a pharmaceutically effective amount of a compound according to any one of the aspects above, wherein the disease or condition is a metabolic disorder, blood glucose lowering, hyperglycemia, impaired glucose tolerance (IGT), Syndrome X, Polycystic Ovarian Syndrome, impaired fasting glucose (IFG), type 1 diabetes, type 2 diabetes, delaying the progression of impaired glucose tolerance (IGT) to type 2 diabetes, delaying the progression of non-insulin requiring type 2 diabetes to insulin requiring type 2 diabetes, dyslipidemia, hyperlipidemia, hypertension, treatment or prophylaxis of obesity, lowering of food intake, appetite regulation, regulating feeding behaviour, and enhancing the secretion of enteroincretins.

Aspect 102. The method according to aspect 101 wherein the disease or medical disorder is type 1 diabetes.

Aspect 103. The method according to aspect 101 wherein the disease or medical disorder is type 2 diabetes.

In the structural formulae given herein and throughout the present specification, the terms below have the indicated meaning:

The term "halogen" or "halo" means fluorine, chlorine, bromine or iodine.

The term "hydroxy" shall mean the radical —OH.
The term "oxy" shall mean the radical —O—.
The term "oxo" shall mean the radical =O.
The term "carbonyl" shall mean the radical —C(=O)—.
The term "formyl" shall mean the radical —C(=O)H
The term "mercapto" shall mean the radical —SH.
The term "sulfanyl" shall mean the radical —S—.
The term "thioxo" shall mean the radical =S.
The term "sulfinyl" shall mean the radical —S(=O)—.
The term "sulfonyl" shall mean the radical —S(=O)$_2$—.
The term "sulfo" shall mean the radical —S(=O)$_2$OH
The term "sulfamoyl" shall mean the radical —S(=O)$_2$NH$_2$
The term "carboxy" shall mean the radical —(C=O)OH.
The term "amino" shall mean the radical —NH$_2$.
The term "nitro" shall mean the radical —NO$_2$.
The term "cyano" shall mean the radical —CN.

The term "bridge" as used herein represents a connection in a saturated or partly saturated ring between two atoms of such ring that are not neighbors through a chain of 1 to 6 atoms selected from carbon, nitrogen, oxygen and sulfur. Representative examples of such connecting chains are —CH$_2$—, —CH$_2$CH$_2$—, —CH$_2$NHCH$_2$—, —CH$_2$CH$_2$CH$_2$—, —CH$_2$OCH$_2$—, and the like.

The term "adjacent" as used herein regards the relative position of two atoms or variables, these two atoms are variables sharing a bond or one variable preceding or succeeding the other in a variable specification. By way of example, "atom A adjacent to atom B" means that the two atoms A and B share a bond.

The term "spiro atom" as used herein represents a carbon atom in a saturated or partly saturated ring that connects both ends of a chain of 3 to 6 atoms selected from carbon, nitrogen, oxygen and sulfur. Representative examples are —(CH$_2$)$_5$—, —(CH$_2$)$_3$—, —(CH$_2$)$_4$—, —CH$_2$NHCH$_2$CH$_2$—, —CH$_2$CH$_2$NHCH$_2$CH$_2$—, —CH$_2$NHCH$_2$CH$_2$CH$_2$—, —CH$_2$CH$_2$OCH$_2$—, —OCH$_2$CH$_2$O— and the like.

The term "$C_{1-6}$-alkyl" as used herein represents a saturated, branched or straight hydrocarbon group having from 1 to 6 carbon atoms. Representative examples are methyl, ethyl, propyl (e.g. prop-1-yl, prop-2-yl (or iso-propyl)), butyl (e.g. 2-methylprop-2-yl (or tert-butyl), but-1-yl, but-2-yl), pentyl (e.g. pent-1-yl, pent-2-yl, pent-3-yl), 2-methylbut-1-yl, 3-methylbut-1-yl, hexyl (e.g. hex-1-yl), and the like.

The term "$C_{2-6}$-alkenyl" as used herein represents a branched or straight hydrocarbon group having from 2 to 6 carbon atoms and at least one double bond. Representative examples are ethenyl (or vinyl), propenyl (e.g. prop-1-enyl, prop-2-enyl), butadienyl (e.g. buta-1,3-dienyl), butenyl (e.g. but-1-en-1-yl, but-2-en-1-yl), pentenyl (e.g. pent-1-en-1-yl, pent-2-en-2-yl), hexenyl (e.g. hex-1-en-2-yl, hex-2-en-1-yl), 1-ethylprop-2-enyl, 1,1-(dimethyl)prop-2-enyl, 1-ethylbut-3-enyl, 1,1-(dimethyl)but-2-enyl, and the like.

The term "$C_{2-6}$-alkynyl" as used herein represents a branched or straight hydrocarbon group having from 2 to 6 carbon atoms and at least one triple bond. Representative examples are ethynyl, propynyl (e.g. prop-1-ynyl, prop-2-ynyl), butynyl (e.g. but-1-ynyl, but-2-ynyl), pentynyl (e.g. pent-1-ynyl, pent-2-ynyl), hexynyl (e.g. hex-1-ynyl, hex-2-ynyl), 1-ethylprop-2-ynyl, 1,1-(dimethyl)prop-2-ynyl, 1-ethylbut-3-ynyl, 1,1-(dimethyl)but-2-ynyl, and the like.

The term "$C_{3-10}$-cycloalkyl" as used herein represents a saturated monocyclic carbocyclic ring having from 3 to 10 carbon atoms. Representative examples are cyclopropyl, cyclobutyl, cyclopentyl, cyclohexyl, cycloheptyl, cyclooctyl, and the like. $C_{3-10}$-cycloalkyl is also intended to represent a saturated bicyclic carbocyclic ring having from 4 to 10 carbon atoms. Representative examples are decahydronaphthalenyl, bicyclo[3.3.0]octanyl, and the like. $C_{3-10}$-cycloalkyl is also intended to represent a saturated carbocyclic ring having from 3 to 10 carbon atoms and containing one or two carbon bridges. Representative examples are adamantyl, norbornanyl, nortricyclyl, bicyclo[3.2.1]octanyl, bicyclo[2.2.2]octanyl, tricyclo[5.2.1.0/2.6]decanyl, bicyclo[2.2.1]heptyl, and the like. $C_{3-10}$-cycloalkyl is also intended to represent a saturated carbocyclic ring having from 3 to 10 carbon atoms and containing one or more spiro atoms. Representative examples are spiro[2.5]octanyl, spiro[4.5]decanyl, and the like.

The term "$C_{3-8}$-cycloalkenyl" as used herein represents a partially saturated monocyclic carbocyclic ring having from 3 to 8 carbon atoms and at least one double bond. Representative examples are cyclopropenyl, cyclobutenyl, cyclopentenyl, cyclohexenyl, cycloheptenyl, cyclooctenyl, cyclohex-1,3-dienyl, and the like.

The term "aryl" as used herein is intended to include monocyclic, bicyclic or polycyclic carbocyclic aromatic rings. Representative examples are phenyl, naphthyl (e.g. naphth-1-yl, naphth-2-yl), anthryl (e.g. anthr-1-yl, anthr-9-yl), phenanthryl (e.g. phenanthr-1-yl, phenanthr-9-yl), and the like. Aryl is also intended to include monocyclic, bicyclic or polycyclic carbocyclic aromatic rings substituted with carbocyclic aromatic rings. Representative examples are biphenyl (e.g. biphenyl-2-yl, biphenyl-3-yl, biphenyl-4-yl), phenylnaphthyl (e.g. 1-phenylnaphth-2-yl, 2-phenylnaphth-1-yl), and the like. Aryl is also intended to include partially saturated bicyclic or polycyclic carbocyclic rings with at least one unsaturated moiety (e.g. a benzo moiety). Representative examples are, indanyl (e.g. indan-1-yl, indan-5-yl), indenyl (e.g. inden-1-yl, inden-5-yl), 1,2,3,4-tetrahydronaphthyl (e.g. 1,2,3,4-tetrahydronaphth-1-yl, 1,2,3,4-tetrahydronaphth-2-yl, 1,2,3,4-tetrahydronaphth-6-yl), 1,2-dihydronaphthyl (e.g. 1,2-dihydronaphth-1-yl, 1,2-dihydronaphth-4-yl, 1,2-dihydronaphth-6-yl), fluorenyl (e.g. fluoren-1-yl, fluoren-4-yl, fluoren-9-yl), and the like. Aryl is also intended to include partially saturated bicyclic or polycyclic carbocyclic aromatic rings containing one or two bridges. Representative examples are, benzonorbornyl (e.g. benzonorborn-3-yl, benzonorborn-6-yl), 1,4-ethano-1,2,3,4-tetrahydronapthyl (e.g. 1,4-ethano-1,2,3,4-tetrahydronapth-2-yl, 1,4-ethano-1,2,3,4-tetrahydronapth-10-yl), and the like. Aryl is also intended to include partially saturated bicyclic or polycyclic carbocyclic aromatic rings containing one or more spiro atoms. Representative examples are spiro[cyclopentane-1,1'-indane]-4-yl, spiro[cyclopentane-1,1'-indene]-4-yl, spiro[piperidine-4,1'-indane]-1-yl, spiro[piperidine-3,2'-indane]-1-yl, spiro[piperidine-4,2'-indane]-1-yl, spiro[piperidine-4,1'-indane]-3'-yl, spiro[pyrrolidine-3,2'-indane]-1-yl, spiro[pyrrolidine-3,1'-(3',4'-dihydronaphthalene)]-1-yl, spiro[piperidine-3,1'-(3',4'-dihydronaphthalene)]-1-yl, spiro[piperidine-4,1'-(3',4'-dihydronaphthalene)]-1-yl, spiro[imidazolidine-4,2'-indane]-1-yl, spiro[piperidine-4,1'-indene]-1-yl, and the like.

The term "heterocyclyl" as used herein represents a saturated 3 to 10 membered monocyclic ring, containing one or more heteroatoms selected from nitrogen, oxygen, sulfur, S(=O) and S(=O)$_2$. Representative examples are aziridinyl (e.g. aziridin-1-yl), azetidinyl (e.g. azetidin-1-yl, azetidin-3-yl), oxetanyl, pyrrolidinyl (e.g. pyrrolidin-1-yl, pyrrolidin-2-yl, pyrrolidin-3-yl), imidazolidinyl (e.g. imidazolidin-1-yl, imidazolidin-2-yl, imidazolidin-4-yl), oxazolidinyl (e.g. oxazolidin-2-yl, oxazolidin-3-yl, oxazolidin-4-yl), thiazolidinyl (e.g. thiazolidin-2-yl, thiazolidin-3-yl, thiazolidin-4-yl), isothiazolidinyl, piperidinyl (e.g. piperidin-1-yl, piperidin-2-yl, piperidin-3-yl, piperidin-4-yl), homopiperidinyl (e.g. homopiperidin-1-yl, homopiperidin-2-yl, homopiperidin-3-yl, homopiperidin-4-yl), piperazinyl (e.g. piperazin-1-yl, piperazin-2-yl), morpholinyl (e.g. morpholin-2-yl, morpholin-3-yl, morpholin-4-yl), thiomorpholinyl (e.g. thiomorpholin-2-yl, thiomorpholin-3-yl, thiomorpholin-4-yl), 1-oxo-thiomorpholinyl, 1,1-dioxo-thiomorpholinyl, tetrahydrofuranyl (e.g. tetrahydrofuran-2-yl, tetrahydrofuran-3-yl), tetrahydrothienyl, tetrahydro-1,1-dioxothienyl, tetrahydropyranyl (e.g. 2-tetrahydropyranyl), tetrahydrothiopyranyl (e.g. 2-tetrahydrothiopyranyl), 1,4-dioxanyl, 1,3-dioxanyl, and the like. Heterocyclyl is also intended to represent a saturated 6 to 10 membered bicyclic ring containing one or more heteroatoms selected from nitrogen, oxygen, sulfur, S(=O) and S(=O)$_2$. Representative examples are octahydroindolyl (e.g. octahydroindol-1-yl, octahydroindol-2-yl, octahydroindol-3-yl, octahydroindol-5-yl), decahydroquinolinyl (e.g. decahydroquinolin-1-yl, decahydroquinolin-2-yl, decahydroquinolin-3-yl, decahydroquinolin-4-yl, decahydroquinolin-6-yl), decahydroquinoxalinyl (e.g. decahydroquinoxalin-1-yl, decahydroquinoxalin-2-yl, decahydroquinoxalin-6-yl) and the like. Heterocyclyl is also intended to represent a saturated 6 to 10 membered ring containing one or more heteroatoms selected from nitrogen, oxygen, sulfur, S(=O) and S(=O)$_2$ and having one or two bridges. Representative examples are 3-azabicyclo[3.2.2]nonyl, 2-azabicyclo[2.2.1]heptyl, 3-azabicyclo[3.1.0]hexyl, 2,5-diazabicyclo[2.2.1]heptyl, atropinyl, tropinyl, quinuclidinyl, 1,4-diazabicyclo[2.2.2]octanyl, and the like. Heterocyclyl is also intended to represent a 6 to 10 membered saturated ring containing one or more heteroatoms selected from nitrogen, oxygen, sulfur, S(=O) and S(=O)$_2$ and containing one or more spiro atoms. Representative examples are 1,4-dioxaspiro[4.5]decanyl (e.g. 1,4-dioxaspiro[4.5]decan-2-yl, 1,4-dioxaspiro[4.5]decan-7-yl), 1,4-dioxa-8-azaspiro[4.5]decanyl (e.g. 1,4-dioxa-8-azaspiro[4.5]decan-2-yl, 1,4-dioxa-8-azaspiro[4.5]decan-8-yl), 8-azaspiro[4.5]decanyl (e.g. 8-azaspiro[4.5]decan-1-yl, 8-azaspiro[4.5]decan-8-yl), 2-azaspiro[5.5]undecanyl (e.g. 2-azaspiro[5.5]undecan-2-yl), 2,8-diazaspiro[4.5]decanyl (e.g. 2,8-diazaspiro[4.5]decan-2-yl, 2,8-diazaspiro[4.5]decan-8-yl), 2,8-diazaspiro[5.5]undecanyl (e.g. 2,8-diazaspiro[5.5]undecan-2-yl), 1,3,8-triazaspiro[4.5]decanyl (e.g. 1,3,8-triazaspiro[4.5]decan-1-yl, 1,3,8-triazaspiro[4.5]decan-3-yl, 1,3,8-triazaspiro[4.5]decan-8-yl), and the like.

The term "heteroaryl" as used herein is intended to include monocyclic heterocyclic aromatic rings containing one or more heteroatoms selected from nitrogen, oxygen, sulfur, SO and S(=O)$_2$. Representative examples are pyrrolyl (e.g. pyrrol-1-yl, pyrrol-2-yl, pyrrol-3-yl), furanyl (e.g. furan-2-yl, furan-3-yl), thienyl (e.g. thien-2-yl, thien-3-yl), oxazolyl (e.g. oxazol-2-yl, oxazol-4-yl, oxazol-5-yl), thiazolyl (e.g. thiazol-2-yl, thiazol-4-yl, thiazol-5-yl), imidazolyl (e.g. imidazol-2-yl, imidazol-4-yl, imidazol-5-yl), pyrazolyl (e.g.

pyrazol-1-yl, pyrazol-3-yl, pyrazol-5-yl), isoxazolyl (e.g. isoxazol-3-yl, isoxazol-4-yl, isoxazol-5-yl), isothiazolyl (e.g. isothiazol-3-yl, isothiazol-4-yl, isothiazol-5-yl), 1,2,3-triazolyl (e.g. 1,2,3-triazol-1-yl, 1,2,3-triazol-4-yl, 1,2,3-triazol-5-yl), 1,2,4-triazolyl (e.g. 1,2,4-triazol-1-yl, 1,2,4-triazol-3-yl, 1,2,4-triazol-5-yl), 1,2,3-oxadiazolyl (e.g. 1,2,3-oxadiazol-4-yl, 1,2,3-oxadiazol-5-yl), 1,2,4-oxadiazolyl (e.g. 1,2,4-oxadiazol-3-yl, 1,2,4-oxadiazol-5-yl), 1,2,5-oxadiazolyl (e.g. 1,2,5-oxadiazol-3-yl, 1,2,5-oxadiazol-4-yl), 1,3,4-oxadiazolyl (e.g. 1,3,4-oxadiazol-2-yl, 1,3,4-oxadiazol-5-yl), 1,2,3-thiadiazolyl (e.g. 1,2,3-thiadiazol-4-yl, 1,2,3-thiadiazol-5-yl), 1,2,4-thiadiazolyl (e.g. 1,2,4-thiadiazol-3-yl, 1,2,4-thiadiazol-5-yl), 1,2,5-thiadiazolyl (e.g. 1,2,5-thiadiazol-3-yl, 1,2,5-thiadiazol-4-yl), 1,3,4-thiadiazolyl (e.g. 1,3,4-thiadiazol-2-yl, 1,3,4-thiadiazol-5-yl), tetrazolyl (e.g. tetrazol-1-yl, tetrazol-5-yl), pyranyl (e.g. pyran-2-yl), pyridinyl (e.g. pyridine-2-yl, pyridine-3-yl, pyridine-4-yl), pyridazinyl (e.g. pyridazin-2-yl, pyridazin-3-yl), pyrimidinyl (e.g. pyrimidin-2-yl, pyrimidin-4-yl, pyrimidin-5-yl), pyrazinyl, 1,2,3-triazinyl, 1,2,4-triazinyl, 1,3,5-triazinyl, thiadiazinyl, azepinyl, azecinyl, and the like. Heteroaryl is also intended to include bicyclic heterocyclic aromatic rings containing one or more heteroatoms selected from nitrogen, oxygen, sulfur, S(=O) and S(=O)$_2$. Representative examples are indolyl (e.g. indol-1-yl, indol-2-yl, indol-3-yl, indol-5-yl), isoindolyl, benzofuranyl (e.g. benzo[b]furan-2-yl, benzo[b]furan-3-yl, benzo[b]furan-5-yl, benzo[c]furan-2-yl, benzo[c]furan-3-yl, benzo[c]furan-5-yl), benzothienyl (e.g. benzo[b]thien-2-yl, benzo[b]thien-3-yl, benzo[b]thien-5-yl, benzo[c]thien-2-yl, benzo[c]thien-3-yl, benzo[c]thien-5-yl), indazolyl (e.g. indazol-1-yl, indazol-3-yl, indazol-5-yl), indolizinyl (e.g. indolizin-1-yl, indolizin-3-yl), benzopyranyl (e.g. benzo[b]pyran-3-yl, benzo[b]pyran-6-yl, benzo[c]pyran-1-yl, benzo[c]pyran-7-yl), benzimidazolyl (e.g. benzimidazol-1-yl, benzimidazol-2-yl, benzimidazol-5-yl), benzothiazolyl (e.g. benzothiazol-2-yl, benzothiazol-5-yl), benzisothiazolyl, benzoxazolyl, benzisoxazolyl, benzoxazinyl, benzotriazolyl, naphthyridinyl (e.g. 1,8-naphthyridin-2-yl, 1,7-naphthyridin-2-yl, 1,6-naphthyridin-2-yl), phthalazinyl (e.g. phthalazin-1-yl, phthalazin-5-yl), pteridinyl, purinyl (e.g. purin-2-yl, purin-6-yl, purin-7-yl, purin-8-yl, purin-9-yl), quinazolinyl (e.g. quinazolin-2-yl, quinazolin-4-yl, quinazolin-6-yl), cinnolinyl, quinoliny (e.g. quinolin-2-yl, quinolin-3-yl, quinolin-4-yl, quinolin-6-yl), isoquinolinyl (e.g. isoquinolin-1-yl, isoquinolin-3-yl, isoquinolin-4-yl), quinoxalinyl (e.g. quinoxalin-2-yl, quinoxalin-5-yl), pyrrolopyridinyl (e.g. pyrrolo[2,3-b]pyridinyl, pyrrolo[2,3-c]pyridinyl, pyrrolo[3,2-c]pyridinyl), furopyridinyl (e.g. furo[2,3-b]pyridinyl, furo[2,3-c]pyridinyl, furo[3,2-c]pyridinyl), thienopyridinyl (e.g. thieno[2,3-b]pyridinyl, thieno[2,3-c]pyridinyl, thieno[3,2-c]pyridinyl), imidazopyridinyl (e.g. imidazo[4,5-b]pyridinyl, imidazo[4,5-c]pyridinyl, imidazo[1,5-a]pyridinyl, imidazo[1,2-a]pyridinyl), imidazopyrimidinyl (e.g. imidazo[1,2-a]pyrimidinyl, imidazo[3,4-a]pyrimidinyl), pyrazolopyridinyl (e.g. pyrazolo[3,4-b]pyridinyl, pyrazolo[3,4-c]pyridinyl, pyrazolo[1,5-a]pyridinyl), pyrazolopyrimidinyl (e.g. pyrazolo[1,5-a]pyrimidinyl, pyrazolo[3,4-d]pyrimidinyl), thiazolopyridinyl (e.g. thiazolo[3,2-d]pyridinyl), thiazolopyrimidinyl (e.g. thiazolo[5,4-d]pyrimidinyl), imidazothiazolyl (e.g. imidazo[2,1-b]thiazolyl), triazolopyridinyl (e.g. triazolo[4,5-b]pyridinyl), triazolopyrimidinyl (e.g. 8-azapurinyl), and the like. Heteroaryl is also intended to include polycyclic heterocyclic aromatic rings containing one or more heteroatoms selected from nitrogen, oxygen, sulfur, S(=O) and S(=O)$_2$. Representative examples are carbazolyl (e.g. carbazol-2-yl, carbazol-3-yl, carbazol-9-yl), phenoxazinyl (e.g. phenoxazin-10-yl), phenazinyl (e.g. phenazin-5-yl), acridinyl (e.g. acridin-9-yl, acridin-10-yl), phenothiazinyl (e.g. phenothiazin-10-yl), carbolinyl (e.g. pyrido[3,4-b]indol-1-yl, pyrido[3,4-b]indol-3-yl), phenanthrolinyl (e.g. phenanthrolin-5-yl), and the like. Heteroaryl is also intended to include partially saturated monocyclic, bicyclic or polycyclic heterocyclic rings containing one or more heteroatoms selected from nitrogen, oxygen, sulfur, S(=O) and S(=O)$_2$. Representative examples are pyrrolinyl, pyrazolinyl, imidazolinyl (e.g. 4,5-dihydroimidazol-2-yl, 4,5-dihydroimidazol-1-yl), indolinyl (e.g. 2,3-dihydroindol-1-yl, 2,3-dihydroindol-5-yl), isoindolinyl (e.g. 2,3-dihydroisoindol-2-yl), dihydrobenzofuranyl (e.g. 2,3-dihydrobenzo[b]furan-2-yl, 2,3-dihydrobenzo[b]furan-4-yl), dihydrobenzothienyl (e.g. 2,3-dihydrobenzo[b]thien-2-yl, 2,3-dihydrobenzo[b]thien-5-yl), 4,5,6,7-tetrahydrobenzo[b]furan-5-yl), dihydrobenzopyranyl (e.g. 3,4-dihydrobenzo[b]pyran-3-yl, 3,4-dihydrobenzo[b]pyran-6-yl, 3,4-dihydrobenzo[c]pyran-1-yl, dihydrobenzo[c]pyran-7-yl), oxazolinyl (e.g. 4,5-dihydrooxazol-2-yl, 4,5-dihydrooxazol-4-yl, 4,5-dihydrooxazol-5-yl), isoxazolinyl, oxazepinyl, tetrahydroindazolyl (e.g. 4,5,6,7-tetrahydroindazol-1-yl, 4,5,6,7-tetrahydroindazol-3-yl, 4,5,6,7-tetrahydroindazol-4-yl, 4,5,6,7-tetrahydroindazol-6-yl), tetrahydrobenzimidazolyl (e.g. 4,5,6,7-tetrahydrobenzimidazol-1-yl, 4,5,6,7-tetrahydrobenzimidazol-5-yl), tetrahydroimidazo[4,5-c]pyridyl (e.g. 4,5,6,7-tetrahydroimidazo[4,5-c]pyrid-1-yl, 4,5,6,7-tetrahydroimidazo[4,5-c]pyrid-5-yl, 4,5,6,7-tetrahydroimidazo[4,5-c]pyrid-6-yl), tetrahydroquinolinyl (e.g. 1,2,3,4-tetrahydroquinolinyl, 5,6,7,8-tetrahydroquinolinyl), tetrahydroisoquinolinyl (e.g. 1,2,3,4-tetrahydroisoquinolinyl, 5,6,7,8-tetrahydroisoquinolinyl), tetrahydroquinoxalinyl (e.g. 1,2,3,4-tetrahydroquinoxalinyl, 5,6,7,8-tetrahydroquinoxalinyl), and the like. Heteroaryl is also intended to include partially saturated bicyclic or polycyclic heterocyclic rings containing one or more spiro atoms. Representative examples are spiro[isoquinoline-3,1'-cyclohexan]-1-yl, spiro[piperidine-4,1'-benzo[c]thiophen]-1-yl, spiro[piperidine-4,1'-benzo[c]furan]-1-yl, spiro[piperidine-4,3'-benzo[b]furan]-1-yl, spiro[piperidine-4,3'-coumarin]-1-yl, and the like.

The term "optionally substituted" as used herein means that the groups in question are either unsubstituted or substituted with one or more of the substituents specified. When the group(s) in question are substituted with more than one substituent the substituents may be the same or different.

Certain of the defined terms may occur more than once in the structural formulae, and upon such occurrence each term shall be defined independently of the other.

Certain of the defined terms may occur in combinations, and it is to be understood that the first mentioned radical is a substituent on the subsequently mentioned radical, where the point of substitution, i.e. the point of attachment to another part of the molecule, is on the last mentioned of the radicals. Such combinations of terms include for example "halo-$C_{1-6}$-alkyl" as used herein refers to $C_{1-6}$-alkyl, substituted one or more times at any carbon atom(s) with any halogen. Representative examples are trifluoromethyl, 2,2,2-trifluoroethyl, and the like.

"hydroxy-$C_{1-6}$-alkyl" as used herein refers to $C_{1-6}$-alkyl substituted one or more times at any carbon atom(s) with hydroxyl. Representative examples are hydroxymethyl, hydroxyethyl (e.g. 1-hydroxyethyl, 2-hydroxyethyl), and the like.

"$C_{3-10}$-cycloalkyl-$C_{1-6}$-alkyl". Representative examples are cyclopropylmethyl, 2-cyclohexylethyl, 3-cyclopentyl-prop-1-yl, 1-cyclohexylethyl, adamantylmethyl, and the like.

"aryl-$C_{1-6}$-alkyl". Representative examples are benzyl, phenethyl (e.g. 1-phenylethyl, 2-phenylethyl), phenylpropyl (e.g. 1-phenylpropyl, 2-phenylpropyl), and the like.

"heteroaryl-$C_{1-6}$-alkyl". Representative examples are furan-2-ylmethyl, thien-3-ylmethyl, pyridin-4-ylmethyl, 1-methyl-1-(pyrimidin-2-yl)ethyl, and the like.

"aryl-$C_{2-6}$-alkenyl". Representative examples are 2-phenylethenyl, 3-phenylprop-2-en-1-yl, and the like.

"$C_{1-6}$-alkoxy" as used herein refers to the radical $C_{1-6}$-alkyl-O—. Representative examples are methoxy, ethoxy, propoxy (e.g. 1-propoxy, 2-propoxy), butoxy (e.g. 1-butoxy, 2-butoxy, 2-methyl-2-propoxy), pentoxy (1-pentoxy, 2-pentoxy), hexoxy (1-hexoxy, 3-hexoxy), and the like.

"halo-$C_{1-6}$-alkoxy" as used herein refers to $C_{1-6}$-alkoxy, substituted one or more times at any carbon atom(s) with any halogen. Representative examples are trifluoromethoxy and 2,2,2-trifluoroethoxy, and the like.

"$C_{1-6}$-alkoxy-$C_{1-6}$-alkyl". Representative examples are methoxymethyl, ethoxymethyl, 2-methoxyethyl, 2-ethoxyethyl, 3-methoxyprop-1-yl, and the like.

"aryloxy-$C_{1-6}$-alkyl". Representative examples are phenoxymethyl, phenoxyethyl (e.g. 1-phenoxyethyl, 2-phenoxyethyl), naphthyloxymethyl (e.g. napth-1-yloxy, napth-2-yloxy), biphenyllyloxymethyl (e.g. biphenyl-4-yloxymethyl, biphenyl-3-yloxymethyl, biphenyl-2-yloxymethyl), and the like.

"heteroaryloxy-$C_{1-6}$-alkyl". Representative examples are pyridin-2-yloxymethyl and 2-(quinolin-2-yloxy)ethyl, and the like.

"aryl-$C_{1-6}$-alkoxy-$C_{1-6}$-alkyl". Representative examples are 2-phenylethoxymethyl and (naphth-2-yl)methoxymethyl, and the like.

"heteroaryl-$C_{1-6}$-alkoxy-$C_{1-6}$-alkyl". Representative examples are pyrimidin-4-ylmethoxymethyl and quinolin-2-ylmethoxymethyl, and the like.

"$C_{3-8}$-cycloalkoxy" as used herein refers to the radical $C_{3-10}$-cycloalkyl-O—. Representative examples are cyclopropoxy, cyclobutoxy, cyclopentoxy, cyclohexoxy, and the like.

"aryl-$C_{1-6}$-alkoxy". Representative examples are benzyloxy, phenethoxy (e.g. 1-phenylethoxy, 2-phenylethoxy), phenylpropoxy (e.g. 3-phenyl-1-propoxy, 2-phenyl-1-propoxy), naphthylmethoxy (e.g. naphth-1-ylmethoxy, naphthyl-2-ylmethoxy), naphtylethoxy (e.g. 2-(naphth-1-yl)ethoxy, 1-(naphth-2-yl)ethoxy), biphenylylmethoxy (e.g. biphenyl-4-ylmethoxy, biphenyl-3-ylmethoxy, biphenyl-2-ylmethoxy), and the like.

"heteroaryl-$C_{1-6}$-alkoxy". Representative examples are pyridinylmethoxy (e.g. pyridin-2-ylmethoxy, pyridin-4-ylmethoxy), quinolinylethoxy (e.g. 2-(quinolin-2-yl)ethoxy, 1-(quinolin-2-yl)ethoxy), and the like.

"aryloxy" as used herein refers to the radical aryl-O—. Representative examples are phenoxy, naphthyloxy (e.g. naphth-1-yloxy, naphtha-2-yloxy), biphenylyloxy (e.g. biphenyl-4-yloxy, biphenyl-3-yloxy, biphenyl-2-yloxy), and the like.

"heteroaryloxy" as used herein refers to the radical heteroaryl-O—. Representative examples are pyrimidinyloxy (e.g. pyrimidin-2-yloxy, pyrimidin-5-yloxy), quinolinyloxy (e.g. quinolin-2-yloxy, quinolin-4-yloxy), isoquinolinyloxy, quinazolinyloxy, quinoxalinyloxy, indolyloxy (e.g. indol-2-yloxy, indol-3-yloxy), benzimidazolyloxy (e.g. benzimidazol-2-yloxy), benzofuranyloxy (e.g. benzo[b]furan-2-yloxy, benzo[b]furan-3-yloxy), and the like.

"$C_{1-6}$-alkylsulfanyl" as used herein refers to the radical $C_{1-6}$-alkyl-S—. Representative examples are methylthio, ethylthio, propylthio (e.g. 1-propylthio, 2-propylthio, 3-propylthio), butylthio, pentylthio, hexylthio, and the like.

"$C_{3-10}$-cycloalkylsulfanyl" as used herein refers to the radical $C_{3-10}$-cycloalkyl-S—. Representative examples are cyclopropylsulfanyl, cyclobutylsulfanyl, cyclopentylsulfanyl, cyclohexylsulfanyl, and the like.

"arylsulfanyl" as used herein refers to the radical aryl-S—. Representative examples are phenylsulfanyl, (4-methylphenyl)sulfanyl, (2-chlorophenyl)sulfanyl, and the like.

"$C_{1-6}$-alkylsulfinyl" as used herein refers to the radical $C_{1-6}$-alkyl-S(=O)—. Representative examples are methylsulfinyl, ethylsulfinyl, propylsulfinyl, butylsulfinyl, pentylsulfinyl, hexylsulfinyl, and the like.

"$C_{1-6}$-alkylsulfonyl" as used herein refers to the radical $C_{1-6}$-alkyl-S(=O)$_2$—. Representative examples are methylsulfonyl, ethylsulfonyl, propylsulfonyl, butylsulfonyl, pentylsulfonyl, hexylsulfonyl, and the like.

"arylsulfonyl" as used herein refers to the radical aryl-S(=O)$_2$—. Representative examples are phenylsulfonyl, (4-methylphenyl)sulfonyl, (4-chlorophenyl)sulfonyl, naphthylsulfonyl, and the like.

"$C_{1-6}$-alkylamino" as used herein refers to the radical $C_{1-6}$-alkyl-NH—. Representative examples are methylamino, ethylamino, propylamino (e.g. prop-1-ylamino, prop-2-ylamino, prop-3-ylamino), butylamino (e.g. but-1-ylamino, but-3-ylamino), pentylamino, hexylamino, heptylamino, and the like.

"$C_{3-10}$-cycloalkylamino" as used herein refers to the radical $C_{3-10}$-cycloalkyl-NH—. Representative examples are cyclopropylamino, cyclobutylamino, cyclopentylamino, cyclohexylamino and the like.

"di($C_{1-6}$-alkyl)amino" as used herein refers to the radical ($C_{1-6}$-alkyl)$_2$N—. Representative examples are N,N-dimethylamino, N-ethyl-N-methylamino, N,N-diethylamino, N,N-dipropylamino (e.g. N,N-(prop-1-yl)$_2$amino, N,N-(prop-2-yl)$_2$amino, N,N-(prop-3-yl)$_2$amino), N-(but-1-yl)-N-methylamino, N,N-(pent-1-yl)$_2$amino, and the like.

"$C_{1-6}$-alkylsulfinamoyl", as used herein refers to the radical $C_{1-6}$-alkyl-NHS(=O)—. Representative examples are methylsulfinamoyl, ethylsulfinamoyl, propylsulfinamoyl, and the like.

"di($C_{1-6}$-alkyl)sulfinamoyl", as used herein refers to the radical ($C_{1-6}$-alkyl)$_2$NS(=O)—. Representative examples are dimethylsulfinamoyl, diethylsulfinamoyl, and the like.

"$C_{1-6}$-alkylsulfamoyl", as used herein refers to the radical $C_{1-6}$-alkyl-NHS(=O)$_2$—. Representative examples are methylsulfamoyl, ethylsulfamoyl, propylsulfamoyl, and the like.

"di($C_{1-6}$-alkyl)sulfamoyl", as used herein refers to the radical ($C_{1-6}$-alkyl)$_2$NS(=O)$_2$—. Representative examples are dimethylsulfamoyl, diethylsulfamoyl, and the like.

"$C_{1-6}$-alkylcarbonyl" as used herein refers to the radical $C_{1-6}$-alkyl-C(=O)—. Representative examples are acetyl (methylcarbonyl), propionyl (ethylcarbonyl), butanoyl (prop-1-ylcarbonyl, prop-2-ylcarbonyl), and the like.

"$C_{3-10}$-cycloalkylcarbonyl" as used herein refers to the radical $C_{3-10}$-cycloalkyl-C(=O)—. Representative examples are cyclopropylcarbonyl, cyclopentylcarbonyl, cyclohexylcarbonyl, and the like.

"arylcarbonyl" as used herein refers to the radical aryl-C(=O)—. Representative examples are benzoyl, naphthylcarbonyl, 4-phenylbenzoyl, anthrylcarbonyl, phenanthrylcarbonyl, and the like.

"heteroarylcarbonyl" as used herein refers to the radical heteroaryl-C(=O)—. Representative examples are pyridinylcarbonyl (e.g. pyridin-2-ylcarbonyl, pyridin-4-ylcarbonyl), quinolinylcarbonyl (e.g. 2-(quinolin-2-yl)carbonyl, 1-(quinolin-2-yl)carbonyl), imidazolylcarbonyl (e.g. imidazol-2-ylcarbonyl, imidazol-5-ylcarbonyl), and the like.

"heterocyclylcarbonyl" as used herein refers to the radical heterocyclyl-C(=O)—. Representative examples are piperidinylcarbonyl (e.g. piperidin-2-ylcarbonyl, piperidin-3-ylcarbonyl, piperidin-4-ylcarbonyl), piperazinylcarbonyl (e.g. piperazin-1-ylcarbonyl, piperazin-2-ylcarbonyl), and the like.

"$C_{1-6}$-alkylcarbonyl-$C_{1-6}$-alkyl" as used herein refers to the radical $C_{1-6}$-alkyl-C(=O)—$C_{1-6}$-alkyl. Representative examples are 2-oxoprop-1-yl and 4,4-dimethyl-2-oxopent-1-yl, and the like.

"arylcarbonyl-$C_{1-6}$-alkyl" as used herein refers to the radical aryl-C(=O)—$C_{1-6}$-alkyl. Representative examples are benzoylmethyl, naphthylcarbonylmethyl, 4-phenylbenzoylmethyl, benzoylethyl, benzoylpropyl, and the like.

"heteroarylcarbonyl-$C_{1-6}$-alkyl" as used herein refers to the radical heteroaryl-C(=O)—$C_{1-6}$-alkyl. Representative examples are 2-(pyridin-2-yl)-2-oxoethyl and 3-(imidazol-2-yl)-3-oxoprop-1-yl, and the like.

"aryl-$C_{1-6}$-alkylcarbonyl" as used herein refers to the radical aryl-$C_{1-6}$-alkyl-C(=O)—. Representative examples are phenylpropylcarbonyl (e.g. (3-phenylprop-1-yl)carbonyl, (2-phenylprop-1-yl)carbonyl), phenylethylcarbonyl (e.g. 2-phenylethylcarbonyl, 1-phenylethylcarbonyl), and the like.

"heteroaryl-$C_{1-6}$-alkylcarbonyl" as used herein refers to the radical heteroaryl-$C_{1-6}$-alkyl-C(=O)—. Representative examples are furanylmethylcarbonyl, thienylmethylcarbonyl, pyridinylmethylcarbonyl, pyridinylethylcarbonyl, 1-methyl-1-(pyrimidinyl)ethylcarbonyl, and the like.

"$C_{1-6}$-alkoxycarbonyl" as used herein refers to the radical $C_{1-6}$-alkoxy-C(=O)—. Representative examples are methoxycarbonyl, ethoxycarbonyl, 1-propoxycarbonyl, 2-propoxycarbonyl, 1-butoxycarbonyl, 2-butoxycarbonyl, 2-methyl-2-propoxycarbonyl, 3-methylbutoxycarbonyl, 1-hexoxycarbonyl, and the like.

"aryloxycarbonyl" as used herein refers to the radical aryloxy-C(=O)—. Representative examples are phenoxycarbonyl, naphthyloxycarbonyl, 4-biphenylyloxycarbonyl, and the like.

"aryl-$C_{1-6}$-alkoxycarbonyl" as used herein refers to the radical aryl-$C_{1-6}$-alkoxy-C(=O)—Representative examples are benzyloxycarbonyl, phenylethoxycarbonyl (e.g. (2-phenylethoxy)carbonyl, (1-phenylethoxy)carbonyl), and the like.

"$C_{1-6}$-alkylcarboxy" as used herein refers to the radical $C_{1-6}$-alkyl-C(=O)O—. Representative examples are methylcarboxy, ethylcarboxy, propylcarboxy (e.g. prop-1-ylcarboxy, prop-2-ylcarboxy), and the like.

"arylcarboxy" as used herein refers to the radical aryl-C(=O)O—. Representative examples are benzoyloxy, naphthylcarboxy, 4-biphenylylcarboxy, and the like.

"heteroarylcarboxy" as used herein refers to the radical heteroaryl-C(=O)O—. Representative examples are pyridinylcarboxy and (imidazol-2-yl)carboxy, and the like.

"$C_{1-6}$-alkylcarboxy-$C_{1-6}$-alkyl" as used herein refers to the radical $C_{1-6}$-alkyl-C(=O)O—$C_{1-6}$-alkyl. Representative examples are ethylcarboxymethyl, propylcarboxybutyl, pentylcarboxyethyl, and the like.

"aryl-$C_{1-6}$-alkylcarboxy" as used herein refers to the radical aryl-$C_{1-6}$-alkyl-C(=O)O—. Representative examples are benzylcarboxy and phenylpropylcarboxy, and the like.

"heteroaryl-$C_{1-6}$-alkylcarboxy" as used herein refers to the radical heteroaryl-$C_{1-6}$-alkyl-C(=O)O—. Representative examples are (imidazol-2-yl)acetoxy and (pyrimidin-2-yl) ethylcarboxy, and the like.

"$C_{1-6}$-alkylcarbonylamino" as used herein, refers to the radical $C_{1-6}$-alkyl-C(=O)—NH—. Representative examples are acetylamino, propionylamino, pivaloylamino, valeroylamino, and the like.

"arylcarbonylamino" as used herein, refers to the radical aryl-C(=O)—NH—. Representative examples are benzoylamino, naphthylcarbonylamino, 4-biphenylylcarbonylamino, and the like.

"$C_{1-6}$-alkylaminocarbonyl" as used herein, refers to the radicals $C_{1-6}$-alkyl-NH—C(=O)—. Representative examples are methylaminocarbonyl, ethylaminocarbonyl, propylaminocarbonyl, butylaminocarbonyl, pentylaminocarbonyl, hexylaminocarbonyl, and the like.

"di($C_{1-6}$-alkyl)aminocarbonyl" as used herein refers to the radical ($C_{1-6}$-alkyl)$_2$N—C(=O)—. Representative examples are N,N-dimethylaminocarbonyl and N-isopropyl-N-methylaminocarbonyl, and the like.

"di($C_{1-6}$-alkyl)amino-$C_{1-6}$-alkylcarbonyl" as used herein refers to the radical ($C_{1-6}$-alkyl)$_2$N—$C_{1-6}$-alkyl-C(=O)—. Representative examples are 2-(N,N-dimethylamino)acetyl, 2-(N-ethyl-N-methylamino)acetyl, and the like.

"di($C_{1-6}$-alkyl)amino-$C_{1-6}$-alkoxy" as used herein refers to the radical ($C_{1-6}$-alkyl)$_2$N—$C_{1-6}$-alkoxy. Representative examples are N,N-dimethylaminomethoxy, 2-(N,N-dimethylamino)ethoxy, 3-(N,N-dimethylamino)prop-3-oxy, (N-ethyl-N-methylamino)methoxy, and the like.

"Heterocyclyl-$C_{1-6}$-alkoxy" as used herein refers to the radical heterocyclyl-$C_{1-6}$-alkoxy. Representative examples are piperidin-1-ylmethoxy, 2-(piperidin-1-yl)ethoxy, 3-(piperidin-1-yl)prop-3-oxy, piperazin-1-ylmethoxy, 2-(piperazin-1-yl)ethoxy, 3-(piperazin-1-yl)prop-3-oxy, morpholin-1-ylmethoxy, 2-(morpholin-1-yl)ethoxy, 3-(morpholin-1-yl)prop-3-oxy, and the like.

The term "solvate" as used herein is a complex of defined stoichiometry formed by a solute (in casu, a compound according to the present invention) and a solvent. Solvents are those commonly used in the pharmaceutical art, by way of example, water, ethanol, acetic acid, and the like. The term "hydrate" refers to the complex where the solvent molecule is water.

The term "protecting group" or "Pg" refers to a substituent that is commonly employed to block or protect a particular functionality while reacting other functional groups of the compound. Representative examples of protecting groups are amino, hydroxyl, carboxyl protecting groups.

The term "amino protecting group" refers to a substituent on the amino group commonly employed to block or protect the amino functionality while reacting other functional groups on the compound. Examples of such amino protecting groups include the formyl group, the trityl group, the phthalimido group, the trichloroacetyl group, the chloroacetyl, bromoacetyl and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxy-carbonyl, 2-(4-xenyl)iso-propoxycarbonyl, 1,1-diphenyleth-1-yloxycarbonyl, 1,1-diphenylprop-1-yloxycarbonyl, 2-phenylprop-2-yloxycarbonyl, 2-(p-toluoyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluoylsulfonyl)ethoxycarbonyl, 2(methylsulfonyl)ethoxycarbonyl, 2-(triphenylphosphino)ethoxycarbonyl, 9-fluorenylmethoxycarbonyl ("FMOC"), t-butoxycarbonyl ("BOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-(nitro)phenylsulfenyl group, the diphenylphosphine oxide group and like amino-protecting groups. The species of amino-protecting group employed is not critical so long as the derivatized amino group is stable to the condition of subsequent reaction(s) on other positions of the compound of Formula (I) and can be removed at the desired point without disrupting the remainder of the molecule. Preferred amino-protecting groups are the allyloxycarbonyl, the t-butoxycarbonyl, 9-fluorenylmethoxycarbonyl, and the trityl groups. Similar amino-protecting groups used in the cephalosporin, penicillin and peptide art are also embraced by the above terms. Further examples of groups referred to by the above terms are described by J. W. Barton, "Protective Groups In Organic Chemistry", J. G. W. McOmie, Ed., Plenum Press, New York, N.Y., 1973, and T. W. Greene, "Protective Groups in Organic Synthesis", John Wiley and Sons, New York, N.Y., 1981. The related term "protected amino" defines an amino group substituted with an amino-protecting group discussed above.

The term "hydroxyl protecting group" refers to a substituent on the alcohol group commonly employed to block or protect the alcohol functionality while reacting other functional groups on the compound. Examples of such alcohol protecting groups include the 2-tetrahydropyranyl group, 2-ethoxyethyl group, the trityl group, the trichloroacetyl group, urethane-type blocking groups such as benzyloxycarbonyl, and the trialkylsilyl group, examples of such being trimethylsilyl, tert-butyldimethylsilyl, phenyldimethylsilyl, triiospropylsilyl and thexyldimethylsilyl. The choice of alcohol-protecting group employed is not critical so long as the derivatized alcohol group is stable to the condition of subsequent reaction(s) on other positions of the compound of the formulae and can be removed at the desired point without disrupting the remainder of the molecule. Further examples of groups referred to by the above terms are described by J. W. Barton, "Protective Groups In Organic Chemistry", J. G. W. McOmie, Ed., Plenum Press, New York, N.Y., 1973, and T. W. Greene, "Protective Groups in Organic Synthesis", John Wiley and Sons, New York, N.Y., 1981. The related term "protected hydroxyl" or "protected alcohol" defines a hydroxyl group substituted with a hydroxyl-protecting group as discussed above.

The term "carboxyl protecting group" refers to a substituent on the carboxyl group commonly employed to block or protect the —OH functionality while reacting other functional groups on the compound. Examples of such carboxyl protecting groups include the 2-tetrahydropyranyl group, 2-ethoxyethyl group, the trityl group, the allyl group, the trimethylsilylethoxymethyl group, the 2,2,2-trichloroethyl group, the benzyl group, and the trialkylsilyl group, examples of such being trimethylsilyl, tert-butyldimethylsilyl, phenyldimethylsilyl, triiospropylsilyl and thexyldimethylsilyl. The choice of carboxyl protecting group employed is not critical so long as the derivatized alcohol group is stable to the condition of subsequent reaction(s) on other positions of the compound of the formulae and can be removed at the desired point without disrupting the remainder of the molecule. Further examples of groups referred to by the above terms are described by J. W. Barton, "Protective Groups In Organic Chemistry", J. G. W. McOmie, Ed., Plenum Press, New York, N.Y., 1973, and T. W. Greene, "Protective Groups in Organic Synthesis", John Wiley and Sons, New York, N.Y., 1981. The related term "protected carboxyl" defines a carboxyl group substituted with a carboxyl-protecting group as discussed above.

The term "treatment" and "treating" as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular a human being.

The terms "disease", "condition" and "disorder" as used herein are used interchangeably to specify a state of a patient which is not the normal physiological state of man.

The term "modulate" as used herein means to influence, i.e. to modulate a parameter means to influence that parameter in a desired way. Examples are to modulate insulin secretion from beta cells and to modulate the plasma level of free fatty acids.

The term "medicament" as used herein means a pharmaceutical composition suitable for administration of the pharmaceutically active compound to a patient.

The term "prodrug" as used herein includes biohydrolyzable amides and biohydrolyzable esters and also encompasses a) compounds in which the biohydrolyzable functionality in such a prodrug is encompassed in the compound according to the present invention, and b) compounds which may be oxidized or reduced biologically at a given functional group to yield drug substances according to the present invention. Examples of these functional groups include 1,4-dihydropyridine, N-alkylcarbonyl-1,4-dihydropyridine, 1,4-cyclohexadiene, tert-butyl, and the like.

The term "biohydrolyzable ester" as used herein is an ester of a drug substance (in this invention, a compound of formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is trans-formed to (I) in plasma. Many examples of such are known in the art and include by way of example lower alkyl esters (e.g., $C_{1-4}$), lower acyloxyalkyl esters, lower alkoxyacyloxyalkyl esters, alkoxyacyloxy esters, alkyl acylamino alkyl esters, and choline esters.

The term "biohydrolyzable amide" as used herein is an amide of a drug substance (in this invention, a compound of general formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to (I) in plasma. Many examples of such are known in the art and include by way of example lower alkyl amides, α-amino acid amides, alkoxyacyl amides, and alkylaminoalkylcarbonyl amides.

The term "pharmaceutically acceptable" as used herein means suited for normal pharmaceutical applications, i.e. giving rise to no adverse events in patients etc.

The term "effective amount" as used herein means a dosage which is sufficient in order for the treatment of the patient to be effective compared with no treatment.

The term "therapeutically effective amount" of a compound as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

The term "metabolite" as used herein is any intermediate or product resulting from metabolism.

The term "metabolism" as used herein refer to the biotransformation of a drug substance (in this invention, a compound of general formula (I)) administered to a patient.

Combination Treatment

In a further aspect of the present invention the present compounds are administered in combination with one or more further active substances in any suitable ratios. Such further active agents may be selected from antidiabetic agents, antihyperlipidemic agents, antiobesity agents, antihypertensive agents and agents for the treatment of complications resulting from or associated with diabetes.

Suitable antidiabetic agents include insulin, GLP-1 (glucagon like peptide-1) derivatives such as those disclosed in WO 98/08871 (Novo Nordisk A/S), which is incorporated herein by reference, as well as orally active hypoglycemic agents.

Suitable orally active hypoglycemic agents preferably include imidazolines, sulfonylureas, biguanides, meglitinides, oxadiazolidinediones, thiazolidinediones, insulin sensitizers, α-glucosidase inhibitors, agents acting on the ATP-dependent potassium channel of the pancreatic β-cells eg potassium channel openers such as those disclosed in WO 97/26265, WO 99/03861 and WO 00/37474 (Novo Nordisk A/S) which are incorporated herein by reference, potassium channel openers, such as ormitiglinide, potassium channel blockers such as nateglinide or BTS-67582, glucagon antagonists such as those disclosed in WO 99/01423 and WO 00/39088 (Novo Nordisk A/S and Agouron Pharmaceuticals, Inc.), all of which are incorporated herein by reference, GLP-1 agonists such as those disclosed in WO 00/42026 (Novo Nordisk A/S and Agouron Pharmaceuticals, Inc.), which are incorporated herein by reference, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antihyperlipidemic agents and antilipidemic agents, compounds lowering food intake, and PPAR (peroxisome proliferator-activated receptor) and RXR (retinoid X receptor) agonists such as ALRT-268, LG-1268 or LG-1069.

In one aspect of the present invention, the present compounds are administered in combination with a sulphonylurea eg tolbutamide, chlorpropamide, tolazamide, glibenclamide, glipizide, glimepiride, glicazide or glyburide.

In one aspect of the present invention, the present compounds are administered in combination with a biguanide eg metformin.

In one aspect of the present invention, the present compounds are administered in combination with a meglitinide eg repaglinide or senaglinide/nateglinide.

In one aspect of the present invention, the present compounds are administered in combination with a thiazolidinedione insulin sensitizer eg troglitazone, ciglitazone, pioglitazone, rosiglitazone, isaglitazone, darglitazone, englitazone, CS-011/CI-1037 or T 174 or the compounds disclosed in WO 97/41097 (DRF-2344), WO 97/41119, WO 97/41120, WO 00/41121 and WO 98/45292 (Dr. Reddy's Research Foundation), which are incorporated herein by reference.

In one aspect of the present invention the present compounds may be administered in combination with an insulin sensitizer eg such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313 (NN622/DRF-2725), WO 00/50414, WO 00/63191, WO 00/63192, WO 00/63193 (Dr. Reddy's Research Foundation) and WO 00/23425, WO 00/23415, WO 00/23451, WO 00/23445, WO 00/23417, WO 00/23416, WO 00/63153, WO 00/63196, WO 00/63209, WO 00/63190 and WO 00/63189 (Novo Nordisk A/S), which are incorporated herein by reference.

In one aspect of the present invention the present compounds are administered in combination with an α-glucosidase inhibitor eg voglibose, emiglitate, miglitol or acarbose.

In one aspect of the present invention the present compounds are administered in combination with a glycogen phosphorylase inhibitor eg the compounds described in WO 97/09040 (Novo Nordisk A/S).

In one aspect of the present invention the present compounds are administered in combination with an agent acting on the ATP-dependent potassium channel of the pancreatic β-cells eg tolbutamide, glibenclamide, glipizide, glicazide, BTS-67582 or repaglinide.

In one aspect of the present invention the present compounds are administered in combination with nateglinide.

In one aspect of the present invention the present compounds are administered in combination with an antihyperlipidemic agent or a antilipidemic agent eg cholestyramine, colestipol, clofibrate, gemfibrozil, lovastatin, pravastatin, simvastatin, probucol or dextrothyroxine.

Furthermore, the compounds according to the invention may be administered in combination with one or more antiobesity agents or appetite regulating agents.

Such agents may be selected from the group consisting of CART (cocaine amphetamine regulated transcript) agonists, NPY (neuropeptide Y) antagonists, MC3 (melanocortin 3) agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocytestimulating hormone) agonists, MCH (melanocyte-concentrating hormone) antagonists, CCK (cholecystokinin) agonists, serotonin reuptake inhibitors (fluoxetine, seroxat or citalopram), serotonin and norepinephrine reuptake inhibitors, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA (dopamine) agonists (bromocriptin, doprexin), lipase/amylase inhibitors, PPAR modulators, RXR modulators, TR β agonists, adrenergic CNS stimulating agents, AGRP (agouti related protein) inhibitors, H3 histamine antagonists such as those disclosed in WO 00/42023, WO 00/63208 and WO 00/64884, which are incorporated herein by reference, exendin-4, GLP-1 agonists, ciliary neurotrophic factor, and oxyntomodulin. Further antiobesity agents are bupropion (antidepressant), topiramate (anticonvulsant), ecopipam (dopamine D1/D5 antagonist) and naltrexone (opioid antagonist).

In one aspect of the present invention the antiobesity agent is leptin.

In one aspect of the present invention the antiobesity agent is a serotonin and norepinephrine reuptake inhibitor eg sibutramine.

In one aspect of the present invention the antiobesity agent is a lipase inhibitor eg orlistat.

In one aspect of the present invention the antiobesity agent is an adrenergic CNS stimulating agent eg dexamphetamine, amphetamine, phentermine, mazindol phendimetrazine, diethylpropion, fenfluramine or dexfenfluramine.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19th Edition, Gennaro, Ed., Mack Publishing Co., Easton, Pa., 1995.

In one aspect of the present invention, the present compounds are administered in combination with insulin, insulin derivatives or insulin analogues.

In one aspect of the invention the insulin is an insulin derivative is selected from the group consisting of B29-$N^\epsilon$-myristoyl-des(B30) human insulin, B29-$N^\epsilon$-palmitoyl-des(B30) human insulin, B29-$N^\epsilon$-myristoyl human insulin, B29-$N^\epsilon$-palmitoyl human insulin, B28-$N^\epsilon$-myristoyl Lys$^{B28}$Pro$^{B29}$ human insulin, B28-$N^\epsilon$-palmitoyl Lys$^{B28}$Pro$^{B29}$ human insulin B30-$N^\epsilon$-myristoyl-Thr$^{B29}$Lys$^{B30}$ human insulin, B30-$N^\epsilon$-palmitoyl-Thr$^{B29}$Lys$^{B30}$ human insulin, B29-$N^\epsilon$-(N-palmitoyl-γ-glutamyl)-des(B30) human insulin, B29-$N^\epsilon$-(N-lithocholyl-γ-glutamyl)-des(B30) human insulin, B29-$N^\epsilon$-(ω-carboxyheptadecanoyl)-des(B30) human insulin and B29-$N^\epsilon$-(ω-carboxyheptadecanoyl) human insulin.

In another aspect of the invention the insulin derivative is B29-N'-myristoyl-des(B30) human insulin.

In a further aspect of the invention the insulin is an acid-stabilised insulin. The acid-stabilised insulin may be selected from analogues of human insulin having one of the following amino acid residue substitutions:

A21G

A21G, B28K, B29P

A21G, B28D

A21G, B28E

A21G, B3K, B29E

A21G, desB27

A21G, B9E

A21G, B9D

A21G, B10E insulin.

In a further aspect of the invention the insulin is an insulin analogue. The insulin analogue may be selected from the group consisting of An analogue wherein position B28 is Asp, Lys, Leu, Val, or Ala and position B29 is Lys or Pro; and des(B28-B30), des(B27) or des(B30) human insulin.

In another aspect the analogue is an analogue of human insulin wherein position B28 is Asp or Lys, and position B29 is Lys or Pro.

In another aspect the analogue is des(B30) human insulin.

In another aspect the insulin analogue is an analogue of human insulin wherein position B28 is Asp.

In another aspect the analogue is an analogue wherein position B3 is Lys and position B29 is Glu or Asp.

In another aspect the GLP-1 derivative to be employed in combination with a compound of the present invention refers to GLP-1(1-37), exendin-4(1-39), insulinotropic fragments thereof, insulinotropic analogues thereof and insulinotropic derivatives thereof. Insulinotropic fragments of GLP-1(1-37) are insulinotropic peptides for which the entire sequence can be found in the sequence of GLP-1(1-37) and where at least one terminal amino acid has been deleted. Examples of insulinotropic fragments of GLP-1(1-37) are GLP-1(7-37) wherein the amino acid residues in positions 1-6 of GLP-1(1-37) have been deleted, and GLP-1(7-36) where the amino acid residues in position 1-6 and 37 of GLP-1(1-37) have been deleted. Examples of insulinotropic fragments of exendin-4(1-39) are exendin-4(1-38) and exendin-4(1-31). The insulinotropic property of a compound may be determined by in vivo or in vitro assays well known in the art. For instance, the compound may be administered to an animal and monitoring the insulin concentration over time. Insulinotropic analogues of GLP-1(1-37) and exendin-4(1-39) refer to the respective molecules wherein one or more of the amino acids residues have been exchanged with other amino acid residues and/or from which one or more amino acid residues have been deleted and/or from which one or more amino acid residues have been added with the proviso that said analogue either is insulinotropic or is a prodrug of an insulinotropic compound. Examples of insulinotropic analogues of GLP-1(1-37) are e.g. Met$^8$-GLP-1(7-37) wherein the alanine in position 8 has been replaced by methionine and the amino acid residues in position 1 to 6 have been deleted, and Arg$^{34}$-GLP-1(7-37) wherein the valine in position 34 has been replaced with arginine and the amino acid residues in position 1 to 6 have been deleted. An example of an insulinotropic analogue of exendin-4(1-39) is Ser$^2$Asp$^3$-exendin-4(1-39) wherein the amino acid residues in position 2 and 3 have been replaced with serine and aspartic acid, respectively (this particular analogue also being known in the art as exendin-3). Insulinotropic derivatives of GLP-1(1-37), exendin-4(1-39) and analogues thereof are what the person skilled in the art considers to be derivatives of these peptides, i.e. having at least one substituent which is not present in the parent peptide molecule with the proviso that said derivative either is insulinotropic or is a prodrug of an insulinotropic compound. Examples of substituents are amides, carbohydrates, alkyl groups and lipophilic substituents. Examples of insulinotropic derivatives of GLP-1(1-37), exendin-4(1-39) and analogues thereof are GLP-1(7-36)-amide, Arg$^{34}$, Lys$^{26}$($N^\epsilon$-(γ-Glu($N^\alpha$-hexadecanoyl)))-GLP-1(7-37) and Tyr$^{31}$-exendin-4(1-31)-amide. Further examples of GLP-1(1-37), exendin-4(1-39), insulinotropic fragments thereof, insulinotropic analogues thereof and insulinotropic derivatives thereof are described in WO 98/08871, WO 99/43706, U.S. Pat. No. 5,424,286 and WO 00/09666.

In another aspect of the present invention, the present compounds are administered in combination with more than one of the above-mentioned compounds e.g. in combination with metformin and a sulphonylurea such as glyburide; a sulphonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

It should be understood that any suitable combination of the compounds according to the invention with diet and/or exercise, one or more of the above-mentioned compounds and optionally one or more other active substances are considered to be within the scope of the present invention. In one aspect of the present invention, the pharmaceutical composition according to the present invention comprises e.g. a compound of the invention in combination with metformin and a sulphonylurea such as glyburide; a compound of the invention in combination with a sulphonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

Pharmaceutical Compositions

The compounds of the present invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as hard or soft capsules, tablets, troches, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, aqueous or oily suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.05 to about 1000 mg, preferably from about 0.1 to about 500 mg, and more preferred from about 0.5 mg to about 200 mg.

For parenteral routes such as intravenous, intrathecal, intramuscular and similar administration, typically doses are in the order of about half the dose employed for oral administration.

The compounds of this invention are generally utilized as the free substance or as a pharmaceutically acceptable salt thereof. Examples are an acid addition salt of a compound having the utility of a free base and a base addition salt of a compound having the utility of a free acid. The term "pharmaceutically acceptable salts" refers to non-toxic salts of the compounds of this invention which are generally prepared by reacting the free base with a suitable organic or inorganic acid or by reacting the acid with a suitable organic or inorganic base. When a compound according to the present invention contains a free base such salts are prepared in a conventional manner by treating a solution or suspension of the compound with a chemical equivalent of a pharmaceutically acceptable acid. When a compound according to the present invention contains a free acid such salts are prepared in a conventional manner by treating a solution or suspension of the compound with a chemical equivalent of a pharmaceutically acceptable base. Physiologically acceptable salts of a compound with a hydroxy group include the anion of said compound in combination with a suitable cation such as sodium or ammonium ion. Other salts which are not pharmaceutically acceptable may be useful in the preparation of compounds of the present invention and these form a further aspect of the present invention.

For parenteral administration, solutions of the novel compounds of the formula (I) in sterile aqueous solution, aqueous propylene glycol or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the novel compounds of the present invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, incorporated herein by reference, to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the present invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the present invention are contemplated. For the purpose of this application, topical applications shall include mouth washes and gargles.

The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

In addition, some of the compounds of the present invention may form solvates with water or common organic solvents. Such solvates are also encompassed within the scope of the present invention.

Thus, in a further aspect, there is provided a pharmaceutical composition comprising a compound according to the present invention, or a pharmaceutically acceptable salt, solvate, or prodrug thereof, and one or more pharmaceutically acceptable carriers, excipients, or diluents.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet that may be prepared by conventional tabletting techniques may contain:

| Core: | |
|---|---|
| Active compound (as free compound or salt thereof) | 5.0 mg |
| Lactosum Ph. Eur. | 67.8 mg |
| Cellulose, microcryst. (Avicel) | 31.4 mg |
| Amberlite ®IRP88* | 1.0 mg |
| Magnesii stearas Ph. Eur. | q.s. |
| Coating: | |
| Hydroxypropyl methylcellulose | approx. 9 mg |
| Mywacett 9-40 T** | approx. 0.9 mg |

*Polacrillin potassium NF, tablet disintegrant, Rohm and Haas.
**Acylated monoglyceride used as plasticizer for film coating.

If desired, the pharmaceutical composition of the present invention may comprise a compound according to the present invention in combination with further active substances such as those described in the foregoing.

EXAMPLES

Abbreviations

Abbreviations used in the Schemes and Examples are as follows:
d=day(s)
g=gram(s)
h=hour(s)
Hz=hertz
kD=kiloDalton(s)
L=liter(s)
M=molar
mbar=millibar
mg=milligram(s)
min=minute(s)
mL=milliliter(s)
mM=millimolar
mmol=millimole(s)
mol=mole(s)
N=normal
ppm=parts per million
psi=pounds per square inch
APCI=atmospheric pressure chemical ionization
ESI=electrospray ionization
i.v.=intravenous
m/z=mass to charge ratio
mp=melting point
MS=mass spectrometry
HPLC=high pressure liquid chromatography
RP=reverse phase
HPLC-MS=high pressure liquid chromatography-mass spectrometry
NMR=nuclear magnetic resonance spectroscopy
p.o.=per oral
$R_f$=relative TLC mobility
rt=room temperature
s.c.=subcutaneous
TLC=thin layer chromatography
$t_r$=retention time
BOP=(1-benzotriazolyloxy)tris(dimethylamino)phosphonium hexafluorophosphate
CDI=carbonyldiimidazole
DCM=dichloromethane, $CH_2Cl_2$, methylenechloride
DBU=1,8-diazabicyclo[5.4.0]undec-7-ene
DEAD=diethyl azodicarboxylate
DIC=1,3-diisopropylcarbodiimide
*DIEA=N,N-diisopropylethylamine
*DIPEA=N,N-diisopropylethylamine
DMA=N,N-dimethylacetamide
DMF=N,N-dimethylformamide
DMPU=N,N'-dimethylpropyleneurea, 1,3-dimethyl-2-oxohexahydropyrimidine
DMSO=dimethylsulfoxide
*EDC=1-ethyl-3-(3-dimethylaminopropyl)carbodiimide hydrochloride
*EDAC=1-ethyl-3-(3-dimethylaminopropyl)carbodiimide hydrochloride
$Et_2O$=diethyl ether
EtOAc=ethyl acetate
HMPA=hexamethylphosphoric acid triamide
HOAt=1-hydroxy-7-azabenzotriazole
HOBt=1-hydroxybenzotriazole
LAH=lithium aluminum hydride, $LiAlH_4$
LDA=lithium diisopropylamide
MeCN=acetonitrile
MeOH=methanol
NMM=N-methylmorpholine, 4-methylmorpholine
NMP=N-methylpyrrolidin-2-one
TEA=triethylamine
TFA=trifluoroacetic acid
THF=tetrahydrofuran
THP=tetrahydropyranyl
TTFH=fluoro-N,N,N',N-tetramethylformamidinium hexafluorophosphate
$CDCl_3$=deuterio chloroform
$CD_3OD$=tetradeuterio methanol
DMSO-$d_6$=hexadeuterio dimethylsulfoxide General The following examples and general procedures refer to intermediate compounds and final products for general formula (I) identified in the specification and in the synthesis schemes. The preparation of the compounds of general formula (I) of the present invention is described in detail using the following examples. Occasionally, the reaction may not be applicable as described to each compound included within the disclosed scope of the invention. The compounds for which this occurs will be readily recognised by those skilled in the art. In these cases the reactions can be successfully performed by conventional modifications known to those skilled in the art, which is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may be prepared by a person skilled in the art in analogy with the preparation of similar known compounds or by the General procedures and methods described herein.

The structures of the compounds are confirmed by either elemental analysis or nuclear magnetic resonance (NMR), where peaks assigned to characteristic protons in the title compounds are presented where appropriate General Procedures General Procedure (A)

Compounds of the formula (I) according to the invention wherein can be prepared in analogy with the methods described in patent application WO 2003/015774, WO 2005/054200, WO 2005/044801, WO 2005/05233, WO 2005/080360, WO 2005/080359 or WO 2003/015774, and if needed followed by a hydrolysis to the corresponding acid with in example either NaOH or LiOH in an appropriate solvent as THF/$H_2O$ or MeOH/$H_2O$. The appropriate substituted phenyl starting material is either commercial available, described in the literature (in example application WO 2003/015774, WO 2005/054200, WO 2005/044801, WO 2005/05233, WO 2005/080360, WO 2005/080359 or WO 2003/015774) or may be prepared by a person skilled in the art in analogy with the preparation of similar known compounds or by the General procedures and methods described herein.

The appropriate aminothiazole $H_2N$-A, wherein A is defined as for formula (I) or a protected analogous hereof is either commercial available, described in the literature or may be prepared by a person skilled in the art in analogy with the preparation of similar known compounds or by the General procedures and methods described herein.

General Synthetic Descriptions

General Synthetic Description A

Preparation of N-2-thiazolyl Amides of Benzoic Acids

To a solution of a substituted benzoic acid (0.25 mmol) in dichloromethane (3 mL) was added a drop of N,N-dimethylformamide and oxalyl chloride (50 µL) at 0° C. The contents were stirred for 2 h at room temperature. All the volatiles were removed under reduced pressure. The crude acid chloride was dissolved in dichloromethane (2 mL) and the resulting solution was added to a mixture of 2-aminothiazole or its derivative (0.5 mmol) and triethylamine (100 µL) in dichloromethane (2 mL) at 0° C. The contents were stirred at room temperature for 1 h. All the volatiles were removed under reduced pressure. The residue was purified by column chromatography on silica using 10-20% ethyl acetate in dichloromethane as eluent to obtain pure desired amides.

General Synthetic Description B

Preparation of 3,5-dialkoxybenzoic Acids

To methyl 3,5-dihydroxybenzoate (2.0 mmol) in DMF (5 ml) was added NaH (200 mg, 60% in mineral oil, 5 mmol) and a alkyl halide (4.4 mmol) at 0° C. and the resulting mixture was stirred at room temperature for 12 h. The reaction mixture was poured in to water and extracted with ethyl acetate. The combined ethyl acetate extracts were washed with brine (150 ml), dried over sodium sulfate and concentrated. To the crude ester in tetrahydrofuran (5 ml) was added 2N NaOH (5 mL) and the contents were stirred for 1 h. The reaction mixture was acidified with conc HCl and extracted with ethyl acetate. The combined ethyl acetate extracts were washed with brine, dried over sodium sulfate and concentrated. The crude 3,5-dialkoxybenzoic acids were obtained in 70-80% yield and were used as such.

General Synthetic Description C

Preparation of Aryloxybenzamides

The mixture of in example 3-alkoxy-5-hydroxybenzamide (0.2 mmol), copper powder (0.22 mmol), potassium carbonate (0.6 mmol) and aryl halide (0.22 mmol) in pyridine (2 ml) heated at 100° C. for 12 h. Then cooled the reaction mass to room temperature, diluted with ethyl acetate and filtered through celite. Celite bed was washed thoroughly with ethyl acetate; combined ethyl acetate filtrates were washed with 1N HCl, dried over sodium sulfate and concentrated to get a syrupy material. This crude syrupy compound was purified by silica gel column to obtain desired aryloxy benzamides in 30-40% yields.

General Synthetic Description D

Preparation of Aryloxybenzoates Hereof (Evans Coupling)

To a mixture of in example methoxy-3-alkoxy-5-hydroxybenzoate (4.0 mmol), copper acetate (8.0 mmol) and molecular sieves in DCM (35 mL) was added phenylboronic acid (8.0 mmol) or a substituted phenylboronic acid (8.0 mmol). This mixture was sparged with oxygen (balloon) for 15 min; after addition of triethyamine (8.0 mmol), oxygen sparging was continued for an additional 15 min. The resulting brown/black suspension was stirred under an oxygen atmosphere for 6-12 h at ambient temperature. The reaction slurry was then filtered through a 2" silica plug to remove any solid byproducts. After washing the silica gel with 100 mL DCM, the filtrate was concentrated and further purified by gradient flash chromatography. The desired aryloxybenzoates were obtained in 30-60% yield.

General Synthetic Description E for Hydrolysis

Ester (1 mmol) was dissolved in a 1:1 mixture of THF and methanol (5 mL). To this solution was added a 2 M solution of LiOH (2 mL, 4 mmol). The mixture was stirred for 4-6 h and was concentrated. The residue was diluted with water (10 mL) and the aqueous layer was washed with ethyl acetate (2×10 mL). The water layer was acidified with HCl to pH 6.0 and the precipitated acid was extracted with ethyl acetate (2×50 mL). The organic layer was washed with water (2×20 mL), dried ($Na_2SO_4$) and concentrated in vacuo to furnish corresponding carboxylic acid.

General Synthetic Description F for the Synthesis of Alkylthiobenzamides

In example a mixture of 3,5-dialkoxy-N-(-5-bromothiazol-2-yl)-benzamide [or 3-alkoxy-5-phenoxy-N-(-5-bromothiazol-2-yl)-benzamide] (prepared as described above) (1 mmol), alkylthiol or a derivative hereof (2 mmol) and potassium carbonate (4 mmol) in DMF (5 mL) was heated at 80° C. for 12 h. The mixture was poured into water (20 mL) and was extracted with ethyl acetate (3×25 mL). The organic layer was washed with water (2×30 mL), brine (1×30 mL), dried (anhydrous $Na_2SO_4$) and concentrated in vacuo to furnish a residue containing 3,5-dialkoxy-N-(5-alkylthio-thiazol-2-yl)-benzamide. The crude product was purified by column chromatography (silica, 10-50% ethyl acetate in hexanes) to afford 3,5-dialkoxy-N-(5-alkylthio-thiazol-2-yl)-benzamide or 3-alkoxy-5-phenoxy-N-(5-alkylthio-thiazol-2-yl)benzamide.

General Synthetic Description G for the Synthesis of Alkyl/Arylsulfones

In example 3,5-dialkoxy-N-(5-alkylthio-thiazol-2-yl)-benzamide or 3-alkoxy-5-phenoxy-N-(5-alkylthio-thiazol-2-yl)-benzamide (0.5 mmol) was dissolved in $CH_2Cl_2$ (6 mL) and was cooled to 0° C. in an ice bath. To this solution was added peroxyacetic acid (10 mmol) in $CH_2Cl_2$ (5 mL). The mixture was stirred for 4 h at 0° C. and was diluted with $CH_2Cl_2$ (50 mL). The organic layer was washed with saturated solution of $NaHCO_3$ (2×30 mL), water (3×30 mL), brine (1×30 mL), dried (anhydrous $Na_2SO_4$) and concentrated in vacuo. The crude mixture was purified by column chromatography (silica gel) with 20-40% ethyl acetate in hexanes to give the desired sulfonyl products in 40-60% yield.

General Synthetic Description H for the Preparation of 3-{(1S)-2-methoxy-(methylethyl)oxy}-5-{[4-fluorophenyl]oxy}benzoic Acid

Step A

Synthesis of methyl-3-hydroxy-5-{[(2-methylphenyl)methyl]oxy}benzoate

To a solution of methyl 3,5-dihydroxybenzoate (50 g, 0.30 mol) in DMF (500 ml) at 0° C. was added sodium hydride (10.8 g, 0.27 mol) portion wise. The reaction was allowed to warm to 15° C., and stirred for 20 minutes. The mixture was re-cooled to 0° C. and a solution of 2-methylbenzyl bromide (36 ml, 0.27 mol) in DMF (50 ml) was added over 30 minutes. The reaction was warmed to ambient temperature and concentrated in vacuo. The residual oil was partitioned between ethyl acetate (500 ml) and water (250 ml), and the ethyl acetate layer was separated, washed with water and evaporated. The residue was purified by column chromatograph on silica gel (gradient, 0-100% ethyl acetate in isohexane) to give the desired compound (21.9 g, 27%).
$^1$H NMR (300 MHz, $CDCl_3$) δ: 7.15-7.42 (m, 6H), 6.69 (t, 1H), 5.61 (s, 1H), 5.02 (s, 1H), 3.90 (s, 3H), 2.39 (s, 3H).

Step B

Synthesis of Methyl 3-{(1S)-2-methoxy-(1-methylethyl)oxy}-5-{[(2-methylphenyl)methyl]oxy}benzoate A stirred suspension of methyl 3-hydroxy-5-{[(2-methylphenyl)methyl]oxy}benzoate (15.3 g, 56.25 mmol) and triphenyl phosphine (14.4 g, 55 mmol) in dry chloromethane (900 ml) was cooled in an ice-bath and diisopropyl azodicarboxylate (11.88 ml, 55 mmol) was added dropwise. The reaction mixture was stirred at 0-5° C. for 30 minutes and (R)-methoxy-propan-2-ol was added dropwise. The reaction mixture was stirred at ambient temperature for 16 hours, and filtered through diatomaceous earth. The filtrate was evaporated and purified by column chromatograph on silica gel eluting with 10% ethyl acetate in iso-hexane to give the desired compound (10.7 g, 55%).
$^1$H NMR (300 MHz, $CDCl_3$) δ: 7.40 (d, 1H), 7.25 (m, 5H), 6.80 (s, 1H), 5.00 (s, 2H), 4.60-4.55 (m, 1H), 3.92 (s, 3H), 3.63-3.51 (m, 2H), 3.42 (s, 3H), 2.41 (s, 3H), 1.32 (d, 3H).

Step C

Synthesis of Methyl 3-hydroxy-5-[(1S)-2-methoxy-(1-methylethyl)oxy]benzoate

Methyl 3-{(1S)-2-methoxy-(1-methylethyl)oxy}-5-{[(2-methylphenyl)methyl]oxy}benzoate (50 g, 0.152 mol) was dissolved in THF/ethanol (1:1, 600 ml) and 10% Palladium on carbon (5.0 g) was added. The mixture was hydrogenated under normal pressure at room temperature. The catalyst was filtered off, and the filtrate concentrated in vacuo to give the desired compound (36.7 g, 99%).
$^1$H NMR (300 MHz, $CDCl_3$) δ: 7.13 (d, 2H), 6.64 (s, 1H), 6.30 (s, 1H), 4.61-4.54 (m, 1H), 3.91 (s, 3H), 3.62-3.49 (m, 2H), 3.38 (s, 3H), 1.35 (d, 3H).

Step D

Synthesis of Methyl 3-{(1S)-2-methoxy-(methylethyl)oxy}-5-{[4-fluorophenyl]oxy}benzoate A suspension of methyl 3-hydroxy-5-[(1S)-2-methoxy-(1-methylethyl)oxy]benzoate (3.53 g, 14.7 mmol), p-fluorophenyl-boronic acid (16.2 mmol), copper(II) acetate (2.94 g, 16.2 mmol), triethylamine (10.3 ml, 73.5 mmol) and freshly activated 4 A molecular sieves (17.7 g) in dichloromethane was stirred at ambient temperature and under ambient atmosphere for 2 days. The reaction mixture was filtered, and the dichloromethane was removed in vacuo. The residual oil was partitioned between ethyl acetate and 2 mol/l hydrochloric acid. The ethyl acetate layer was separated, washed with aqueous sodium hydrogen carbonate and brine, dried over $Na_2SO_4$ and evaporated to give a residue, which was purified by column chromatograph on silica gel (20-60% ethyl acetate in iso-hexane, gradient) to give the desired ester.

Step E

Synthesis of 3-{(1S)-2-methoxy-(methylethyl)oxy}-5-{[4-fluorophenyl]oxy}benzoic Acid To a solution of methyl 3-{(1S)-2-methoxy-(methylethyl)oxy}-5-{[4-fluorophenyl]oxy}benzoate (5.08 mmol) in 40 ml THF was added a solution of sodium hydroxide (0.61 g, 15.23 mmol) in 15 ml $H_2O$. The mixture was stirred for 13 hours at ambient temperature and concentrated. The residue was acidified to pH 4 with 1 mol/L citric acid solution, and extracted with ethyl acetate (2×100 ml). The combined extracts were washed with brine, dried over $Na_2SO_4$ and evaporated to give 3-{(1S)-2-methoxy-(methylethyl)oxy}-5-{[4-(methylsulfonyl)phenyl]oxy}benzoic acid.

Example 1

General Procedure (A)

[2-(3-isopropoxy-5-phenoxy-benzoylamino)-thiazol-5-yl-sulfanyl]-acetic acid methyl ester

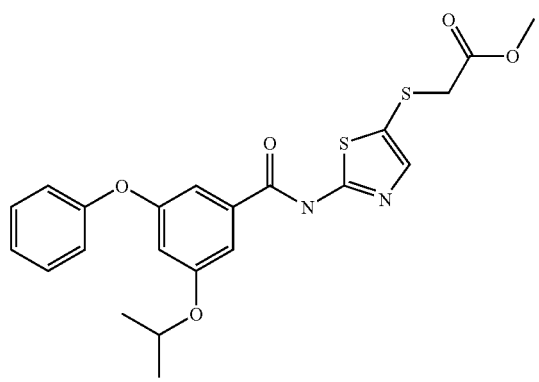

[2-(3-isopropoxy-5-phenoxy-benzoylamino)-thiazol-5-yl-sulfanyl]-acetic acid methyl ester was prepared in three steps.

Step A:

Methyl-3-isopropyloxy-5-phenoxybenzoate (3.15 g, 11.0 mmol) was prepared from methyl-3-isopropxy-5-hydroxybenzoate (6.3 g, 30.0 mmol) and phenylboronic acid (7.32 g, 60.0 mmol) in 36% yield following general procedure D. An additional 29% of recovered starting material was recycled. Methyl-3-isopropyloxy-5-phenoxybenzoate (2.75 g) was hydrolyzed to 3-isopropyloxy-5-phenoxybenzoic acid (2.40 g) in 92% yield following general procedure E.

LC-MS (m/z): 272 (M+1)+; 1H NMR (CDCl3, 400 MHz): δ 1.35 (d, 6H), 4.58 (m, 1H), 6.76 (t, 1H), 7.03 (d, 2H), 7.14 (t, 1H), 7.24 (m, 1H), 7.30-7.40 (m, 3H), 10.39 (br, 1H) ppm.

Step B:

3-Isopropyloxy-5-phenoxy-N-(5-bromothiazol-2-yl)-benzamide (1.1 g, 82%) was prepared from 5-bromo-2-aminothiazole (830 mg, 4.6 mmol) and 3-isopropyloxy-5-phenoxybenzoic acid (835 mg, 3.1 mmol) following the general procedure A.

LC-MS (m/z): 434 (M+1)+; 1H NMR (CDCl3, 400 MHz): δ 1.35 (d, 6H), 4.55 (m, 1H), 6.76 (t, 1H), 6.97 (d, 1H), 7.04-7.08 (m, 2H), 7.14 (m, 1H), 7.18 (m, 2H), 7.35-7.39 (m, 2H), 11.80 (br, 1H) ppm.

Step C:

[2-(3-Isopropoxy-5-phenoxy-benzoylamino)-thiazol-5-yl-sulfanyl]-acetic acid methyl ester (100 mg) was prepared from 3-isopropyloxy-5-phenoxy-N-(5-bromothiazol-2-yl)-benzamide (370 mg, 0.85 mmol) and methyl mercaptoacetate (0.4 mL, 4.0 mmol) in 26% yield following the general procedure F.

LC-MS (m/z): 461 (M+1)+; 1H NMR (CDCl3, 400 MHz): δ 1.34 (d, 6H), 3.43 (s, 2H), 3.67 (s, 3H), 4.54 (m, 1H), 6.74 (t, 1H), 7.02-7.08 (m, 3H), 7.10-7.22 (m, 3H), 7.34 (t, 2H), 12.48 (br, 1H) ppm.

Example 2

General Procedure (A)

[2-(3-Isopropoxy-5-phenoxy-benzoylamino)-thiazol-5-yl-sulfanyl]-acetic acid

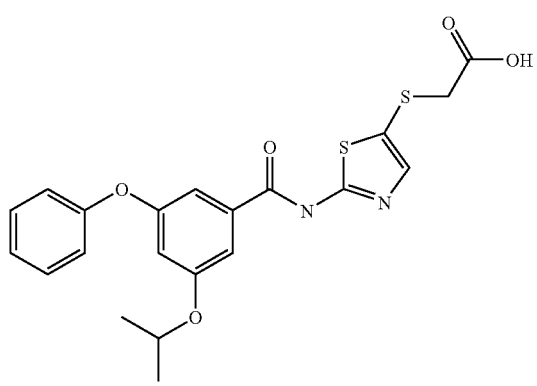

Step A:

[2-(3-Isopropoxy-5-phenoxy-benzoylamino)-thiazol-5-yl-sulfanyl]-acetic acid (80 mg) was obtained in 83% yield from [2-(3-isopropoxy-5-phenoxy-benzoylamino)-thiazol-5-yl-sulfanyl]-acetic acid methyl ester (100 mg, 0.22 mmol) following general procedure E.

LC-MS (m/z): 445 (M+1)+; 1H NMR (d6-DMSO, 400 MHz): δ 1.28 (d, 6H), 3.55 (s, 2H), 4.72 (m, 1H), 6.75 (t, 1H), 7.08 (m, 2H), 7.17-7.21 (m, 2H), 7.39-7.45 (m, 3H), 7.60 (s, 1H), 13.0 (br, 1H) ppm.

Example 3

General Procedure (A)

3-[2-(3-Isopropoxy-5-phenoxy-benzoylamino)-thiazol-5-yl-sulfanyl]-propionic acid methyl ester

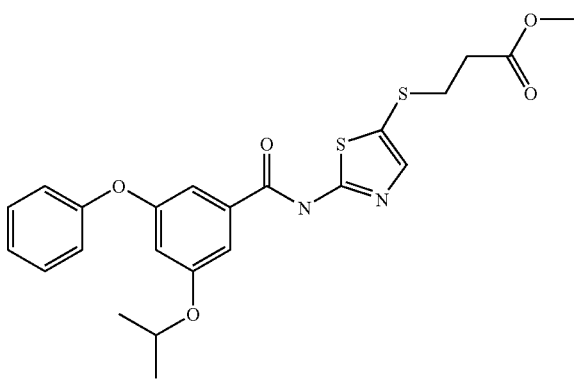

Step A:

3-[2-(3-Isopropoxy-5-phenoxy-benzoylamino)-thiazol-5-yl-sulfanyl]-propionic acid methyl ester (30 mg) was prepared from 3-isopropyloxy-5-phenoxy-N-(5-bromothiazol-2-yl)benzamide (example 1, step 2) (370 mg, 0.85 mmol) and 3-mercaptopropionic acid methyl ester (0.5 mL, 4.0 mmol) in 7% yield following general procedure F.

LC-MS (m/z): 473 (M+1)+; 1H NMR (CDCl3, 400 MHz): δ 1.34 (d, 6H), 2.6 (m, 2H), 2.90 (m, 2H), 3.67 (s, 3H), 4.54 (m, 1H), 6.75 (t, 1H), 7.02-7.08 (m, 3H), 7.10-7.16 (m, 2H), 7.20 (d, 1H), 7.34 (t, 2H), 12.05 (br, 1H) ppm.

Example 4

General Procedure (A)

3-[2-(3-Isopropoxy-5-phenoxy-benzoylamino)-thiazol-5-yl-sulfanyl]-propionic acid

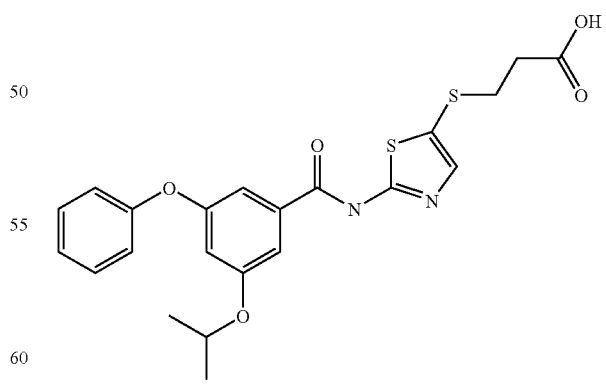

Step A:

3-[2-(3-Isopropoxy-5-phenoxy-benzoylamino)-thiazol-5-yl-sulfanyl]-propionic acid (14 mg) was prepared from 3-[2-(3-isopropoxy-5-phenoxy-benzoylamino)-thiazol-5-yl-sulfanyl]-propionic acid methyl ester (18 mg) following general procedure E in 80% yield.

LC-MS (m/z): 459 (M+1)+; 1H NMR (DMSO-d6, 400 MHz): δ 1.34 (d, 6H), 2.7 (m, 2H), 2.90 (m, 2H), 4.54 (m, 1H), 6.74 (t, 1H), 7.04-7.10 (m, 3H), 7.10-7.16 (m, 2H), 7.20 (d, 1H), 7.34 (t, 2H) ppm

Example 5

General Procedure (A)

[2-(3-Isopropoxy-5-phenoxy-benzoylamino)-thiazol-5-yl-sulfonyl]-acetic acid methyl ester

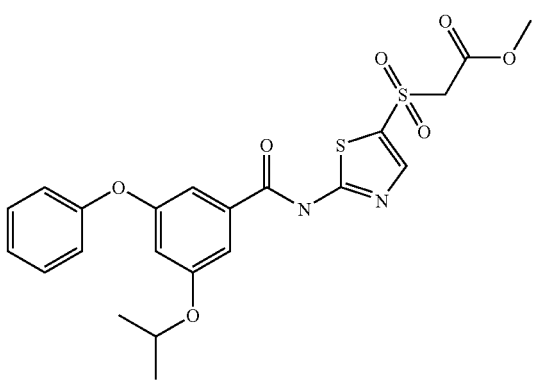

Step A:

[2-(3-Isopropoxy-5-phenoxy-benzoylamino)-thiazol-5-yl-sulfonyl]-acetic acid methyl ester (72 mg) was prepared in 45% yield from [2-(3-isopropoxy-5-phenoxy-benzoylamino) thiazol-5-yl-sulfanyl]-acetic acid methyl ester (example 1) (150 mg, 0.33 mmol following general procedure G.

LC-MS (m/z): 491 (M+1)+; 1H NMR (CDCl3, 400 MHz): δ 1.36 (d, 6H), 3.76 (s, 3H), 4.20 (s, 2H), 4.54 (m, 1H), 6.76 (t, 1H), 7.06-7.09 (m, 3H), 7.16-7.20 (m, 2H), 7.36 (m, 2H), 7.87 (s, 1H), 11.57 (br, 1H) ppm.

Example 6

General Procedure (A)

[2-(3-Isopropoxy-5-phenoxy-benzoylamino)-thiazol-5-yl-sulfonyl]-acetic acid

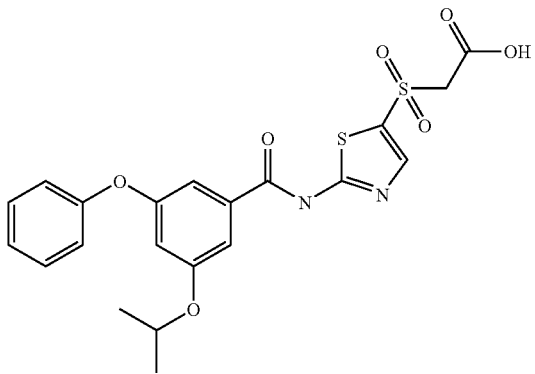

Step A:

[2-(3-Isopropoxy-5-phenoxy-benzoylamino)-thiazol-5-yl-sulfonyl]-acetic acid (45 mg) was obtained in 93% yield from [2-(3-isopropoxy-5-phenoxy-benzoylamino)-thiazol-5-ylsulfonyl]-acetic acid methyl ester (50 mg) following general procedure E.

LC-MS (m/z): 477 (M+1)+; 1H NMR (d6-DMSO, 400 MHz): δ 1.28 (d, 6H), 4.60 (s, 2H), 4.75 (m, 1H), 6.79 (t, 1H), 7.09 (m, 2H), 7.21 (m, 2H), 7.39-7.48 (m, 3H), 8.16 (s, 1H) ppm.

Example 7

General Procedure (A)

[2-(3,5-Diethoxy-benzoylamino)-thiazol-5-ylsulfanyl]-acetic acid methyl ester

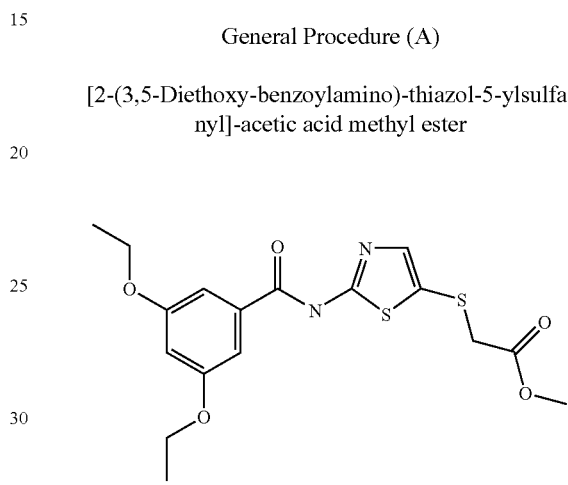

Step A:

Preparation of N-(5-Bromo-thiazol-2-yl)-3,5-diethoxy-benzamide:

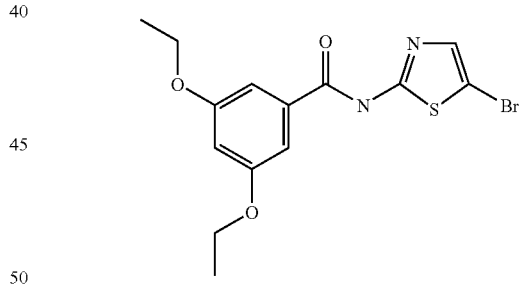

N-(5-Bromo-thiazol-2-yl)-3,5-diethoxy-benzamide (3.19 g, 86%) was prepared-from the corresponding acid (2.10 g, 10.0 mmol) and 2-amino-5-bromothiazole hydrobromide (2.60 g) following general procedure A.

LC-MS (m/z): 372 (M+1)+; 1H NMR (CDCl3, 400 MHz): δ 1.44 (t, 6H), 4.04 (q, 4H), 6.69 (s, 1H), 7.03 (s, 2H), 7.11 (s, 1H), 12.09 (br, 1H) ppm.

Step B

The desired benzamide (90 mg, 17%) was prepared from the corresponding bromothiazole (500 mg, 1.35 mmol) and methyl thioglycolate (220 μL) following general procedure F.

LC-MS (m/z): 397 (M+1)+; 1H NMR (CDCl3, 400 MHz): δ 1.43 (t, 6H), 3.47 (s, 2H), 3.73 (s, 3H), 4.05 (q, 2H), 6.69 (s, 1H), 7.03 (s, 2H), 7.30 (s, 1H), 11.48 (br, 1H) ppm.

Example 8

General Procedure (A)

[2-(3,5-Diethoxy-benzoylamino)-thiazol-5-ylsulfanyl]-acetic acid

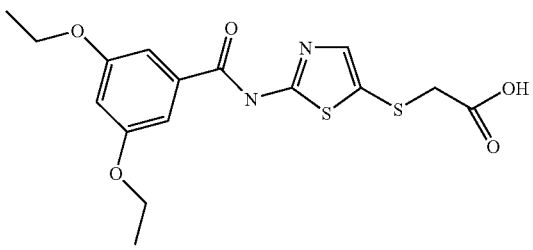

Step A:

The desired acid (42 mg, 97%) was prepared from the corresponding methyl ester (45 mg, 0.11 mmol) following general procedure E.

LC-MS (m/z): 383 (M+1)+; 1H NMR (DMSO-d6, 400 MHz): δ 1.34 (t, 6H), 3.58 (s, 2H), 4.09 (q, 4H), 6.71 (s, 1H), 7.25 (2, 2H), 7.64 (s, 1H) ppm.

Example 9

General Procedure (A)

[2-(3,5-Diethoxy-benzoylamino)-thiazole-5-sulfonyl]-acetic acid methyl ester

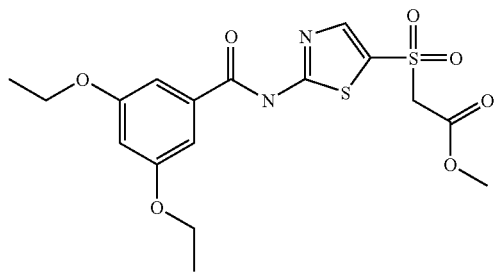

Step A:

The desired sulfone (18 mg, 60%) was prepared from the corresponding thiazole-thio ether (example 7) (28 mg, 0.07 mmol) following general procedure G.

LC-MS (m/z): 429 (M+1)+; 1H NMR (CDCl3, 400 MHz): δ 1.44 (t, 6H), 3.79 (s, 3H), 4.10 (q, 4H), 4.25 (s, 2H), 6.71 (s, 1H), 7.14 (s, 2H), 7.93 (s, 1H), 12.18 (br, 1H) ppm.

Example 10

General Procedure (A)

[2-(3,5-Diethoxy-benzoylamino)-thiazole-5-sulfonyl]-acetic acid

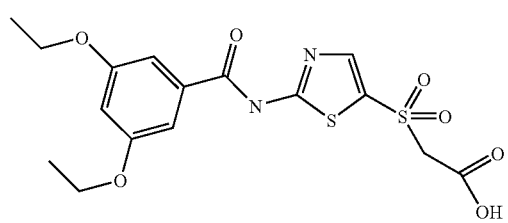

Step A:

The desired sulfone (10 mg, 87%) was prepared from the corresponding thio ester (example 9) (11 mg, 0.03 mmol) following general procedure E.

LC-MS (m/z): 415 (M+1)+; 1H NMR (DMSO-d6, 400 MHz): δ 1.35 (t, 6H), 4.09 (q, 4H), 4.63 (s, 2H), 6.75 (s, 1H), 7.28 (s, 2H), 8.20 (s, 1H) ppm.

Example 11

General Procedure (A)

3-[2-(3,5-Diethoxy-benzoylamino)-thiazol-5-ylsulfanyl]-propionic acid methyl ester

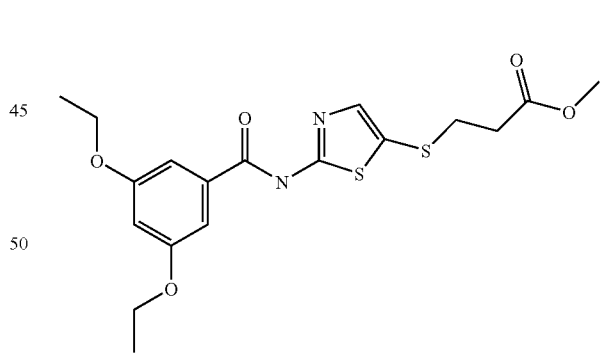

Step A:

The desired benzamide (57 mg, 26%) was prepared from the corresponding bromothiazole (described in example 7) (200 mg, 0.54 mmol) and methyl-3-thio propionate (180 μL) following general procedure F.

LC-MS (m/z): 411 (M+1)+; 1H NMR (CDCl3, 400 MHz): δ 1.43 (t, 6H), 2.62 (m, 2H), 2.97 (m, 2H), 3.69 (s, 3H), 4.05 (q, 4H), 6.68 (s, 1H) 7.04 (s, 2H) 7.25 (s, 1H) 11.42 (br, 1H) ppm.

Example 12

General Procedure (A)

[2-(3,5-Diisopropoxy-benzoylamino)-thiazol-5-yl-sulfanyl]-acetic acid methyl ester

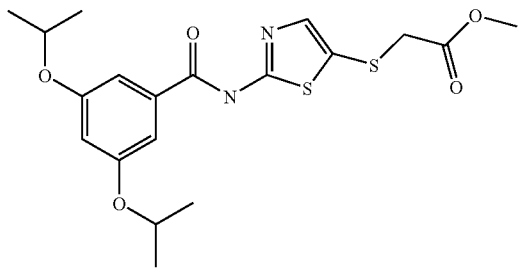

Step A:

[2-(3,5-Diisopropoxy-benzoylamino)-thiazol-5-ylsulfanyl]-acetic acid methyl ester (255 mg, 60%) was prepared from N-(5-bromo-thiazol-2-yl)-3,5-diisopropoxy-benzamide (399 mg, 1.0 mmol) and methylthioglycolate (212 mg, 2.0 mmol) following the general procedure F.

LC-MS (m/z): 425 (M+1)$^+$; $^1$H NMR (CDCl$_3$, 400 MHz): δ 1.35 (d, 12H), 3.46 (s, 2H), 3.71 (s, 3H), 4.56 (m, 2H), 6.66 (s, 1H), 7.02 (d, 2H), 11.80 (br, 1H) ppm.

Example 13

General Procedure (A)

[2-(3,5-Diisopropoxy-benzoylamino)-thiazol-5-yl-sulfanyl]-acetic acid

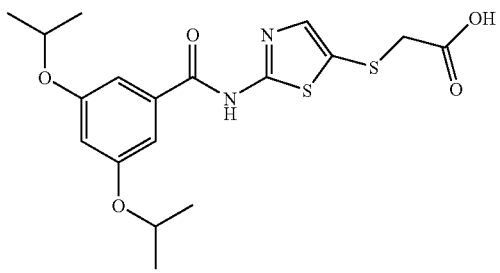

Step A:

[2-(3,5-Diisopropoxy-benzoylamino)-thiazol-5-ylsulfanyl]-acetic acid (159 mg, 75%) was prepared from [2-(3,5-diisopropoxy-benzoylamino)-thiazol-5-ylsulfanyl]-acetic acid methyl ester (212 mg, 0.5 mmol) following the general procedure E.

LC-MS (m/z): 411 (M+1)$^+$; $^1$H NMR (DMSO-d$_6$, 400 MHz): 1.26 (d, 12H), 3.55 (s, 2H), 4.68 (m, 2H), 6.64 (s, 1H), 7.19 (s, 1H), 7.61 (s, 1H), 12.42 (br, 1H) ppm.

Example 14

General Procedure (A)

[2-(3,5-Diisopropoxy-benzoylamino)-thiazol-5-yl-sulfonyl]-acetic acid methyl ester

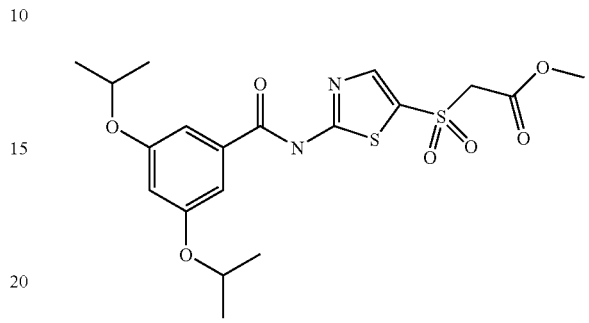

Step A:

[2-(3,5-Diisopropoxy-benzoylamino)-thiazol-5-ylsulfonyl]-acetic acid methyl ester (273 mg, 60%) was prepared from [2-(3,5-diisopropoxy-benzoylamino)-thiazol-5-ylsulfanyl]-acetic acid methyl ester (424 mg, 1.0 mmol) following the general procedure H.

$^1$H NMR (CDCl$_3$, 400 MHz): δ 1.37 (d, 12H), 3.79 (s, 3H), 4.24 (s, 2H), 4.66 (m, 2H), 6.68 (s, 1H), 7.03 (s, 1H), 7.95 (br, 1H), 11.21 (br, 1H) ppm; LC-MS (m/z): 457 (M+1)$^+$.

Example 15

General Procedure (A)

[2-(3,5-Diisopropoxy-benzoylamino)-thiazole-5-sulfonyl]-acetic acid

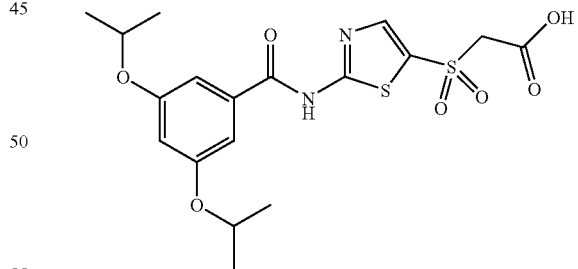

Step A:

[2-(3,5-Diisopropoxy-benzoylamino)-thiazol-5-ylsulfonyl]-acetic acid (189 mg, 85%) was prepared from [2-(3,5-diisopropoxy-benzoylamino)-thiazol-5-ylsulfonyl]-acetic acid methyl ester (228 mg, 0.5 mmol) following the general procedure F.

$^1$H NMR (DMSO-d$_6$, 400 MHz) δ 1.24 (d, 12H), 4.54 (s, 2H), 4.68 (m, 2H), 6.67 (s, 1H), 7.22 (s, 1H), 8.15 (s, 1H), 8.23 (br, 1H), 11.88 (br, 1H) ppm; LC-MS (m/z): 443 (M+1)$^+$.

Example 16

General Procedure (A)

[2-(3,5-Diisopropoxy-benzoylamino)-thiazol-5-yl-sulfanyl]-propionic acid methyl ester

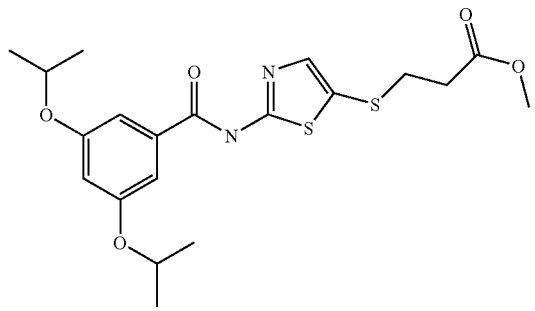

Step A:

[2-(3,5-Diisopropoxy-benzoylamino)-thiazol-5-ylsulfanyl]-propionic acid methyl ester (263 mg, 60%) was prepared from N-(5-bromo-thiazol-2-yl)-3,5-diisopropoxy-benzamide (399 mg, 1.0 mmol) and 3-mercaptopropionic acid methyl ester (240 mg, 2.0 mmol) following general procedure F $^1$H NMR (CDCl$_3$, 400 MHz) δ 1.34 (d, 12H), 2.62 (t, 2H), 2.81 (t, 2H), 3.69 (s, 3H), 4.57 (m, 2H), 6.65 (s, 1H), 6.98 (d, 1H), 7.02 (d, 1H), 7.36 (br, 1H) ppm; LC-MS (m/z): 439 (M+1)$^+$.

Example 17

General Procedure (A)

[2-(3,5-Diisopropoxy-benzoylamino)-thiazol-5-yl-sulfanyl]-propionic acid

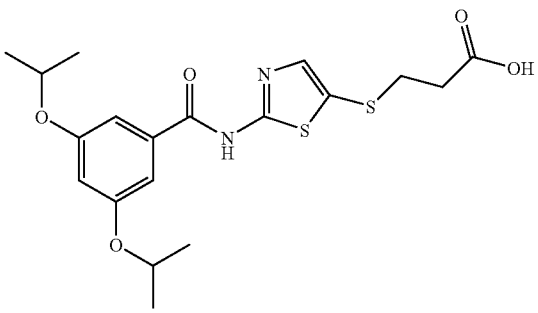

Step A:

[2-(3,5-Diisopropoxy-benzoylamino)-thiazol-5-ylsulfanyl]-acetic acid (170 mg, 80%) was prepared from [2-(3,5-diisopropoxy-benzoylamino)-thiazol-5-ylsulfanyl]-propionic acid methyl ester (219 mg, 0.5 mmol) following general procedure E.

$^1$H NMR (DMSO-d$_6$, 400 MHz) δ1.33 (d, 12H), 2.64 (t, 2H), 2.79 (t, 2H), 4.55 (m, 2H), 6.64 (s, 1H), 7.03 (d, 2H), 8.2 (br, 1H), 11.88 (br, 1H) ppm; LC-MS (m/z): 425 (M+1)$^+$.

Example 18

General Procedure (A)

{2-[3,5-Bis-(2-chloro-benzyloxy)-benzoylamino]-thiazol-5-ylsulfanyl}-acetic acid ethyl ester

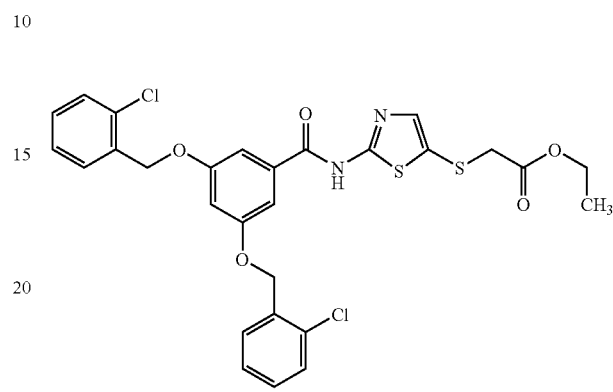

Step A:

The title compound was prepared from 3,5-bis-(2-chloro-benzyloxy)-benzoic acid and (2-amino-thiazol-5-ylsulfanyl)-acetic acid ethyl ester following general procedure A.

LC-MS (m/z): 604 (M+1)$^+$.

Example 19

General Procedure (A)

{2-[3,5-Bis-(2-chloro-benzyloxy)-benzoylamino]-thiazol-5-ylsulfanyl}-acetic acid

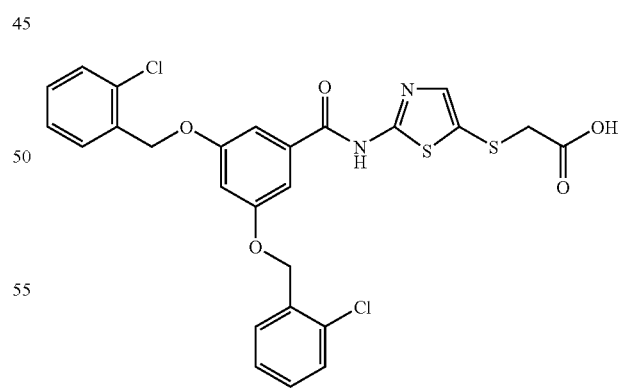

Step A:

The title compound was prepared from the corresponding ethyl ester following general procedure E LC-MS (m/z): 576 (M+1)$^+$.

Example 20

General Procedure (A)

3-{2-[3,5-Bis-(2-chloro-benzyloxy)-benzoylamino]-thiazol-5-ylsulfanyl}-propionic acid ethyl ester

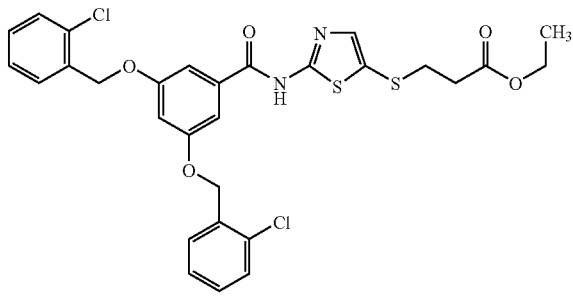

Step A:

The title compound was prepared from 3,5-bis-(2-chlorobenzyloxy)-benzoic acid and (2-amino-thiazol-5-ylsulfanyl)-propionic acid ethyl ester following general procedure A LC-MS (m/z): 618 (M+1)$^+$.

Example 21

General Procedure (A)

3-{2-[3,5-Bis-(2-chloro-benzyloxy)-benzoylamino]-thiazol-5-ylsulfanyl}-propionic acid

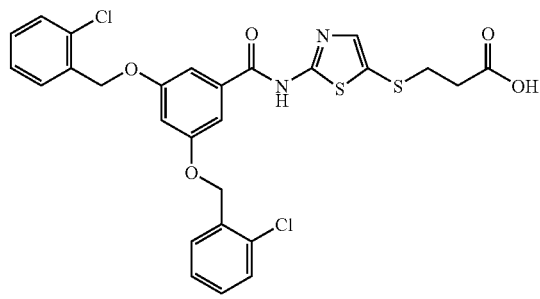

Step A:

The title compound was prepared from the corresponding ethyl ester following general procedure E LC-MS (m/z): 590 (M+1)$^+$.

Example 22

General Procedure (A)

3-{2-[3-(4-Methanesulfonyl-phenoxy)-5-((S)-2-methoxy-1-methyl-ethoxy)-benzoylamino]-thiazol-5-ylsulfanyl}-propionic acid ethyl ester Step A:

The title compound was prepared from 3,5-bis-(2-chlorobenzyloxy)-benzoic acid and (2-amino-thiazol-5-ylsulfanyl)-propionic acid ethyl ester following general procedure A LC-MS (m/z): 595 (M+1)$^+$.

Example 23

General Procedure (A)

3-{2-[3-(4-Methanesulfonyl-phenoxy)-5-((S)-2-methoxy-1-methyl-ethoxy)-benzoylamino]-thiazol-5-ylsulfanyl}-propionic acid Step A:

The title compound was prepared from the corresponding ethyl ester following general procedure E LC-MS (m/z): 567 (M+1)$^+$.

Example 24

General Procedure (A)

{2-[3-(4-Methanesulfonyl-phenoxy)-5-((S)-2-methoxy-1-methyl-ethoxy)-benzoylamino]-thiazol-5-ylsulfanyl}-acetic acid ethyl ester

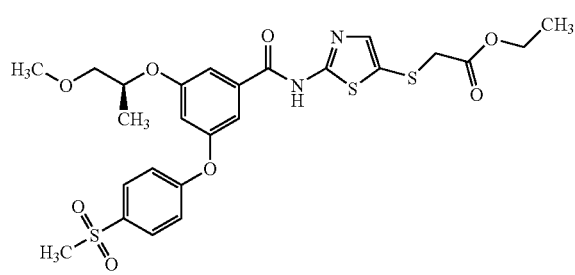

Step A:

The title compound was prepared from 3-(4-methanesulfonyl-phenoxy)-5-((S)-2-methoxy-1-methyl-ethoxy)-benzoic acid and (2-amino-thiazol-5-ylsulfanyl)-acetic acid ethyl ester following general procedure A LC-MS (m/z): 581 (M+1)$^+$.

Example 25

General Procedure (A)

{2-[3-(4-Methanesulfonyl-phenoxy)-5-((S)-2-methoxy-1-methyl-ethoxy)-benzoylamino]-thiazol-5-ylsulfanyl}-acetic acid

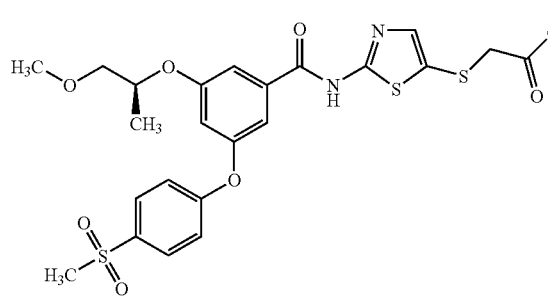

Step A:

The title compound was prepared from the corresponding ethyl ester following general procedure E LC-MS (m/z): 553 (M+1)$^+$.

Example 26

General Procedure (A)

{2-[3-(4-Fluoro-phenoxy)-5-((S)-2-methoxy-1-methyl-ethoxy)-benzoylamino]-thiazol-5-ylsulfanyl}-acetic acid ethyl ester

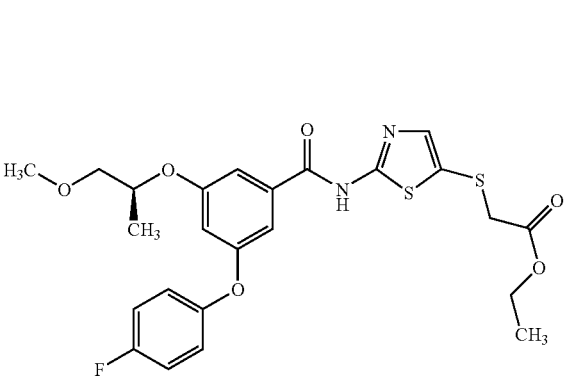

Step A:

The title compound was prepared from 3-(4-fluoro-phenoxy)-5-((S)-2-methoxy-1-methyl-ethoxy)-benzoic acid and (2-amino-thiazol-5-ylsulfanyl)-acetic acid ethyl ester following general procedure A LC-MS (m/z): 521 (M+1)$^+$.

Example 27

General Procedure (A)

{2-[3-(4-Fluoro-phenoxy)-5-((S)-2-methoxy-1-methyl-ethoxy)-benzoylamino]-thiazol-5-ylsulfanyl}-acetic acid

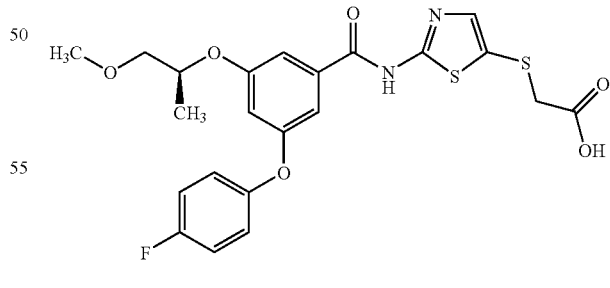

Step A:

The title compound was prepared from the corresponding ethyl ester following general procedure E LC-MS (m/z): 493 (M+1)$^+$.

Example 28

General Procedure (A)

3-{2-[3-(4-Fluoro-phenoxy)-5-((S)-2-methoxy-1-methyl-ethoxy)-benzoylamino]-thiazol-5-ylsulfanyl}-propionic acid ethyl ester

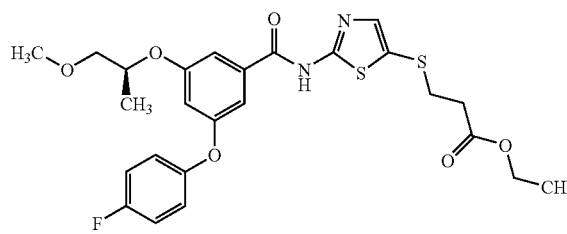

Step A:

The title compound was prepared from 3-(4-fluoro-phenoxy)-5-((S)-2-methoxy-1-methyl-ethoxy)-benzoic acid and (2-amino-thiazol-5-ylsulfanyl)-propionic acid ethyl ester following general procedure A LC-MS (m/z): 535 (M+1)$^+$.

Example 29

General Procedure (A)

3-{2-[3-(4-Fluoro-phenoxy)-5-((S)-2-methoxy-1-methyl-ethoxy)-benzoylamino]-thiazol-5-ylsulfanyl}-propionic acid

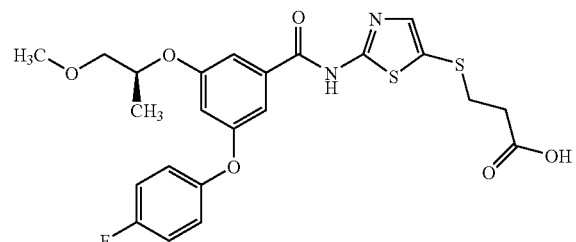

Step A:

The title compound was prepared from the corresponding ethyl ester following general procedure E LC-MS (m/z): 507 (M+1)$^+$.

Example 30

General Procedure (A)

{2-[3-(3-Fluoro-phenoxy)-5-((S)-2-methoxy-1-methyl-ethoxy)-benzoylamino]-thiazol-5-ylsulfanyl}-acetic acid ethyl ester

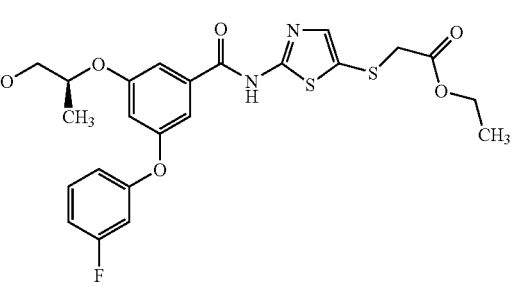

Step A:

The title compound was prepared from 3-(3-fluoro-phenoxy)-5-((S)-2-methoxy-1-methyl-ethoxy)-benzoic acid and (2-amino-thiazol-5-ylsulfanyl)-acetic acid ethyl ester following general procedure A LC-MS (m/z): 525 (M+1)$^+$.

Example 31

General Procedure (A)

{2-[3-(3-Fluoro-phenoxy)-5-((S)-2-methoxy-1-methyl-ethoxy)-benzoylamino]-thiazol-5-ylsulfanyl}-acetic acid

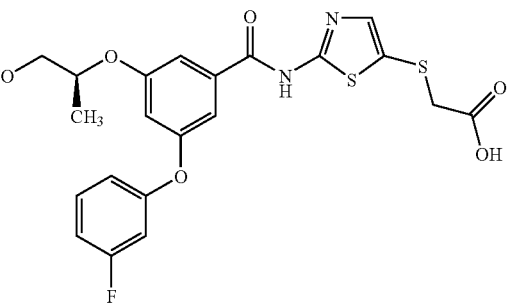

Step A:

The title compound was prepared from the corresponding ethyl ester following general procedure E LC-MS (m/z): 493 (M+1)$^+$.

Example 32

General Procedure (A)

3-{2-[3-(3-Fluoro-phenoxy)-5-((S)-2-methoxy-1-methyl-ethoxy)-benzoylamino]-thiazol-5-ylsulfanyl}-propionic acid ethyl ester

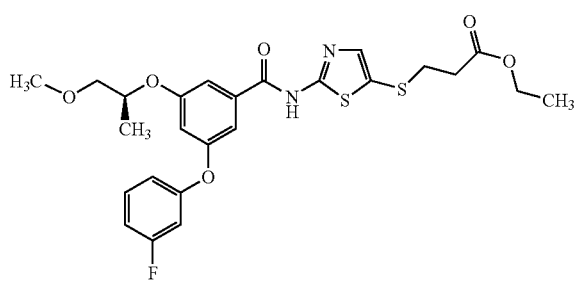

Step A:

The title compound was prepared from 3-(3-fluoro-phenoxy)-5-((S)-2-methoxy-1-methyl-ethoxy)-benzoic acid and (2-amino-thiazol-5-ylsulfanyl)-propionic acid ethyl ester following general procedure A LC-MS (m/z): 535 (M+1)$^+$.

Example 33

General Procedure (A)

3-{2-[3-(3-Fluoro-phenoxy)-5-((S)-2-methoxy-1-methyl-ethoxy)-benzoylamino]-thiazol-5-ylsulfanyl}-propionic acid

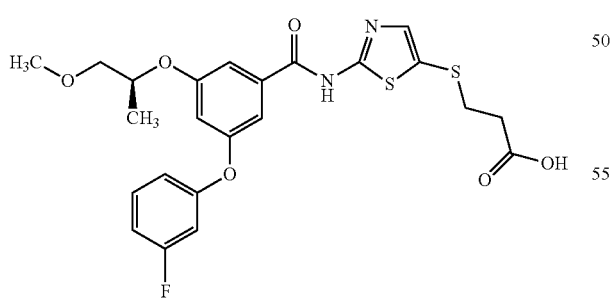

Step A:

The title compound was prepared from the corresponding ethyl ester following general procedure E LC-MS (m/z): 507 (M+1)$^+$.

Example 34

General Procedure (A)

{2-[3-((S)-2-Methoxy-1-methyl-ethoxy)-5-phenoxy-benzoylamino]-thiazol-5-ylsulfanyl}-acetic acid ethyl ester

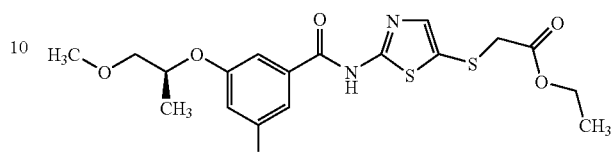

Step A:

The title compound was prepared from 3-((S)-2-methoxy-1-methyl-ethoxy)-5-phenoxy benzoic acid and (2-amino-thiazol-5-ylsulfanyl)-acetic acid ethyl ester following general procedure A LC-MS (m/z): 503 (M+1)$^+$.

Example 35

General Procedure (A)

{2-[3-((S)-2-Methoxy-1-methyl-ethoxy)-5-phenoxy-benzoylamino]-thiazol-5-ylsulfanyl}-acetic acid

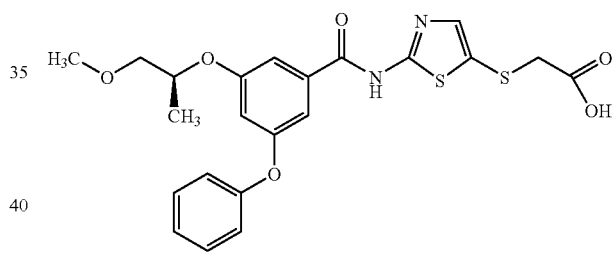

Step A:

The title compound was prepared from the corresponding ethyl ester following general procedure E LC-MS (m/z): 475 (M+1)$^+$.

Example 36

General Procedure (A)

3-{2-[3-((S)-2-Methoxy-1-methyl-ethoxy)-5-phenoxy-benzoylamino]-thiazol-5-ylsulfanyl}-propionic acid ethyl ester

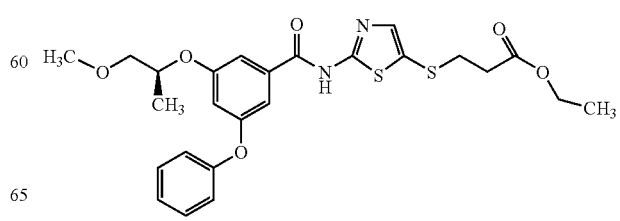

Step A:

The title compound was prepared from 3-((S)-2-methoxy-1-methyl-ethoxy)-5-phenoxy benzoic acid and (2-amino-thiazol-5-ylsulfanyl)-propionic acid ethyl ester following general procedure A LC-MS (m/z): 517 (M+1)$^+$.

Example 37

General Procedure (A)

3-{2-[3-((S)-2-Methoxy-1-methyl-ethoxy)-5-phenoxy-benzoylamino]-thiazol-5-ylsulfanyl}-propionic acid

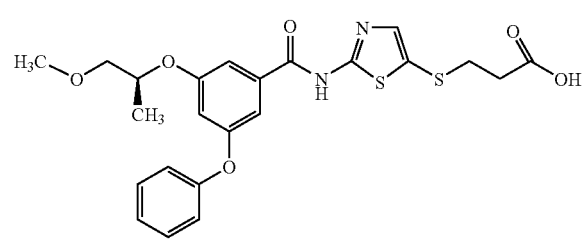

Step A:

The title compound was prepared from the corresponding ethyl ester following general procedure E LC-MS (m/z): 489 (M+1)$^+$.

Example 38

General Procedure (A)

{2-[3-((S)-2-Methoxy-1-methyl-ethoxy)-5-(3-methoxy-phenoxy)-benzoylamino]-thiazol-5-ylsulfanyl}-acetic acid ethyl ester

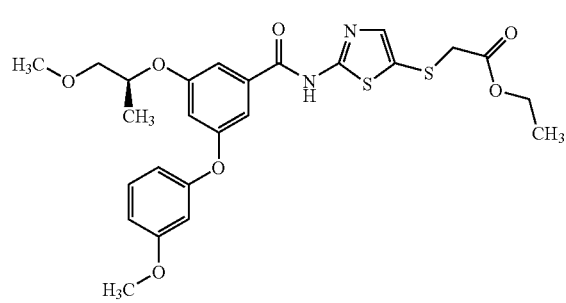

Step A:

The title compound was prepared from 3-((S)-2-methoxy-1-methyl-ethoxy)-5-(3-methoxy-phenoxy)-benzoic acid and (2-amino-thiazol-5-ylsulfanyl)-acetic acid ethyl ester following general procedure A LC-MS (m/z): 533 (M+1)$^+$.

Example 39

General Procedure (A)

{2-[3-((S)-2-Methoxy-1-methyl-ethoxy)-5-(3-methoxy-phenoxy)-benzoylamino]-thiazol-5-ylsulfanyl}-acetic acid

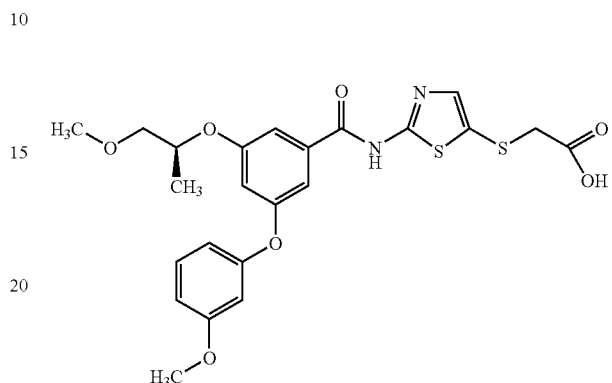

Step A:

The title compound was prepared from the corresponding ethyl ester following general procedure E LC-MS (m/z): 505 (M+1)$^+$.

Example 40

General Procedure (A)

3-{2-[3-((S)-2-Methoxy-1-methyl-ethoxy)-5-(3-methoxy-phenoxy)-benzoylamino]-thiazol-5-ylsulfanyl}-propionic acid ethyl ester

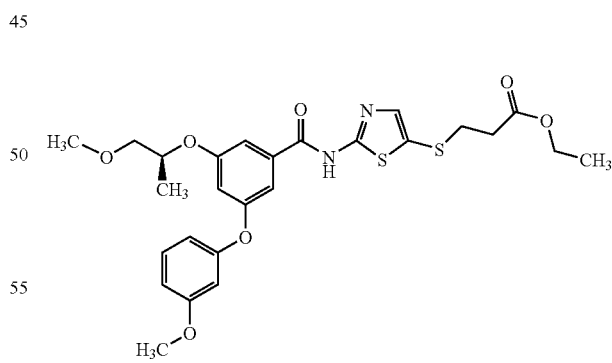

Step A:

The title compound was prepared from 3-((S)-2-methoxy-1-methyl-ethoxy)-5-(3-methoxy-phenoxy phenoxy benzoic acid and (2-amino-thiazol-5-ylsulfanyl)-propionic acid ethyl ester following general procedure A LC-MS (m/z): 547 (M+1)$^+$.

Example 41

General Procedure (A)

3-{2-[3-((S)-2-Methoxy-1-methyl-ethoxy)-5-(3-methoxy-phenoxy)-benzoylamino]-thiazol-5-ylsulfanyl}-propionic acid

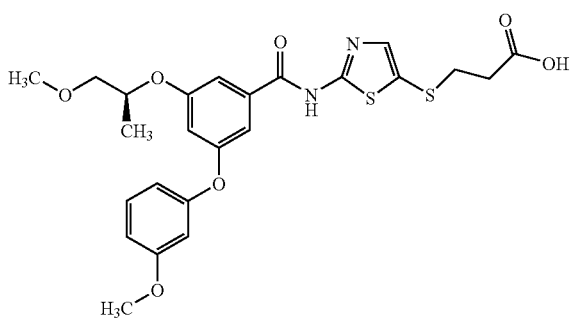

Step A:

The title compound was prepared from the corresponding ethyl ester following general procedure E LC-MS (m/z): 519 (M+1)$^+$.

Example 42

General Procedure (A)

{2-[3-((S)-2-Methoxy-1-methyl-ethoxy)-5-(4-methoxy-phenoxy)-benzoylamino]-thiazol-5-ylsulfanyl}-acetic acid ethyl ester

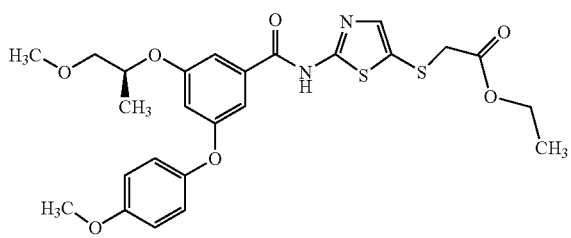

Step A:

The title compound was prepared from {2-[3-((S)-2-methoxy-1-methyl-ethoxy)-5-(4-methoxy-phenoxy)-benzoic acid and (2-amino-thiazol-5-ylsulfanyl)-acetic acid ethyl ester following general procedure A LC-MS (m/z): 533 (M+1)$^+$.

Example 43

General Procedure (A)

{2-[3-((S)-2-Methoxy-1-methyl-ethoxy)-5-(4-methoxy-phenoxy)-benzoylamino]-thiazol-5-ylsulfanyl}-acetic acid

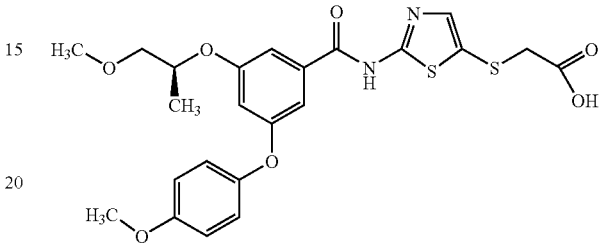

Step A:

The title compound was prepared from the corresponding ethyl ester following general procedure E LC-MS (m/z): 505 (M+1)$^+$.

Example 44

General Procedure (A)

3-{2-[3-((S)-2-Methoxy-1-methyl-ethoxy)-5-(4-methoxy-phenoxy)-benzoylamino]-thiazol-5-ylsulfanyl}-propionic acid ethyl ester

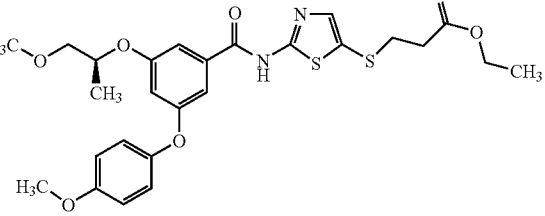

Step A:

The title compound was prepared from 3-((S)-2-Methoxy-1-methyl-ethoxy)-5-(4-methoxy-phenoxy)-benzoic acid and (2-amino-thiazol-5-ylsulfanyl)-propionic acid ethyl ester following general procedure A LC-MS (m/z): 547 (M+1)$^+$.

Example 45

General Procedure (A)

3-{2-[3-((S)-2-Methoxy-1-methyl-ethoxy)-5-(4-methoxy-phenoxy)-benzoylamino]-thiazol-5-ylsulfanyl}-propionic acid

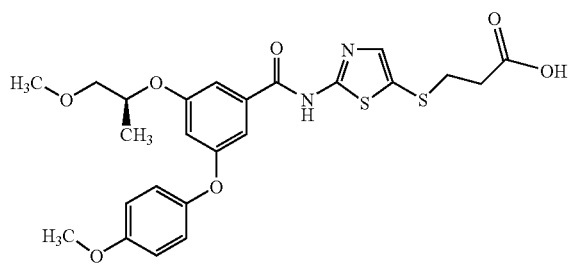

Step A:
The title compound was prepared from the corresponding ethyl ester following general procedure E
LC-MS (m/z): 519 (M+1)$^+$.

Example 46

General Procedure (A)

{2-[3-Benzyloxy-5-((S)-2-methoxy-1-methyl-ethoxy)-benzoylamino]-thiazol-5-ylsulfanyl}-acetic acid ethyl ester

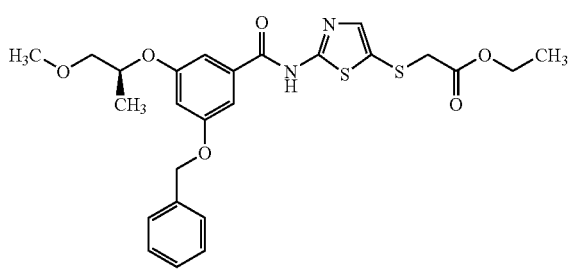

Step A:
The title compound was prepared from 3-benzyloxy-5-((S)-2-methoxy-1-methylethoxy)-benzoic acid and (2-amino-thiazol-5-ylsulfanyl)-acetic acid ethyl ester following general procedure A
LC-MS (m/z): 517 (M+1)$^+$.

Example 47

General Procedure (A)

{2-[3-Benzyloxy-5-((S)-2-methoxy-1-methyl-ethoxy)-benzoylamino]-thiazol-5-ylsulfanyl}-acetic acid

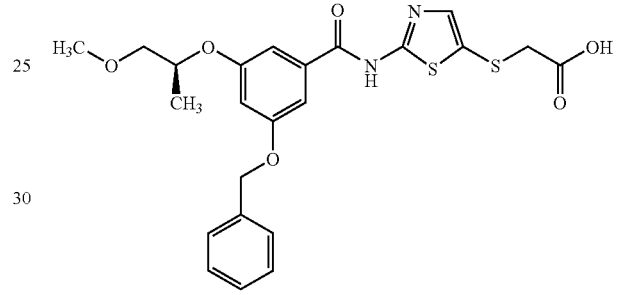

Step A:
The title compound was prepared from the corresponding ethyl ester following general procedure E
LC-MS (m/z): 489 (M+1)$^+$.

Example 48

General Procedure (A)

3-{2-[3-Benzyloxy-5-((S)-2-methoxy-1-methyl-ethoxy)-benzoylamino]-thiazol-5-ylsulfanyl}-propionic acid ethyl ester

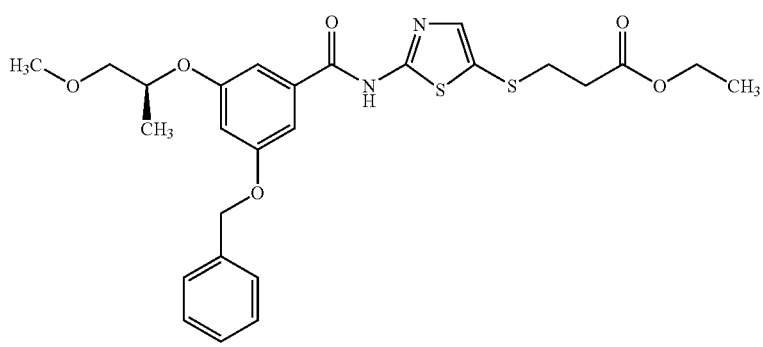

Step A:
The title compound was prepared from 3-benzyloxy-5-((S)-2-methoxy-1-methylethoxy)-benzoic acid and (2-amino-thiazol-5-ylsulfanyl)-propionic acid ethyl ester following general procedure A
LC-MS (m/z): 531 (M+1)$^+$.

Example 49

General Procedure (A)

3-{2-[3-Benzyloxy-5-((S)-2-methoxy-1-methyl-ethoxy)-benzoylamino]-thiazol-5-ylsulfanyl}-propionic acid

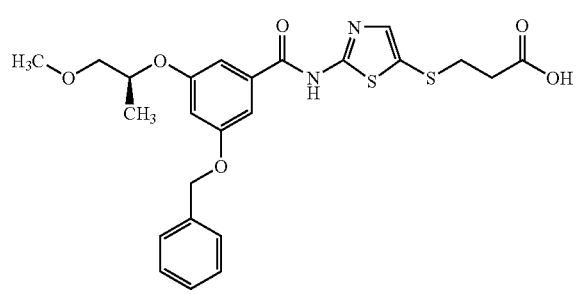

Step A:
The title compound was prepared from the corresponding ethyl ester following general procedure E
LC-MS (m/z): 503 (M+1)$^+$.

Example 50

General Procedure (A)

{2-[3-((S)-2-Methoxy-1-methyl-ethoxy)-5-phenethyloxy-benzoylamino]-thiazol-5-ylsulfanyl}-acetic acid ethyl ester

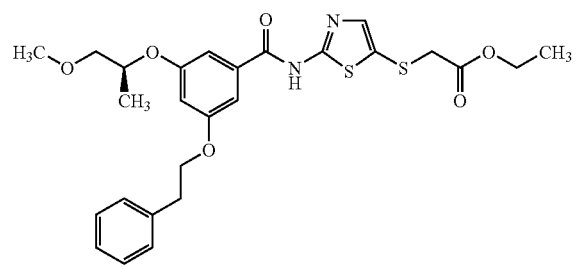

Step A:
The title compound was prepared from 3-((S)-2-methoxy-1-methyl-ethoxy)-5-phenethyloxy benzoic acid and (2-amino-thiazol-5-ylsulfanyl)-acetic acid ethyl ester following general procedure A
LC-MS (m/z): 531 (M+1)$^+$.

Example 51

General Procedure (A)

{2-[3-((S)-2-Methoxy-1-methyl-ethoxy)-5-phenethyloxy-benzoylamino]-thiazol-5-ylsulfanyl}-acetic acid

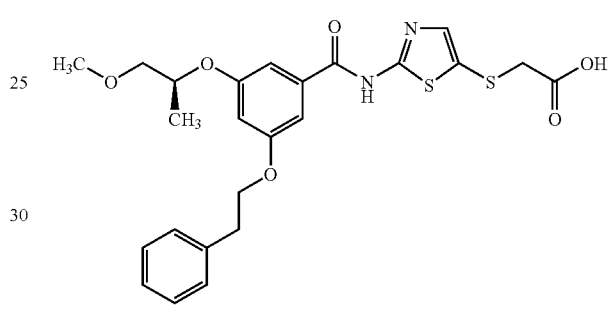

Step A:
The title compound was prepared from the corresponding ethyl ester following general procedure E
LC-MS (m/z): 503 (M+1)$^+$.

Example 52

General Procedure (A)

3-{2-[3-((S)-2-Methoxy-1-methyl-ethoxy)-5-phenethyloxy-benzoylamino]-thiazol-5-ylsulfanyl}-propionic acid ethyl ester

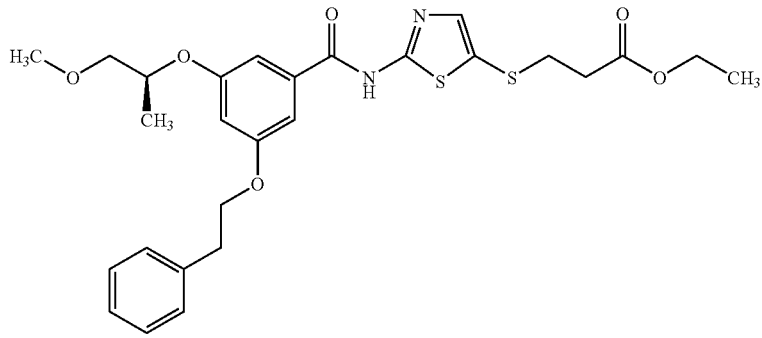

Step A:

The title compound was prepared from 3-((S)-2-methoxy-1-methyl-ethoxy)-5-phenethyloxy-benzoic acid and (2-amino-thiazol-5-ylsulfanyl)-propionic acid ethyl ester following general procedure A LC-MS (m/z): 545 (M+1)$^+$.

Example 53

General Procedure (A)

3-{2-[3-((S)-2-Methoxy-1-methyl-ethoxy)-5-phenethyloxy-benzoylamino]-thiazol-5-ylsulfanyl}-propionic acid

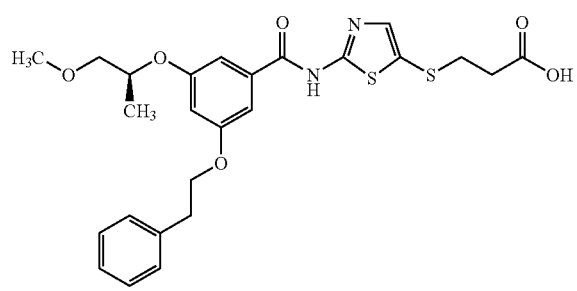

Step A:

The title compound was prepared from the corresponding ethyl ester following general procedure E LC-MS (m/z): 517 (M+1)$^+$.

Example 54

General Procedure (A)

{2-[3-(3,5-Difluoro-phenoxy)-5-((S)-2-methoxy-1-methyl-ethoxy)-benzoylamino]-thiazol-5-ylsulfanyl}-acetic acid ethyl ester

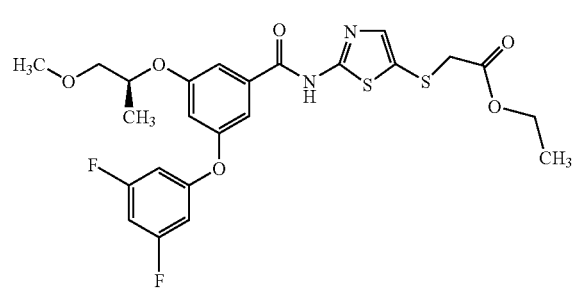

Step A:

The title compound was prepared from 3-(3,5-difluoro-phenoxy)-5-((S)-2-methoxy-1-methyl-ethoxy)-benzoic acid and (2-amino-thiazol-5-ylsulfanyl)-acetic acid ethyl ester following general procedure A LC-MS (m/z): 539 (M+1)$^+$.

Example 55

General Procedure (A)

{2-[3-(3,5-Difluoro-phenoxy)-5-((S)-2-methoxy-1-methyl-ethoxy)-benzoylamino]-thiazol-5-ylsulfanyl}-acetic acid

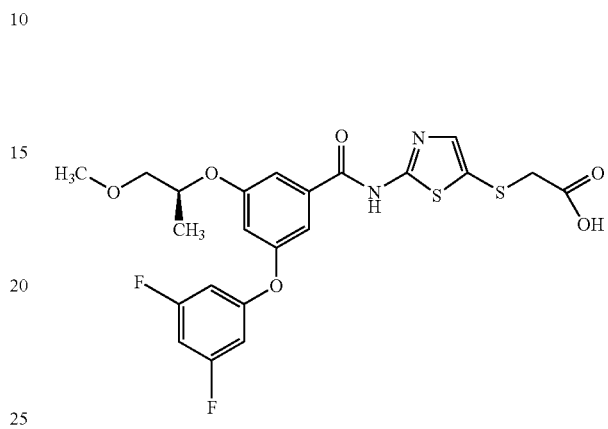

Step A:

The title compound was prepared from the corresponding ethyl ester following general procedure E LC-MS (m/z): 511 (M+1)$^+$.

Example 56

General Procedure (A)

3-{2-[3-(3,5-Difluoro-phenoxy)-5-((S)-2-methoxy-1-methyl-ethoxy)-benzoylamino]-thiazol-5-ylsulfanyl}-propionic acid ethyl ester

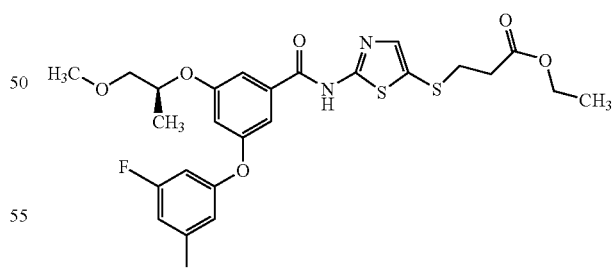

Step A:

The title compound was prepared from 3-(3,5-difluoro-phenoxy)-5-((S)-2-methoxy-1-methyl-ethoxy)-benzoic acid and (2-amino-thiazol-5-ylsulfanyl)-propionic acid ethyl ester following general procedure A LC-MS (m/z): 553 (M+1)$^+$.

Example 57

General Procedure (A)

3-{2-[3-(3,5-Difluoro-phenoxy)-5-((S)-2-methoxy-1-methyl-ethoxy)-benzoylamino]-thiazol-5-ylsulfanyl}-propionic acid

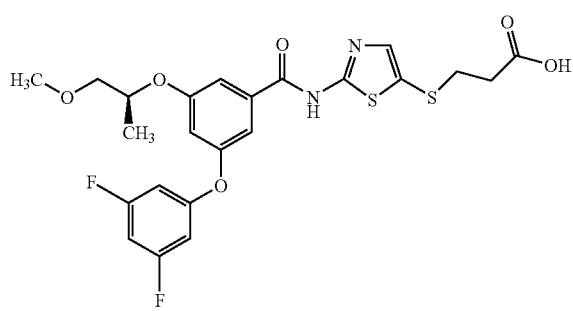

Step A:

The title compound was prepared from the corresponding ethyl ester following general procedure E LC-MS (m/z): 525 (M+1)$^+$.

Example 58

General Procedure (A)

{2-[3-(3,4-Difluoro-phenoxy)-5-((S)-2-methoxy-1-methyl-ethoxy)-benzoylamino]-thiazol-5-ylsulfanyl}-acetic acid ethyl ester

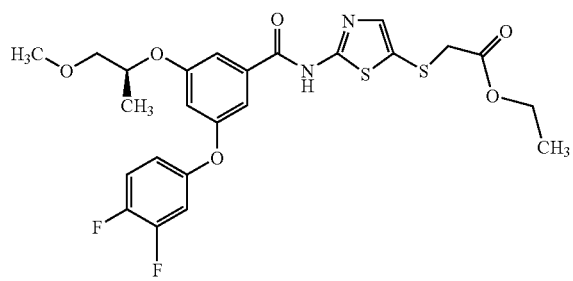

Step A:

The title compound was prepared from 3-(3,4-Difluoro-phenoxy)-5-((S)-2-methoxy-1-methyl-ethoxy)-benzoic acid and (2-amino-thiazol-5-ylsulfanyl)-acetic acid ethyl ester following general procedure A LC-MS (m/z): 539 (M+1)$^+$.

Example 59

General Procedure (A)

{2-[3-(3,4-Difluoro-phenoxy)-5-((S)-2-methoxy-1-methyl-ethoxy)-benzoylamino]-thiazol-5-ylsulfanyl}-acetic acid

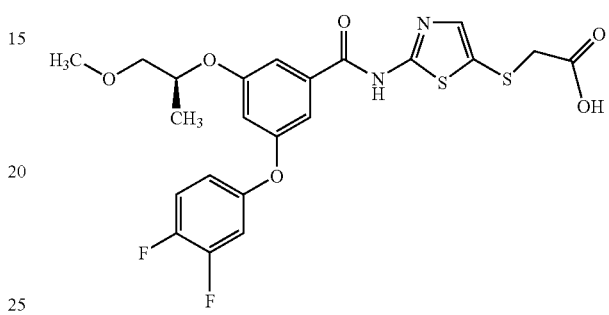

Step A:

The title compound was prepared from the corresponding ethyl ester following general procedure E LC-MS (m/z): 511 (M+1)$^+$.

Example 60

General Procedure (A)

3-{2-[3-(3,4-Difluoro-phenoxy)-5-((S)-2-methoxy-1-methyl-ethoxy)-benzoylamino]-thiazol-5-ylsulfanyl}-propionic acid ethyl ester

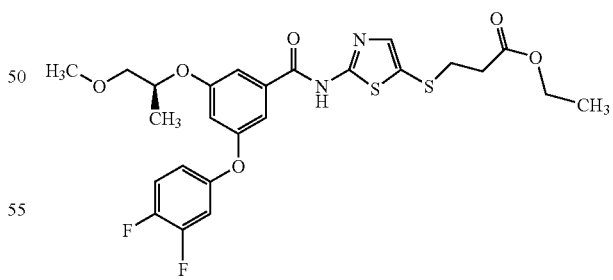

Step A:

The title compound was prepared from 3-(3,4-difluoro-phenoxy)-5-((S)-2-methoxy-1-methyl-ethoxy)-benzoic acid and (2-amino-thiazol-5-ylsulfanyl)-propionic acid ethyl ester following general procedure A LC-MS (m/z): 533 (M+1)$^+$.

Example 61

General Procedure (A)

3-{2-[3-(3,4-Difluoro-phenoxy)-5-((S)-2-methoxy-1-methyl-ethoxy)-benzoylamino]-thiazol-5-ylsulfanyl}-propionic acid

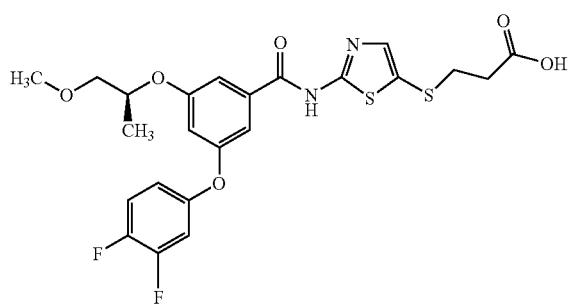

Step A:

The title compound was prepared from the corresponding ethyl ester following general procedure E LC-MS (m/z): 525 (M+1)$^+$.

Example 62

General Procedure (A)

{2-[3-((S)-2-Methoxy-1-methyl-ethoxy)-5-(4-trifluoromethyl-phenoxy)-benzoylamino]-thiazol-5-ylsulfanyl}-acetic acid ethyl ester

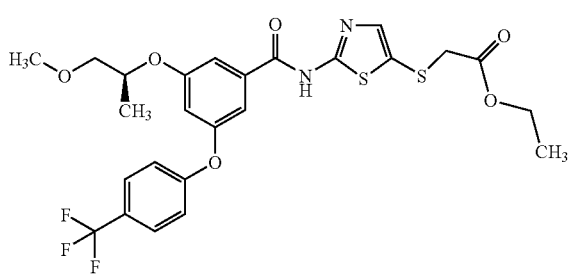

Step A:

The title compound was prepared from 3-((S)-2-methoxy-1-methyl-ethoxy)-5-(4-trifluoromethyl-phenoxy)-benzoic acid and (2-amino-thiazol-5-ylsulfanyl)-acetic acid ethyl ester following general procedure A LC-MS (m/z): 571 (M+1)$^+$.

Example 63

General Procedure (A)

{2-[3-((S)-2-Methoxy-1-methyl-ethoxy)-5-(4-trifluoromethyl-phenoxy)-benzoylamino]-thiazol-5-ylsulfanyl}-acetic acid

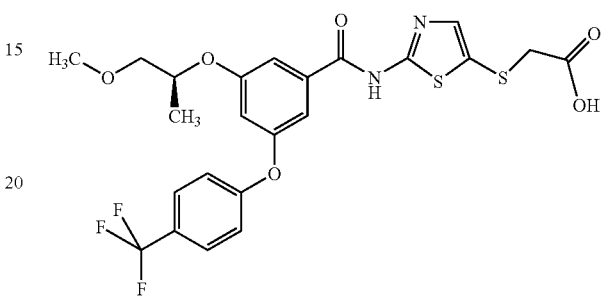

Step A:

The title compound was prepared from the corresponding ethyl ester following general procedure E LC-MS (m/z): 543 (M+1)$^+$.

Example 64

General Procedure (A)

3-{2-[3-((S)-2-Methoxy-1-methyl-ethoxy)-5-(4-trifluoromethyl-phenoxy)-benzoylamino]-thiazol-5-ylsulfanyl}-propionic acid ethyl ester

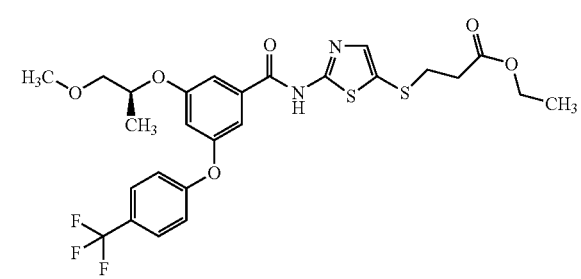

Step A:

The title compound was prepared from 3-((S)-2-methoxy-1-methyl-ethoxy)-5-(4-trifluoromethyl-phenoxy)-benzoic acid and (2-amino-thiazol-5-ylsulfanyl)-propionic acid ethyl ester following general procedure A LC-MS (m/z): 585 (M+1)$^+$.

Example 65

General Procedure (A)

{2-[3-((S)-2-Methoxy-1-methyl-ethoxy)-5-(thiophen-2-ylmethoxy)-benzoylamino]-thiazol-5-ylsulfanyl}-acetic acid ethyl ester

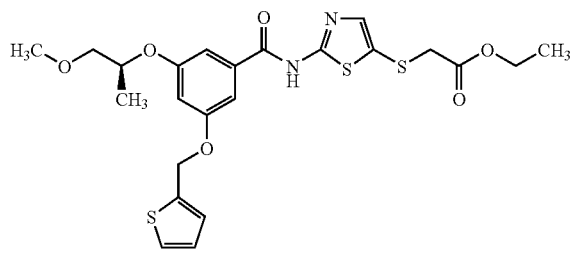

Step A:

The title compound was prepared from 3-((S)-2-methoxy-1-methyl-ethoxy)-5-(thiophen-2-ylmethoxy)-benzoic acid and (2-amino-thiazol-5-ylsulfanyl)-acetic acid ethyl ester following general procedure A LC-MS (m/z): 523 (M+1)$^+$.

Example 66

General Procedure (A)

{2-[3-((S)-2-Methoxy-1-methyl-ethoxy)-5-(thiophen-2-ylmethoxy)-benzoylamino]-thiazol-5-ylsulfanyl}-acetic acid

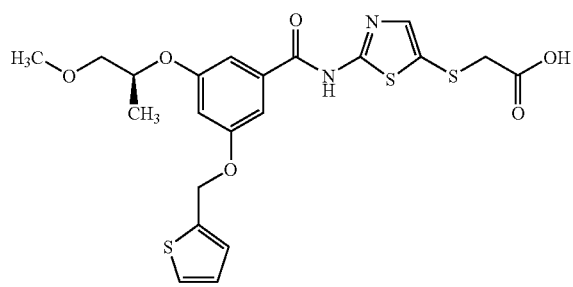

Step A:

The title compound was prepared from the corresponding ethyl ester following general procedure E LC-MS (m/z): 495 (M+1)$^+$.

Example 67

General Procedure (A)

{2-[3-(2-Fluoro-1-fluoromethyl-ethoxy)-5-(4-fluoro-phenoxy)-benzoylamino]-thiazol-5-ylsulfanyl}-acetic acid ethyl ester

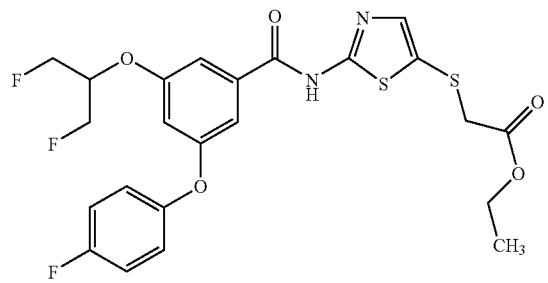

Step A:

The title compound was prepared from 3-(2-fluoro-1-fluoromethyl-ethoxy)-5-(4-fluoro-phenoxy)-benzoic acid and (2-amino-thiazol-5-ylsulfanyl)-acetic acid ethyl ester following general procedure A LC-MS (m/z): 527 (M+1)$^+$.

Example 68

General Procedure (A)

{2-[3-(2-Fluoro-1-fluoromethyl-ethoxy)-5-(4-fluoro-phenoxy)-benzoylamino]-thiazol-5-ylsulfanyl}-acetic acid

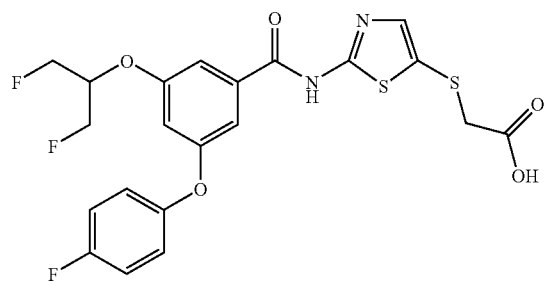

Step A:

The title compound was prepared from the corresponding ethyl ester following general procedure E LC-MS (m/z): 499 (M+1)$^+$.

Example 69

General Procedure (A)

{2-[3-((R)-sec-Butoxy)-5-(4-fluoro-phenoxy)-benzoylamino]-thiazol-5-ylsulfanyl}-acetic acid ethyl ester

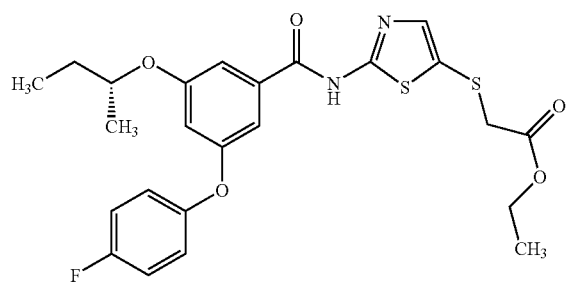

Step A:

The title compound was prepared from 3-((R)-sec-butoxy)-5-(4-fluoro-phenoxy)benzoic acid and (2-amino-thiazol-5-ylsulfanyl)-acetic acid ethyl ester following general procedure A LC-MS (m/z): 505 (M+1)$^+$.

Example 70

General Procedure (A)

{2-[3-Cyclopentyloxy-5-(4-fluoro-phenoxy)-benzoylamino]-thiazol-5-ylsulfanyl}-acetic acid ethyl ester

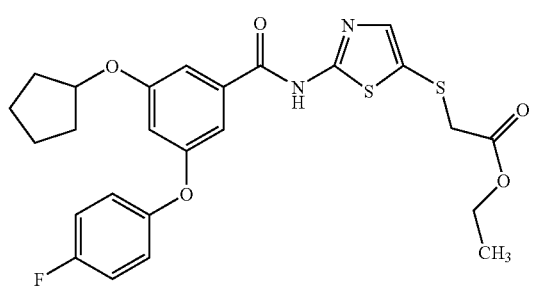

Step A:

The title compound was prepared from 3-cyclopentyloxy-5-(4-fluoro-phenoxy)benzoic acid and (2-amino-thiazol-5-ylsulfanyl)-acetic acid ethyl ester following general procedure A LC-MS (m/z): 517 (M+1)$^+$.

Example 71

General Procedure (A)

{2-[3-(4-Fluoro-phenoxy)-5-(3-methyl-butoxy)-benzoylamino]-thiazol-5-ylsulfanyl}-acetic acid ethyl ester

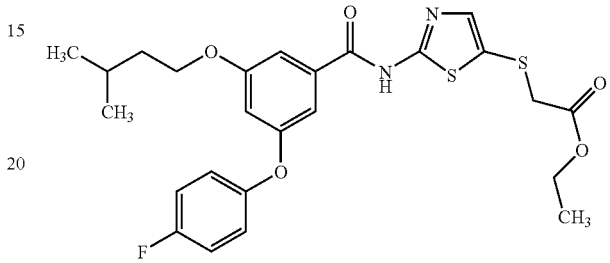

Step A:

The title compound was prepared from 3-(4-fluoro-phenoxy)-5-(3-methyl-butoxy)-)-benzoic acid and (2-amino-thiazol-5-ylsulfanyl)-acetic acid ethyl ester following general procedure A LC-MS (m/z): 519 (M+1)$^+$.

Example 72

General Procedure (A)

{2-[3-(4-Fluoro-phenoxy)-5-isobutoxy-benzoylamino]-thiazol-5-ylsulfanyl}-acetic acid ethyl ester

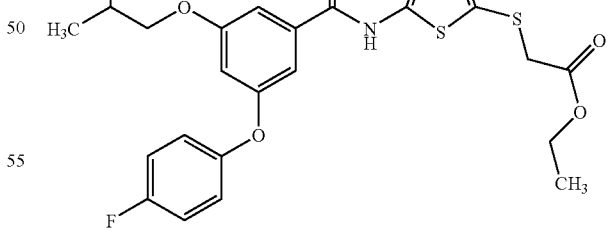

Step A:

The title compound was prepared from 3-(4-fluoro-phenoxy)-5-isobutoxy-benzoic acid and (2-amino-thiazol-5-ylsulfanyl)-acetic acid ethyl ester following general procedure A LC-MS (m/z): 505 (M+1)$^+$.

Example 73

General Procedure (A)

3-{2-[3-((S)-2-Methoxy-1-methyl-ethoxy)-5-(thiophen-2-ylmethoxy)-benzoylamino]-thiazol-5-ylsulfanyl}-propionic acid ethyl ester

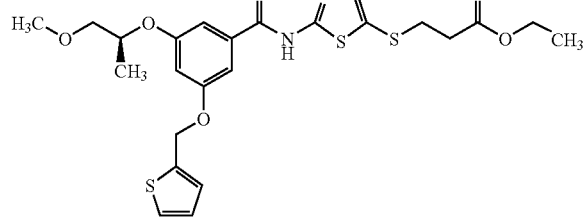

Step A:

The title compound was prepared from 3-((S)-2-methoxy-1-methyl-ethoxy)-5-(thiophen-2-ylmethoxy)-benzoic acid and (2-amino-thiazol-5-ylsulfanyl)-acetic acid ethyl ester following general procedure A LC-MS (m/z): 537 (M+1)$^+$.

Example 74

General Procedure (A)

{2-[3-((S)-2-Methoxy-1-methyl-ethoxy)-5-(thiophen-3-ylmethoxy)-benzoylamino]-thiazol-5-ylsulfanyl}-acetic acid ethyl ester

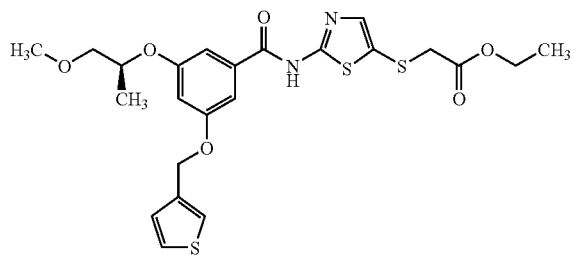

Step A:

The title compound was prepared from 3-((S)-2-methoxy-1-methyl-ethoxy)-5-(thiophen-3-ylmethoxy)-benzoic acid and (2-amino-thiazol-5-ylsulfanyl)-acetic acid ethyl ester following general procedure A LC-MS (m/z): 523 (M+1)$^+$.

Example 75

General Procedure (A)

[2-(3,5-Diisopropoxy-benzoylamino)-thiazol-4-ylmethylsulfanyl]-acetic acid

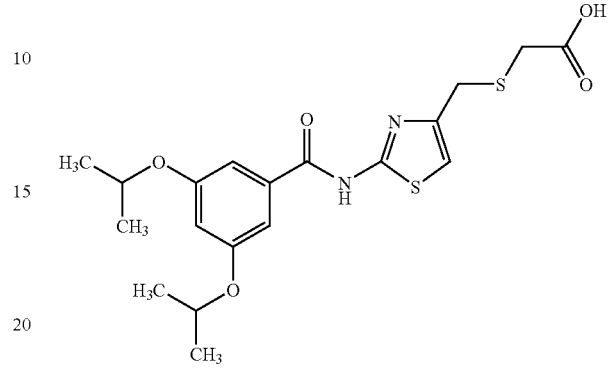

Step A:

[2-(3,5-Diisopropoxy-benzoylamino)-thiazol-4-ylmethylsulfanyl]-acetic acid methyl ester was prepared from 3,5-diisopropoxy-benzoic acid and 3-(2-amino-thiazol-4-ylmethylsulfanyl)-acetic acid methyl ester following general procedure A.

Step B:

[2-(3,5-Diisopropoxy-benzoylamino)-thiazol-4-ylmethylsulfanyl]-acetic acid methyl ester was hydrolysed following general procedure A to give the title compound.

LC-MS (m/z): 425 (M+1)$^+$.

Example 76

General Procedure (A)

[2-(3-Isopropoxy-5-phenoxy-benzoylamino)-thiazol-4-ylmethylsulfanyl]-acetic acid

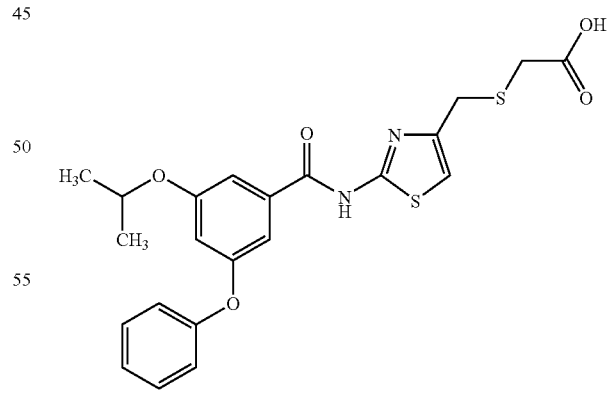

Step A:

[2-(3-Isopropoxy-5-phenoxy-benzoylamino)-thiazol-4-ylmethylsulfanyl]-acetic acid-methyl ester was prepared from 3-isopropoxy-5-phenoxy-benzoic acid and 3-(2-amino-thiazol-4-ylmethylsulfanyl)-acetic acid methyl ester following general procedure A.

Step B:

[2-(3-Isopropoxy-5-phenoxy-benzoylamino)-thiazol-4-ylmethylsulfanyl]-acetic acid methyl ester was hydrolysed following general procedure A to give the title compound.

LC-MS (m/z): 459 (M+1)$^+$.

Example 77

General Procedure (B)

3-[2-(3,5-Diisopropoxy-benzoylamino)-thiazol-4-ylmethylsulfanyl]-propionic acid

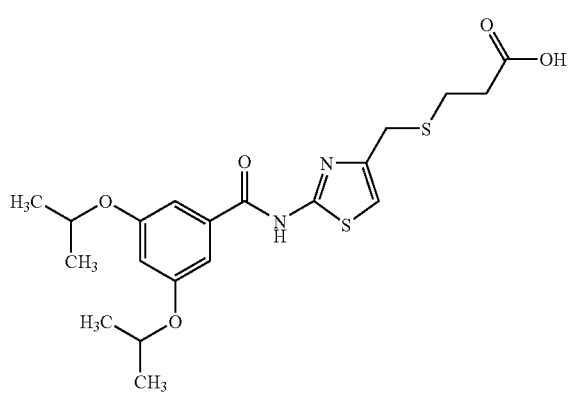

Step A:

3-[2-(3,5-Diisopropoxy-benzoylamino)-thiazol-4-ylmethylsulfanyl]-propionic acid ethyl ester was prepared from 3,5-diisopropoxy-benzoic acid and 3-(2-amino-thiazol-4-yl-methylsulfanyl)-propionic acid ethyl ester following general procedure A.

Step B:

3-[2-(3,5-Diisopropoxy-benzoylamino)-thiazol-4-ylmethylsulfanyl]-propionic acid ethyl ester was hydrolysed following general procedure A. to give the title compound.

LC-MS (m/z): 439 (M+1)$^+$.

Example 78

General Procedure (A)

3-[2-(3-Isopropoxy-5-phenoxy-benzoylamino)-thiazol-4-ylmethylsulfanyl]-propionic acid

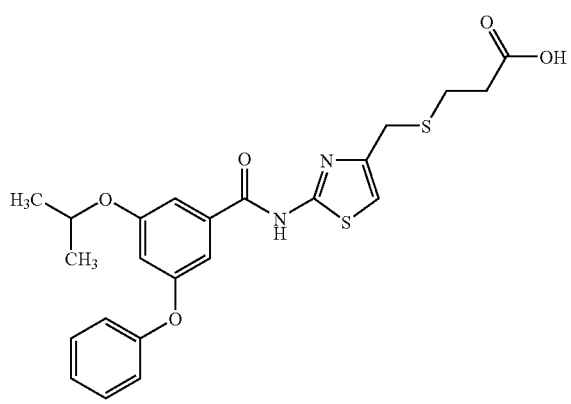

Step A:

3-[2-(3-Isopropoxy-5-phenoxy-benzoylamino)-thiazol-4-ylmethylsulfanyl]-propionic acid ethyl ester was prepared from 3-isopropoxy-5-phenoxy-benzoic acid and 3-(2-amino-thiazol-4-ylmethylsulfanyl)-propionic acid ethyl ester following general procedure A.

Step B:

3-[2-(3-Isopropoxy-5-phenoxy-benzoylamino)-thiazol-4-ylmethylsulfanyl]-propionic acid ethyl ester was hydrolysed following general procedure A. to give the title compound.

LC-MS (m/z): 473 (M+1)$^+$.

Example 79

General Procedure (A)

{2-[3-(4-Methanesulfonyl-phenoxy)-5-((S)-2-methoxy-1-methyl-ethoxy)-benzoylamino]-thiazol-4-ylmethylsulfanyl}-acetic acid

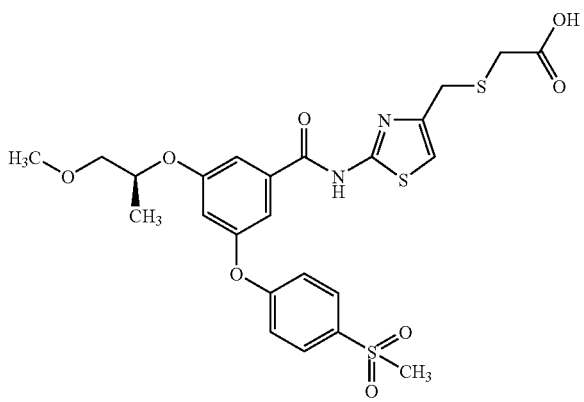

Step A:

{2-[3-(4-Methanesulfonyl-phenoxy)-5-((S)-2-methoxy-1-methyl-ethoxy)benzoylamino]-thiazol-4-ylmethylsulfanyl}-acetic acid methyl ester was prepared from 3-(4-methanesulfonyl-phenoxy)-5-((S)-2-methoxy-1-methyl-ethoxy)-benzoic acid and 3-(2-amino-thiazol-4-ylmethylsulfanyl)-acetic acid methyl ester following general procedure A.

Step B:

{2-[3-(4-Methanesulfonyl-phenoxy)-5-((S)-2-methoxy-1-methyl-ethoxy)benzoylamino]-thiazol-4-ylmethylsulfanyl}-acetic acid methyl ester was hydrolysed following general procedure A to give the title compound.

LC-MS (m/z): 567 (M+1)$^+$.

Example 80

General Procedure (A)

3-{2-[3-(4-Methanesulfonyl-phenoxy)-5-((S)-2-methoxy-1-methyl-ethoxy)-benzoylamino]-thiazol-4-ylmethylsulfanyl}-propionic acid

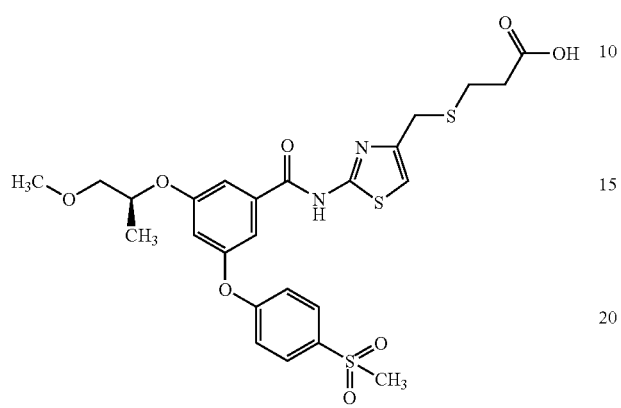

Step A:
3-{2-[3-(4-Methanesulfonyl-phenoxy)-5-((S)-2-methoxy-1-methyl-ethoxy)benzoylamino]-thiazol-4-ylmethylsulfanyl}-propionic acid ethyl ester was prepared from 4-(methanesulfonyl-phenoxy)-5-((S)-2-methoxy-1-methyl-ethoxy)-benzoic acid and 3-(2-amino-thiazol-4-ylmethylsulfanyl)-propionic acid ethyl ester following general procedure A.

Step B:
3-{2-[3-(4-Methanesulfonyl-phenoxy)-5-((S)-2-methoxy-1-methyl-ethoxy)benzoylamino]-thiazol-4-ylmethylsulfanyl}-propionic acid ethyl ester was hydrolysed following general procedure A to give the title compound.
LC-MS (m/z): 581 (M+1)$^+$.

Example 81

General Procedure (A)

{2-[3-(4-Fluoro-phenoxy)-5-((S)-2-methoxy-1-methyl-ethoxy)-benzoylamino]-thiazol-4-ylmethylsulfanyl}-acetic acid

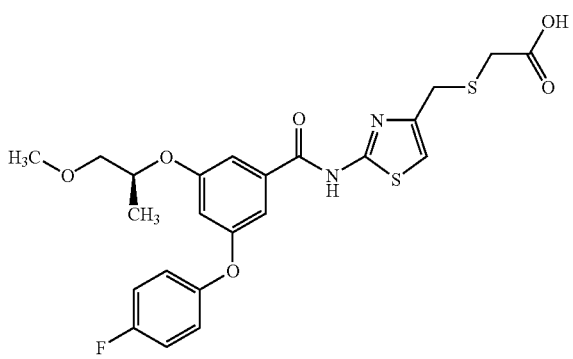

Step A:
{2-[3-(4-Fluoro-phenoxy)-5-((S)-2-methoxy-1-methyl-ethoxy)-benzoylamino]-thiazol-4-ylmethylsulfanyl}-acetic acid methyl ester was prepared from 3-(4-fluoro-phenoxy)-5-((S)-2-methoxy-1-methyl-ethoxy)-benzoic acid and 3-(2-amino-thiazol-4-ylmethylsulfanyl)-acetic acid methyl ester following general procedure A.

Step B:
{2-[3-(4-Fluoro-phenoxy)-5-((S)-2-methoxy-1-methyl-ethoxy)-benzoylamino]-thiazol-4-ylmethylsulfanyl}-acetic acid methyl ester was hydrolysed following general procedure A to give the title compound.
LC-MS (m/z): 507 (M+1)$^+$.

Example 82

General Procedure (A)

3-{2-[3-(4-Fluoro-phenoxy)-5-((S)-2-methoxy-1-methyl-ethoxy)-benzoylamino]-thiazol-4-ylmethylsulfanyl}-propionic acid

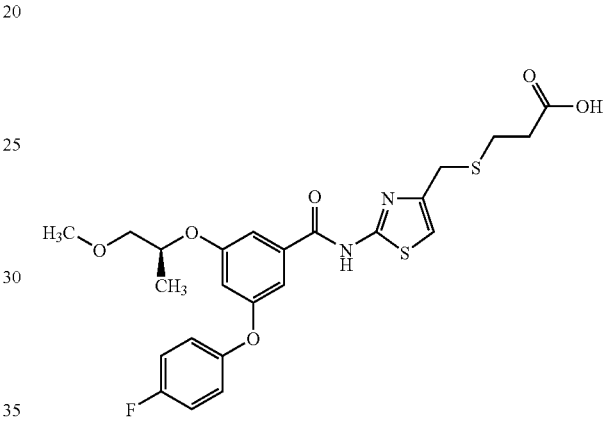

Step A:
3-{2-[3-(4-Fluoro-phenoxy)-5-((S)-2-methoxy-1-methyl-ethoxy)-benzoylamino]-thiazol-4-ylmethylsulfanyl}-propionic acid ethyl ester was prepared from 3-(4-fluoro-phenoxy)-5-((S)-2-methoxy-1-methyl-ethoxy)-benzoic acid and 3-(2-amino-thiazol-4-ylmethylsulfanyl)-propionic acid ethyl ester following general procedure A.

Step B:
3-{2-[3-(4-Methanesulfonyl-phenoxy)-5-((S)-2-methoxy-1-methyl-ethoxy)benzoylamino]-thiazol-4-ylmethylsulfanyl}-propionic acid ethyl ester was hydrolysed following general procedure A to give the title compound.
LC-MS (m/z): 521 (M+1)$^+$.

Pharmacological Methods

Glucokinase Activity Assay (I)

Glucokinase activity is assayed spectrometrically coupled to glucose 6-phosphate dehydrogenase to determine compound activation of glucokinase. The final assay contains 50 mM Hepes, pH 7.1, 50 mM KCl, 5 mM MgCl$_2$, 2 mM dithiothreitol, 0.6 mM NADP, 1 mM ATP, 0.195 µM G-6-P dehydrogenase (from Roche, 127 671), 15 nM recombinant human glucokinase. The glucokinase is human liver glucokinase N-terminally truncated with an N-terminal His-tag ((His)$_8$-VEQILA . . . Q466) and is expressed in *E. coli* as a soluble protein with enzymatic activity comparable to liver extracted GK.

The purification of His-tagged human glucokinase (hGK) was performed as follows: The cell pellet from 50 ml *E. coli* culture was resuspended in 5 ml extraction buffer A (25 mM HEPES, pH 8.0, 1 mM $MgCl_2$, 150 mM NaCl, 2 mM mercaptoethanol) with addition of 0.25 mg/ml lysozyme and 50 μg/ml sodium azide. After 5 minutes at room temperature 5 ml of extraction buffer B (1.5 M NaCl, 100 mM $CaCl_2$, 100 mM $MgCl_2$, 0.02 mg/ml DNase 1, protease inhibitor tablet (Complete® 1697498): 1 tablet pr. 20 ml buffer) was added. The extract was then centrifugated at 15.000 g for 30 minutes. The resulting supernatant was loaded on a 1 ml Metal Chelate Affinity Chromatography (MCAC) Column charged with $Ni^{2+}$. The column is washed with 2 volumes buffer A containing 20 mM imidazole and the bound his-tagged hGK is subsequently eluted using a 20 minute gradient of 20 to 500 mM imididazol in buffer A. Fractions are examined using SDS-gel-electrophoresis, and fractions containing hGK (MW: 52 KDa) are pooled. Finally a gelfiltration step is used for final polishing and buffer exchange. hGK containing fractions are loaded onto a Superdex 75 (16/60) gelfiltration column and eluted with Buffer B (25 mM HEPES, pH 8.0, 1 mM $MgCl_2$, 150 mM NaCl, 1 mM Dithiothreitol). The purified hGK is examined by SDS-gel electrophoresis and MALDI mass spectrometry and finally 20% glycerol is added before freezing. The yield from 50 ml E. coli culture is generally approximately 2-3 mg hGK with a purity >90%.

The compound to be tested is added into the well in final 2.5% DMSO concentration in an amount sufficient to give a desired concentration of compound, for instance 1, 5, 10, 25 or 50 μM. The reaction starts after glucose is added to a final concentration of 2, 5, 10 or 15 mM. The assay uses a 96-well UV plate and the final assay volume used is 200 μl/well. The plate is incubated at 25° C. for 5 min and kinetics is measured at 340 nm in SpectraMax every 30 seconds for 5 minutes. Results for each compound are expressed as the fold activation of the glucokinase activity compared to the activation of the glucokinase enzyme in an assay without compound after having been subtracted from a "blank", which is without glucokinase enzyme and without compound. The compounds in each of the Examples exhibits activation of glucokinase in this assay. A compound, which at a concentration of at or below 30 μM gives 1.5-fold higher glucokinase activity than the result from the assay without compound, is deemed to be an activator of glucokinase.

The glucose sensitivity of the compounds are measured at a compound concentration of 10 μM and at glucose concentrations of 5 and 15 mM.

Glucokinase Activity Assay (II)

Determination of Glycogen Deposition in Isolated Rat Hepatocytes:

Hepatocytes are isolated from rats fed ad libitum by a two-step perfusion technique. Cell viability, assessed by trypan blue exclusion, is consistently greater than 80%. Cells are plated onto collagen-coated 96-well plates in basal medium (Medium 199 (5.5 mM glucose) supplemented with 0.1 μM dexamethasone, 100 units/ml penicillin, 100 mg/ml streptomycin, 2 mM L-glutamine and 1 nM insulin) with 4% FCS at a cell density of 30,000 cells/well. The medium is replaced with basal medium 1 hour after initial plating in order to remove dead cells. Medium is changed after 24 hours to basal medium supplemented with 9.5 mM glucose and 10 nM insulin to induce glycogen synthesis, and experiments are performed the next day. The hepatocytes are washed twice with prewarmed (37° C.) buffer A (117.6 mM NaCl, 5.4 mM KCl, 0.82 mM $MgSO_4$, 1.5 mM $KH_2PO_4$, 20 mM HEPES, 9 mM $NaHCO_3$, 0.1% w/v HSA, and 2.25 mM $CaCl_2$, pH 7.4 at 37° C.) and incubated in 100 μl buffer A containing 15 mM glucose and increasing concentrations of the test compound, such as for instance 1, 5, 10, 25, 50 or 100 μM, for 180 minutes. Glycogen content is measured using standard procedures (Agius, L. et al, Biochem J. 266, 91-102 (1990). A compound, which when used in this assay gives an significant increase in glycogen content compared to the result from the assay without compound, is deemed to have activity in this assay.

Glucokinase Activity Assay (III)

Stimulation of Insulin Secretion by Glucokinase Activators in INS-1E Cells

The glucose responsive β-cell line INS-1E is cultivated as described by Asfari M et al., Endocrinology, 130, 167-178 (1992). The cells are then seeded into 96 well cell culture plates and grown to a density of approximately $5 \times 10^4$ per well. Stimulation of glucose dependent insulin secretion is tested by incubation for 2 hours in Krebs Ringer Hepes buffer at glucose concentrations from 2.5 to 15 mM with or without addition of glucokinase activating compounds in concentrations of for instance 1, 5, 10, 25, 50 or 100 μM, and the supernatants collected for measurements of insulin concentrations by ELISA (n=4). A compound, which when used in this assay gives an significant increase in insulin secretion in response to glucose compared to the result from the assay without compound, is deemed to have activity in this assay.

The invention claimed is:
1. A compound according to formula I

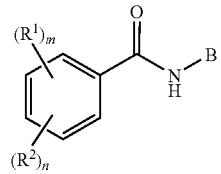

Formula I wherein
m is 0, 1, or 2;
n is 0, 1, 2, 3 or 4;
n+m>0;
Each $R^1$ is independently selected from the group consisting of OH, $—(CH_2)_{1-4}OH$, $—CH_{3-a}F_a$, $—(CH_2)_{1-4}—CH_{3-a}F_a$, $—OCH_{3-a}F_a$, Cl, F, Br, I, $C_{1-6}$-alkyl, $C_{2-6}$-alkenyl, $C_{2-6}$-alkynyl, amino, $C_{1-4}$-alkyl-amino, $C_{1-4}$-dialkykamino, cyano, formyl, phenyl, and 5-10 membered heterocyclyl, wherein the heterocyclyl consists of carbon atoms and 1-4 heteroatoms selected from the group consisting of O, N, and $S(O)_t$ optionally substituted with $C_{1-6}$-alkyl;
Each $R^2$ is a group Y—X—
wherein each X is independently —O—Z—, O—Z—O—Z—, —C(O)O—Z—, —OC(O)—Z—, —S—Z—, —S(O)—Z—, —S(O)$_2$—Z—, —N($R^6$)—Z—, —N($R^6$)S(O)$_2$—Z, —S(O)$_2$N($R^6$)—Z, —(CH$_2$)$_{1-4}$, —CH=CH—Z, —C≡C—Z, —N($R^6$)C(O)—Z, —C(O)N($R^6$)—Z, —C(O)N($R^6$)S(O)$_2$—Z, —S(O)$_2$—N($R^6$)C(O)—Z, —C(O)—Z, —Z, —C(O)—Z—O—Z, —N($R^6$)—C(O)—Z—O—Z, —O—Z—N($R^6$)—Z, —O—C(O)—Z—O—Z or a direct bond,
wherein X is attached to the phenyl ring by the first-mentioned atom;
Each Z is independently a direct bond, $C_{2-6}$-alkenylene, or —(CH$_2$)$_p$—C($R^{10}$)$_2$—(CH$_2$)$_q$—;

Each Y is independently aryl-$Z^1$—, a 5-10 membered heterocyclyl-$Z^1$—,
wherein the heterocyclyl consists of carbon atoms and 1-4 heteroatoms selected from the group consisting of O, N, and S(O)$_t$; $C_{3-7}$-cycloalkyl-$Z^1$—, $C_{1-6}$-alkyl, $C_{2-6}$-alkenyl, $C_{2-6}$-alkynyl, —(CH$_2$)$_{1-4}$—CH$_{3-a}$F$_a$, or —CH(OH)CH$_{3-a}$F$_a$, wherein each Y is optionally substituted with 1-3 substituents independently selected from $R^4$;
$Z^1$ is independently a direct bond, $C_{2-6}$-alkenylene, or —(CH$_2$)$_p$—C($R^{10}$)$_2$—(CH$_2$)$_q$—;
At each occurrence, p is independently selected from 0, 1, 2, or 3;
At each occurrence, q is independently selected from 0, 1, 2, or 3;
$R^4$ is independently $R^5$—$X^1$—, Cl, F, Br, I, CH$_{3-a}$F$_a$, —CN, NH$_2$, $C_{1-6}$-alkyl, —C(O)OH, —C(O)O$R^7$, OH, or phenyl optionally substituted by $R^7$;
or two $R^4$ attached to adjacent atoms may form a —O—(CH$_2$)$_{1-2}$—O— bridge;
or
$R^4$ is C(O)N$R^{26}R^{27}$, —S(O)$_2$N$R^{26}R^{27}$, —S(O)$_1R^{26}$ or HET-2;
$X^1$ is independently defined as X above:
$R^5$ is H, CH$_2$F, CHF$_2$, CF$_3$, phenyl, naphthyl, a 5-10 membered heterocyclyl consisting of carbon atoms and 1-4 heteroatoms selected from the group consisting of O, N, and S(O)$_t$, or $C_{3-7}$cycloalkyl, wherein each $R^5$ is optionally substituted by one or more substituents independently selected from $R^{25}$
$R^{25}$ is independently Cl, F, Br, I, CH$_{3-a}$F$_a$, —CN, OH, NH$_2$, C(O)OH, or —C(O)OC$_{1-6}$alkyl;
$R^6$ is independently hydrogen, $C_{1-6}$-alkyl, or —$C_{2-4}$-alkyl-O—$C_{1-4}$-alkyl;
$R^7$ is independently $C_{1-6}$-alkyl or —C(O)O$C_{1-6}$-alkyl;
B is

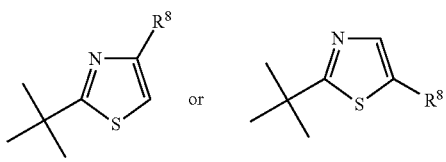

$R^8$ is S(O)$_r$(CH$_2$)$_s$—$R^9$;
r is 0, 1 or 2;
s is 1, 2, 3, or 4;
$R^9$ is independently carboxy, or —C(O)O—$C_{1-6}$-alkyl;
$R^{10}$ is independently H, Cl, F, Br, I, $C_{1-6}$-alkyl, or —$C_{2-4}$-alkyl-O—$C_{1-4}$alkyl;
$R^{18}$ is hydrogen or $C_{1-6}$-alkyl;
$R^{26}$ is
hydrogen,
$C_{1-4}$-alkyl optionally substituted with one or two substituents independently selected from the group consisting of
HET-2, —O$R^{27}$, —S(O)$_2R^{27}$, $C_{3-6}$-cycloalkyl, and —C(O)N$R^{27}R^{27}$,
$C_{3-6}$-cycloalkyl, or HET-2;
$R^{27}$ is hydrogen or $C_{1-4}$-alkyl;
or $R^{26}$ and $R^{27}$ together with the nitrogen atom to which they are attached form a heterocyclyl ring as defined in HET-3;
HET-2 is morpholino, furyl, imidazolyl, oxazolyl, isoxazolyl, oxadiazolyl, piperidinyl, piperazinyl, 3-oxo-piperazinyl, pyrrolidinyl, 2-pyrrolidonyl, tetrahydropyranyl, 1,1-dioxotetrahydrothienyl, or 2-oxo-imidazolidinyl, each of which is optionally substituted with on or two substituents independently selected from $R^{29}$;
HET-3 is a 4-, 5-, or 6-membered N-linked saturated or partially unsaturated heterocyclyl ring optionally containing 1 or 2 further heteroatoms (in addition to the linking nitrogen atom) independently selected from the group consisting of O, N, and S, wherein a —CH$_2$— group can optionally be replaced by a —C(O)— group, and wherein a sulphur atom in the ring may optionally be oxidized to an S(O) or S(O)$_2$ group, which ring is optionally substituted on an available carbon or nitrogen atom by one or two substituents independently selected from $R^{29}$; or
HET-3 is an N-linked, 7-membered saturated or partially unsaturated heterocyclyl ring optionally containing one further heteroatom (in addition to the linking nitrogen atom) independently selected from the group consisting of O, N, and S, wherein a —CH$_2$— group can optionally be replaced by a —C(O)—, and wherein a sulphur atom in the heterocyclic ring may optionally be oxidized to an S(O) or S(O)$_2$ group, which ring is optionally substituted on an available carbon or nitrogen atom by one or two substituents independently selected from $R^{29}$; or
HET-3 is a 6-10 membered bicyclic saturated or partially unsaturated heterocyclyl ring optionally containing one further nitrogen atom (in addition to the linking nitrogen atom), wherein a —CH$_2$— group can optionally be replaced by a —C(O)—, which ring is optionally substituted on an available carbon or nitrogen atom by one substituent independently selected from $R^{30}$;
$R^{29}$ is independently —O$R^{27}$, $C_{1-4}$-alkyl, —C(O)—$C_{1-4}$-alkyl, —C(O)N$R^{26}R^{27}$, $C_{1-4}$-alkylamino, di($C_{1-4}$-alkyl)amino, HET-3 (wherein said ring is unsubstituted), $C_{1-4}$-alkoxy$C_{1-4}$-alkyl, hydroxy$C_{1-4}$-alkyl, armor S(O)$_t R^{26}$;
$R^{30}$ is independently hydroxy, halo, fluoromethyl, difluoromethyl, trifluoromethyl, methyl, methoxy or cyano;
t is independently 0, 1, or 2;
a is independently 1, 2, or 3;
or a pharmaceutically acceptable salt thereof.

2. A compound according to claim 1 wherein $R^1$ is independently —CH$_2$F, —CHF$_2$, —CF$_3$, Cl, F, or $C_{1-6}$-alkyl.

3. A compound according to claim 1 wherein X is independently —O—Z— or —O—Z—O—Z—.

4. A compound according to claim 1 wherein Z is a direct bond or —(CH$_2$)$_p$—C($R^{10}$)$_2$—(CH$_2$)$_q$—.

5. A compound according to claim 1 wherein Y is phenyl-$Z^1$—, naphthyl-$Z^1$—, a 5-10 membered heterocyclyl-$Z^1$—, wherein the heterocyclyl consists of carbon atoms and 1-4 heteroatoms selected from the group consisting of O, N, and S(O)$_t$, or $C_{3-7}$cycloalkyl-$Z^1$—, wherein each Y is optionally substituted with 1-3 substituents independently selected from $R^4$.

6. A compound according to claim 1 wherein $R^4$ is independently $R^5$—$X^1$—, Cl, F, $C_{1-6}$-alkyl or —O$C_{1-6}$-alkyl.

7. A compound according to claim 1 wherein $X^1$ is O.

8. A compound according to claim 1 wherein $R^5$ is $C_{1-6}$alkyl, CH$_2$F, CHF$_2$, or CF$_3$, and each $R^5$ is optionally substituted by one or more substituents independently selected from $R^{25}$.

9. A compound according to claim 1 wherein two $R^4$ attached to adjacent atoms form a —O—(CH$_2$)$_1$—O— bridge.

10. A compound according to claim 1 wherein two $R^4$ attached to adjacent atoms form a —O—(CH$_2$)$_2$—O— bridge.

11. A compound according to claim 1 wherein $R^4$ is —C(O)NR$^{26}$R$^{27}$, —S(O)$_2$NR$^{26}$R$^{27}$ or HET-2.

12. A compound according to claim 1 wherein HET-3 is morpholino, piperidinyl, piperazinyl, pyrrolidinyl, or azetidinyl, each of which is optionally substituted with one or two substituents independently selected from R$^{29}$.

13. A compound according to claim 1 wherein R$^{30}$ is independently halo, fluoromethyl, difluoromethyl, trifluoromethyl, methyl, or methoxy.

14. A compound according to claim 1 wherein B is

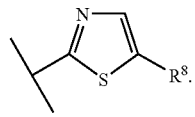

15. A compound according to claim 1 wherein R$^8$ is —S(O)$_2$(CH$_2$)$_{1-2}$—R$^9$.

16. A compound according to claim 1 wherein R$^8$ is —S(CH$_2$)$_{1-2}$—R$^9$.

17. A compound according to formula I

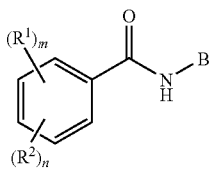

Formula I wherein
m is 0, 1, or 2;
n is 0, 1, 2, 3 or 4;
n+m>0;
Each R$^1$ is independently —CH$_2$F, —CHF$_2$, —CF$_3$, Cl, F, or C$_{1-6}$-alkyl;
Each R$^2$ is a group Y—X—
  wherein each X is independently —O—Z—, or —O—Z—O—Z—, wherein Z is a direct bond wherein X is attached to the phenyl ring by the first-mentioned atom;
Each Y is independently aryl-Z$^1$—, a 5-10 membered heterocyclyl-Z$^1$—, wherein the heterocyclyl consists of carbon atoms and 1-4 heteroatoms selected from the group consisting of O, N, and S(O)$_t$; C$_{3-7}$-cycloalkyl-Z$^1$—, C$_{1-6}$-alkyl, C$_{2-6}$-alkenyl, C$_{2-6}$-alkynyl, —(CH$_2$)$_{1-4}$—CH$_{3-a}$F$_a$, or —CH(OH)CH$_{3-a}$F$_a$, wherein each Y is optionally substituted with 1-3 substituents independently selected from R$^4$;

Z$^1$ is —(CH$_2$)$_p$—C(R$^{10}$)$_2$—(CH$_2$)$_q$—;

At each occurrence, p is independently selected from 0, 1, 2, or 3;

At each occurrence, q is independently selected from 0, 1, 2, or 3;

R$^4$ is independently R$^5$—X$^1$—, Cl, F, Br, I, CH$_{3-a}$F$_a$, —CN, NH$_2$, C$_{1-6}$-alkyl, —O—C$_{1-6}$alkyl, —C(O)OH, —C(O)OR$^7$, OH, or phenyl optionally substituted by R$^7$;

or two R$^4$ attached to adjacent atoms may form a —O—(CH$_2$)$_{1-2}$—O— bridge;

or

R$^4$ is R$^5$—X$^1$—, Cl, F, C$_{1-6}$-alkyl, or —OC$_{1-6}$-alkyl;

X$^1$ is independently defined as X above;

R$^5$ is C$_{1-6}$alkyl, CH$_2$F, CHF$_2$, or CF$_3$;

R$^7$ is independently C$_{1-6}$-alkyl or —C(O)OC$_{1-6}$-alkyl;

B is

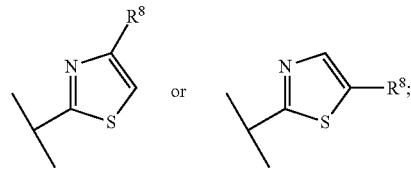

R$^8$ is —S(O)$_r$(CH$_2$)$_s$—R$^9$;
r is 0, 1 or 2;
s is 1, 2, 3, or 4;
R$^9$ is independently carboxy, or —C(O)O—C$_{1-6}$-alkyl;
R$^{10}$ is independently H, Cl, F, Br, I, C$_{1-6}$-alkyl, or —C$_{2-4}$-alkyl-O—C$_{1-4}$alkyl;
R$^{18}$ is hydrogen or C$_{1-6}$-alkyl;
t is independently 0, 1, or 2;
a is independently 1, 2, or 3;
or a pharmaceutically acceptable salt thereof.

* * * * *

UNITED STATES PATENT AND TRADEMARK OFFICE
CERTIFICATE OF CORRECTION

PATENT NO. : 7,880,012 B2  
APPLICATION NO. : 12/298852  
DATED : February 1, 2011  
INVENTOR(S) : Murray et al.

Page 1 of 1

It is certified that error appears in the above-identified patent and that said Letters Patent is hereby corrected as shown below:

In the Claims:

Claim 1, Column 84, Line 48: please delete "dialkykamino" and insert --dialkyl-amino--.

Claim 1, Column 84, Line 58: please delete "-C=C—Z," and insert -- -C≡C—Z--.

Claim 1, Column 85, Line 16: before "-C(O)OH," please insert -- -O-$C_{1-6}$alkyl,--.

Claim 1, Column 85, Line 21: please delete "-S(O)$_1$R$^{26}$" and insert -- -S(O)$_t$R$^{26}$--.

Claim 1, Column 85, Line 24: after "is H," please insert --$C_{1-6}$-alkyl,--.

Claim 1, Column 85, Line 29: at the end of the paragraph, please insert a --;--;

Claim 1, Column 85, Line 30: after "I," please insert --$C_{1-6}$-alkyl, -O$C_{1-6}$-alkyl,--.

Claim 1, Column 85, Line 40: after the second chemical structure, please insert a --;--.

Claim 1, Column 86, Line 3: please delete "on" and insert --one--.

Claim 1, Column 86, Line 36: please delete "armor S(O)$_t$R$^{26}$" and insert -- or -S(O)$_t$R$^{26}$--.

Signed and Sealed this  
Seventeenth Day of May, 2011

David J. Kappos  
*Director of the United States Patent and Trademark Office*